(12) United States Patent
Arrington et al.

(10) Patent No.: US 7,501,435 B2
(45) Date of Patent: Mar. 10, 2009

(54) INHIBITORS OF CHECKPOINT KINASES

(75) Inventors: Kenneth L. Arrington, Philadelphia, PA (US); Edward J. Brnardic, Lansdale, PA (US); Vadim Y. Dudkin, Lansdale, PA (US); Mark E. Fraley, North Wales, PA (US); Shaei Y. Huang, Lansdale, PA (US); Cheng Wang, King of Prussia, PA (US)

(73) Assignee: Merck & Co., Inc., Rahway, NJ (US)

( * ) Notice: Subject to any disclaimer, the term of this patent is extended or adjusted under 35 U.S.C. 154(b) by 101 days.

(21) Appl. No.: 11/789,288

(22) Filed: Apr. 24, 2007

(65) Prior Publication Data

US 2007/0254879 A1 Nov. 1, 2007

Related U.S. Application Data

(60) Provisional application No. 60/794,694, filed on Apr. 25, 2006.

(51) Int. Cl.
*A61K 31/4738* (2006.01)
*C07D 471/06* (2006.01)

(52) U.S. Cl. .......................... 514/287; 546/64; 544/125; 514/233.2

(58) Field of Classification Search ................ 514/287, 514/233.2; 546/64; 544/125
See application file for complete search history.

(56) References Cited

U.S. PATENT DOCUMENTS 3,652,570 A    3/1972    Gittos et al.
5,677,309 A    10/1997   Chen et al.
5,688,803 A    11/1997   Buttelmann et al.

FOREIGN PATENT DOCUMENTS

WO    WO 2004/081008    9/2004
WO    WO 2006/135627   12/2006
WO    WO 2007/081572    7/2007

OTHER PUBLICATIONS

Database Chem. Abstracts Service, XP002449423.
G. Sidgu, et al., Journal of Hetero. Chem., vol. 3, No. 2, pp. 158-164 (ISSN 0022-152X), 1966.
H. Reimlinger, et al., Chemishe Berichte, vol. 103, No. 6, pp. 1960-1981, 1970.
H. Reimlinger, et al., Chemishe Berichte, vol. 104, No. 12, pp. 3955-3960, 1971.
E. Braye, et al., European Journal of Medicinal Chem., vol. 9, No. 2, pp. 197-201 (ISSN 0223-5234), 1974.
G. Wagner, et al., Kurze Orginalmitteilungen, vol. 47, No. 12, p. 943 (ISSN 0031-7144), 1992.
B. Lal, et al., J. Org. Chem., vol. 55, No. 17, pp. 5117-5124, 1990.
Database: C. Chiu, et al, vol. 49, No. 2, pp. 239-250, No. 9265059 (XP002449424), 2002.
Database: Crossfire Beilstein, vol. 44, No. 1, pp. 17-28 (XP002449425), 1989.
Database: Crossfire Beilstein, vol. 126, No. 6/7, pp. 767-772 (XP002449426), 1995.

*Primary Examiner*—Charanjit S Aulakh
(74) *Attorney, Agent, or Firm*—Li Su; David A. Muthard

(57) ABSTRACT

The instant invention provides for compounds which comprise substituted triazoloquinazolinones that inhibit CHK1 activity. The invention also provides for compositions comprising such inhibitory compounds and methods of inhibiting CHK1 activity by administering the compound to a patient in need of treatment of cancer.

5 Claims, No Drawings

INHIBITORS OF CHECKPOINT KINASES

RELATED APPLICATIONS

This application claims priority from the U.S. Provisional Application No. 60/794,694, filed on Apr. 25, 2006.

BACKGROUND OF THE INVENTION

Cell cycle checkpoints are regulatory pathways that control the order and timing of cell cycle transitions. They ensure that critical events such as DNA replication and chromosome segregation are completed in high fidelity. The regulation of these cell cycle checkpoints is a critical determinant of the manner in which tumor cells respond to many chemotherapies and radiation. Many effective cancer therapies work by causing DNA damage; however, resistance to these agents remains a significant limitation in the treatment of cancer. Of the several mechanisms of drug resistance, an important one is attributed to the prevention of cell cycle progression through the control of critical activation of a checkpoint pathway. This arrests the cell cycle to provide time for repair, and induces the transcription of genes to facilitate repair, thereby avoiding immediate cell death. By abrogating checkpoint arrests at, for example, the G2 checkpoint, it may be possible to synergistically augment tumor cell death induced by DNA damage and circumvent resistance.

Human CHK1 plays a role in regulating cell cycle arrest by phosphorylating the phosphatase cdc25 on Serine 216, which may be involved in preventing activation of cdc2/cyclin B and initiating mitosis. Therefore, inhibition of CHK1 should enhance DNA damaging agents by initiating mitosis before DNA repair is complete and thereby causing tumor cell death.

It is an object of the instant invention to provide novel compounds that are inhibitors of CHK1 (also refered to as Chek1).

It is also an object of the present invention to provide pharmaceutical compositions that comprise the novel compounds that are inhibitors of CHK1.

It is also an object of the present invention to provide a method for treating cancer that comprises administering such inhibitors of CHK1 activity.

SUMMARY OF THE INVENTION

The instant invention provides for compounds which comprise substituted triazoloquinazolinones that inhibit CHK1 activity. The invention also provides for compositions comprising such inhibitory compounds and methods of inhibiting CHK1 activity by administering the compound to a patient in need of treatment of cancer.

DETAILED DESCRIPTION OF THE INVENTION

The compounds of the instant invention are useful in the inhibition of the activity of CHK1. In a first embodiment of this invention, the inhibitors of CHK1 activity are illustrated by the Formula A:

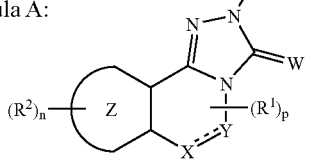

wherein:
a is 0 or 1; b is 0 or 1; m is 0, 1, or 2; n is 0, 1, 2, 3, 4, 5 or 6; p is 0, 1 or 2;
the dashed line between X and Y represents an optional double bond;
W is selected from: O, S and N—$R^4$;
X and Y are independently selected from: $CH_2$ and NH;
Ring Z is selected from: aryl, heteroaryl, heterocyclyl, $(C_4-C_8)$cycloalkenyl and $(C_4-C_8)$cycloalkyl;
$R^1$ is independently selected from: H, $CF_3$, oxo, $(C=O)_aO_bC_1-C_{10}$ alkyl, $(C=O)_aO_b$ aryl, $(C=O)_aO_bC_2-C_{10}$ alkenyl, $(C=O)_aO_bC_2-C_{10}$ alkynyl, $CO_2H$, halo, OH, $O_bC_1-C_6$ perfluoroalkyl, $(C=O)_aNR^7R^8$, CN, $(C=O)_aO_bC_3-C_8$ cycloalkyl, $S(O)_mNR^7R^8$, $S(O)_m-(C_1-C_{10})$alkyl, and $(C=O)_aO_b$heterocyclyl, said alkyl, aryl, alkenyl, alkynyl, cycloalkyl, and heterocyclyl is optionally substituted with one or more substituents selected from $R^6$;
$R^2$ is independently selected from: H, $CF_3$, oxo, $(C=O)_aO_bC_1-C_{10}$ alkyl, $(C=O)_aO_b$ aryl, $(C=O)_aO_bC_2-C_{10}$ alkenyl, $(C=O)_aO_bC_2-C_{10}$ alkynyl, $CO_2H$, halo, OH, $O_bC_1-C_6$ perfluoroalkyl, $(C=O)_aNR^7R^8$, CN, $(C=O)_aO_bC_3-C_8$ cycloalkyl, $S(O)_mNR^7R^8$, $S(O)_m-(C_1-C_{10})$alkyl, and $(C=O)_aO_b$heterocyclyl, said alkyl, aryl, alkenyl, alkynyl, cycloalkyl, and heterocyclyl is optionally substituted with one or more substituents selected from $R^6$, or two $R^2$s can be taken together to form a monocyclic or bicyclic heterocycle with 3-7 members in each ring and optionally containing one, two or three additional heteroatoms selected from N, O and S, said monocyclic or bicyclic heterocycle optionally substituted with one or more substituents selected from $R_{6a}$;
$R^3$ is selected from: H, $CF_3$, oxo, $(C=O)_aO_bC_1-C_{10}$ alkyl, $(C=O)_aO_b$ aryl, $(C=O)_aO_bC_2-C_{10}$ alkenyl, $(C=O)_aO_bC_2-C_{10}$ alkynyl, $CO_2H$, halo, OH, $O_bC_1-C_6$ perfluoroalkyl, $(C=O)_aNR^7R^8$, CN, $(C=O)_aO_bC_3-C_8$ cycloalkyl, $S(O)_mNR^7R^8$, $S(O)_m-(C_1-C_{C10})$alkyl, and $(C=O)_aO_b$heterocyclyl, said alkyl, aryl, alkenyl, alkynyl, cycloalkyl, and heterocyclyl is optionally substituted with one or more substituents selected from $R^6$;
$R^4$ is selected from: H, CF3, oxo, $(C=O)_aO_bC_1-C_{10}$ alkyl, $(C=O)_aO_b$ aryl, $(C=O)_aO_bC_2-C_{10}$ alkenyl, $(C=O)_aO_bC_2-C_{10}$ alkynyl, $CO_2H$, halo, OH, $O_bC_1-C_6$ perfluoroalkyl, $(C=O)_aNR^7R^8$, CN, $(C=O)_aO_bC_3-C_8$ cycloalkyl, $S(O)_mNR^7R^8$, $S(O)_m-(C_1-C_{10})$alkyl, and $(C=O)_aO_b$heterocyclyl, said alkyl, aryl, alkenyl, alkynyl, cycloalkyl, and heterocyclyl is optionally substituted with one or more substituents selected from $R^6$;
$R^6$ is: $CF_3$, oxo, $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_b$ $NR^7R^8$, oxo, CHO, $(N=O)R^7R^8$, $S(O)_mNR^7R^8$, $S(O)_m-(C_1-C_{10})$alkyl, SH or $(C=O)_aO_bC_3-C_8$ cycloalkyl, said alkyl, aryl, alkenyl, alkynyl, heterocyclyl, and cycloalkyl optionally substituted with one or more substituents selected from $R^{6a}$;
$R^{6a}$ is selected from: $CF_3$, $(C=O)_aO_b(C_1-C_{10})$alkyl, $O_a(C_1-C_3)$perfluoroalkyl, $(C_0-C_6)$alkylene-$S(O)_mR^a$, oxo, OH, halo, CN, $(C_2-C_{10})$alkenyl, $(C_2-C_{10})$alkynyl, $(C_3-C_6)$ cycloalkyl, $(C_0-C_6)$alkylene-aryl, $(C_0-C_6)$alkylene-heterocyclyl, $(C_0-C_6)$alkylene-$N(R^b)_2$, $C(O)R^a$, $(C_0-C_6)$alkylene-$CO_2R^a$, $C(O)H$, and $(C_0-C^6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^7$ and $R^8$ are independently selected from: H, $(C=O)$ $O_bC_1-C_{10}$ alkyl, $(C=O)O_bC_3-C_8$ cycloalkyl, $(C=O)O_b$aryl, $(C=O)O_b$heterocyclyl, $C_1-C_{10}$ alkyl, aryl, $C_2-C_{10}$ alkenyl, $C_2-C_{10}$ alkynyl, heterocyclyl, $C_3-C_8$ cycloalkyl, $S(O)_mR^a$, and (C═O)NR$^b$2, said alkyl, cycloalkyl, aryl, heterocylyl, alkenyl, and alkynyl is optionally substituted with one or more substituents selected from R$^{6a}$, or R$^7$ and R$^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocylcic or bicyclic heterocycle optionally substituted with one or more substituents selected from R$^{6a}$;

R$^a$ is H, (C$_1$-C$_6$)alkyl, (C$_3$-C$_6$)cycloalkyl, aryl, or heterocyclyl; and R$^b$ is independently H, (C$_1$-C$_6$)alkyl, aryl, heterocyclyl, (C$_3$-C$_6$)cycloalkyl, (C═O)OC$_1$-C$_6$ alkyl, (C═O)C$_1$-C$_6$ alkyl or S(O)$_m$R$^a$;

or a pharmaceutically acceptable salt or a stereoisomer thereof.

In a second embodiment of this invention, the inhibitors of CHK1 activity are illustrated by the Formula B:

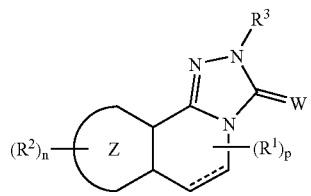

B wherein:
all other substituents and variables are as defined in the first embodiment;
or a pharmaceutically acceptable salt or a stereoisomer thereof.

In a third embodiment of this invention, the inhibitors of CHK1 activity are illustrated by the Formula C:

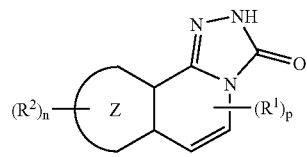

C wherein:
Ring Z is selected from phenyl and naphthyl;
all other substituents and variables are as defined in the first embodiment;
or a pharmaceutically acceptable salt or a stereoisomer thereof.

In a fourth embodiment of this invention, the inhibitors of CHK1 activity are illustrated by the Formula D:

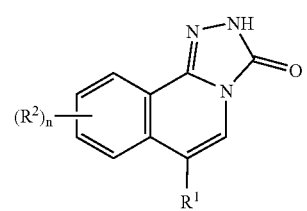

D wherein:
n is 0, 1, 2, 3 or 4;
all other substituents and variables are as defined in the first embodiment;
or a pharmaceutically acceptable salt or a stereoisomer thereof.

In a fifth embodiment of this invention, the inhibitors of CHK1 activity are illustrated by the Formula E:

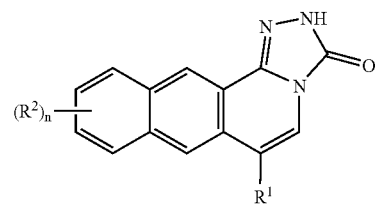

E wherein:
all other substituents and variables are as defined in the first embodiment;
or a pharmaceutically acceptable salt or a stereoisomer thereof.

Specific compounds of the instant invention include:
9-(1H-pyrazol-4-yl)[1,2,4]triazolo[3,4-a]isoquinolin-3(2H)-one (1-4);
9-pyridin-3-yl[1,2,4]triazolo[3,4-a]isoquinolin-3(2H)-one (1-5);
9-chloro[1,2,4]triazolo[3,4-a]isoquinolin-3(2H)-one (1-6);
9-(1H-pyrrol-2-yl)[1,2,4]triazolo[3,4-a]isoquinolin-3(2H)-one (1-7);
9-(1-methyl-1H-pyrazol-4-yl)[1,2,4]triazolo[3,4-a]isoquinolin-3(2H)-one (1-8);
9-(1-isobutyl-1H-pyrazol-4-yl)[1,2,4]triazolo[3,4-a]isoquinolin-3(2H)-one (1-9);
9-(3,5-dimethyl-1H-pyrazol-4-yl)[1,2,4]triazolo[3,4-a]isoquinolin-3(2H)-one (1-10);
9-(1,3,5-trimethyl-1H-pyrazol-4-yl)[1,2,4]triazolo[3,4-a]isoquinolin-3(2H)-one (1-11);
9-(5-methyl-2-furyl)[1,2,4]triazolo[3,4-a]isoquinolin-3(2H)-one (1-12);
9-(4-methyl-2-thienyl)[1,2,4]triazolo[3,4-a]isoquinolin-3(2H)-one (1-13);
9-(3-thienyl)[1,2,4]triazolo[3,4-a]isoquinolin-3(2H)-one (1-14);
9-(4-methyl-3-thienyl)[1,2,4]triazolo[3,4-a]isoquinolin-3(2H)-one (1-15);
9-(3-furyl)[1,2,4]triazolo[3,4-a]isoquinolin-3(2H)-one (1-16);
9-(2-furyl)[1,2,4]triazolo[3,4-a]isoquinolin-3(2H)-one (1-17);
9-(3,5-dimethylisoxazol-4-yl)[1,2,4]triazolo[3,4-a]isoquinolin-3(2H)-one (1-18); 9-[(1E)-3-aminoprop-1-en-1-yl][1,2,4]triazolo[3,4-a]isoquinolin-3(2H)-one (1-20);
9-(2-chloropyridin-4-yl)[1,2,4]triazolo[3,4-a]isoquinolin-3(2H)-one (1-20);
9-(6-morpholin-4-ylpyridin-3-yl)[1,2,4]triazolo[3,4-a]isoquinolin-3(2H)-one (1-21);
9-pyridin-4-yl[1,2,4]triazolo[3,4-a]isoquinolin-3(2H)-one (1-22);
9-quinolin-3-yl[1,2,4]triazolo[3,4-a]isoquinolin-3(2H)-one (1-23);
9-pyrimidin-5-yl[1,2,4]triazolo[3,4-a]isoquinolin-3(2H)-one (1-24);

9-(2,4-dimethoxypyrimidin-5-yl)[1,2,4]triazolo[3,4-a]isoquinolin-3(2H)-one (1-25);
9-[4-(aminomethyl)phenyl][1,2,4]triazolo[3,4-a]isoquinolin-3(2H)-one (1-26);
6-(2-aminoethoxy)[1,2,4]triazolo[3,4-a]isoquinolin-3(2H)-one (2-4);
6-(3-aminopropoxy)[1,2,4]triazolo[3,4-a]isoquinolin-3(2H)-one (2-5);
6-[(1E)-3-aminoprop-1-en-1-yl]-9-chloro[1,2,4]triazolo[3,4-a]isoquinolin-3(2H)-one (3-11);
6-(3-aminopropyl)-9-chloro[1,2,4]triazolo[3,4-a]isoquinolin-3(2H)-one (3-13);
6-bromo[1,2,4]triazolo[3,4-a]isoquinolin-3(2H)-one (3-14);
6-[(1E)-3-aminoprop-1-en-1-yl][1,2,4]triazolo[3,4-a]isoquinolin-3(2H)-one (3-15);
6-(3-aminopropyl)[1,2,4]triazolo[3,4-a]isoquinolin-3(2H)-one (3-16);
6,7,8,9-tetrahydrobenzo[f][1,2,4]triazolo[3,4-a]isoquinolin-1(2H)-one (3-17);
8,9,10,11-tetrahydrobenzo[g][1,2,4]triazolo[3,4-a]isoquinolin-3(2H)-one (3-18);
benzo[g][1,2,4]triazolo[3,4-a]isoquinolin-3(2H)-one (3-19);
6-(3-hydroxypropyl)[1,2,4]triazolo[3,4-a]isoquinolin-3(2H)-one (4-2);
6-[3-(methylamino)propyl][1,2,4]triazolo[3,4-a]isoquinolin-3(2H)-one (5-6);
6-{3-[(2,2,2-trifluoroethyl)amino]propyl}[1,2,4]triazolo[3,4-a]isoquinolin-3(2H)-one (5-7);
6-[3-(ethylamino)propyl][1,2,4]triazolo[3,4-a]isoquinolin-3(2H)-one (5-8);
6-(3-amino-2-fluoropropyl)-9-chloro[1,2,4]triazolo[3,4-a]isoquinolin-3(2H)-one (6-5);
6-[(1E)-3-aminoprop-1-en-1-yl]benzo[g][1,2,4]triazolo[3,4-a]isoquinolin-3(2H)-one (7-8);
6-(3-aminopropyl)benzo[g][1,2,4]triazolo[3,4-a]isoquinolin-3(2H)-one (7-10);
6-(3-aminopropyl)-5,6-dihydrobenzo[g][1,2,4]triazolo[3,4-a]isoquinolin-3(2H)-one (7-11);
6-pyridin-3-ylbenzo[g][1,2,4]triazolo[3,4-a]isoquinolin-3(2H)-one (7-12);
6-[4-(aminomethyl)phenyl]benzo[g][1,2,4]triazolo[3,4-a]isoquinolin-3(2H)-one (7-13);
6-[4-(morpholin-4-ylmethyl)phenyl]benzo[g][1,2,4]triazolo[3,4-a]isoquinolin-3(2H)-one (7-14);
6-(1,2,3,6-tetrahydro-4-pyridinyl)-benzo[g]-1,2,4-triazolo[3,4-a]isoquinolin-3(2H)-one (7-15);
6-(6-aminopyridin-3-yl)benzo[g][1,2,4]triazolo[3,4-a]isoquinolin-3(2H)-one (7-16);
6-[3-(morpholin-4-ylmethyl)phenyl]benzo[g][1,2,4]triazolo[3,4-a]isoquinolin-3(2H)-one (7-17);
6-[3-(piperidin-1-ylmethyl)phenyl]benzo[g][1,2,4]triazolo[3,4-a]isoquinolin-3(2H)-one (7-18);
6-[3-(aminomethyl)phenyl]benzo[g][1,2,4]triazolo[3,4-a]isoquinolin-3(2H)-one (7-19);
6-(2-aminoethyl)benzo[g][1,2,4]triazolo[3,4-a]isoquinolin-3(2H)-one (7-20);
6-isoquinolin-5-ylbenzo[g][1,2,4]triazolo[3,4-a]isoquinolin-3(2H)-one (7-21);
6-quinolin-5-ylbenzo[g][1,2,4]triazolo[3,4-a]isoquinolin-3(2H)-one (7-22);
6-(3-aminophenyl)benzo[g][1,2,4]triazolo[3,4-a]isoquinolin-3(2H)-one (7-23);
6-piperidin-4-ylbenzo[g][1,2,4]triazolo[3,4-a]isoquinolin-3(2H)-one (7-24);
2,2,2-trifluoro-N-[4-(3-oxo-2,3-dihydrobenzo[g][1,2,4]triazolo[3,4-a]isoquinolin-6-yl)phenyl]acetamide (7-25);
6-(4-aminophenyl)benzo[g][1,2,4]triazolo[3,4-a]isoquinolin-3(2H)-one (7-26);
6-pyridin-4-ylbenzo[g][1,2,4]triazolo[3,4-a]isoquinolin-3(2H)-one (7-27);
6-(3-aminopropyl)-10-methylbenzo[g][1,2,4]triazolo[3,4-a]isoquinolin-3(2H)-one (7-28);
6-(3-aminopropyl)-10-fluorobenzo[g][1,2,4]triazolo[3,4-a]isoquinolin-3(2H)-one (7-29);
6-(3-aminopropyl)-9,11-difluorobenzo[g][1,2,4]triazolo[3,4-a]isoquinolin-3(2H)-one (7-30);
tert-butyl [(2Z)-3-(10-methyl-3-oxo-2,3-dihydrobenzo[g][1,2,4]triazolo[3,4-a]isoquinolin-3(2H)-one (7-31);
6-[(1Z)-3-aminoprop-1-en-1-yl]-10-methylbenzo[g][1,2,4]triazolo[3,4-a]isoquinolin-3(2H)-one (7-32);
6-[(1Z)-3-aminoprop-1-en-1-yl]-10-chlorobenzo[g][1,2,4]triazolo[3,4-a]isoquinolin-3(2H)-one (7-33);
6-[4-(aminomethyl)phenyl]-10-methylbenzo[g][1,2,4]triazolo[3,4-a]isoquinolin-3(2H)-one (7-34);
6-(3-aminopropyl)-10-chlorobenzo[g][1,2,4]triazolo[3,4-a]isoquinolin-3(2H)-one (7-35);
6-[(1Z)-3-aminoprop-1-en-1-yl]-9,10-difluorobenzo[g][1,2,4]triazolo[3,4-a]isoquinolin-3(2H)-one (7-36);
6-(3-aminopropyl)-9,10-difluorobenzo[g][1,2,4]triazolo[3,4-a]isoquinolin-3(2H)-one (7-37);
6-(3-aminopropyl)-10-(trifluoromethyl)benzo[g][1,2,4]triazolo[3,4-a]isoquinolin-3(2H)-one (7-38);
6-(3-aminopropyl)-2,6-dihydrobenzo[g][1,2,4]triazolo[4,3-c]quinazoline-3,5-dione (8-8);
2,6-dihydro benzo[g][1,2,4]triazolo[4,3-c]quinazoline-3,5-dione (8-9); and
6-(3-aminopropyl)-2,6-dihydrobenzo[g][1,2,4]triazolo[4,3-c]quinazoline-3,5-dione (8-10);
or a pharmaceutically acceptable salt or a stereoisomer thereof.

TFA salts of the compounds of the instant invention include:
9-(1H-pyrazol-4-yl)[1,2,4]triazolo[3,4-a]isoquinolin-3(2H)-one (1-4);
9-pyridin-3-yl [1,2,4]triazolo[3,4-a]isoquinolin-3(2H)-one (1-5);
9-chloro[1,2,4]triazolo[3,4-a]isoquinolin-3(2H)-one (1-6);
9-(1H-pyrrol-2-yl)[1,2,4]triazolo[3,4-a]isoquinolin-3(2H)-one (1-7);
9-(1-methyl-1H-pyrazol-4-yl)[1,2,4]triazolo[3,4-a]isoquinolin-3(2H)-one (1-8);
9-(1-isobutyl-1H-pyrazol-4-yl)[1,2,4]triazolo[3,4-a]isoquinolin-3(2H)-one (1-9);
9-(3,5-dimethyl-1H-pyrazol-4-yl)[1,2,4]triazolo[3,4-a]isoquinolin-3(2H)-one (1-10);
9-(1,3,5-trimethyl-1H-pyrazol-4-yl)[1,2,4]triazolo[3,4-a]isoquinolin-3(2H)-one (1-11);
9-(5-methyl-2-furyl)[1,2,4]triazolo[3,4-a]isoquinolin-3(2H)-one (1-12);
9-(4-methyl-2-thienyl)[1,2,4]triazolo[3,4-a]isoquinolin-3(2H)-one (1-13);
9-(3-thienyl)[1,2,4]triazolo[3,4-a]isoquinolin-3(2H)-one (1-14);
9-(4-methyl-3-thienyl)[1,2,4]triazolo[3,4-a]isoquinolin-3(2H)-one (1-15);
9-(3-furyl)[1,2,4]triazolo[3,4-a]isoquinolin-3(2H)-one (1-16);
9-(2-furyl)[1,2,4]triazolo[3,4-a]isoquinolin-3(2H)-one (1-17);
9-(3,5-dimethylisoxazol-4-yl)[1,2,4]triazolo[3,4-a]isoquinolin-3(2H)-one (1-18);
9-[(1E)-3-aminoprop-1-en-1-yl][1,2,4]triazolo[3,4-a]isoquinolin-3(2H)-one (1-19);

9-(2-chloropyridin-4-yl)[1,2,4]triazolo[3,4-a]isoquinolin-3 (2H)-one (1-20);
9-(6-morpholin-4-ylpyridin-3-yl)[1,2,4]triazolo[3,4-a]isoquinolin-3(2H)-one (1-21);
9-pyridin-4-yl [1,2,4]triazolo[3,4-a]isoquinolin-3(2H)-one (1-22);
9-quinolin-3-yl [1,2,4]triazolo[3,4-a]isoquinolin-3(2H)-one (1-23);
9-pyrimidin-5-yl [1,2,4]triazolo[3,4-a]isoquinolin-3(2H)-one (1-24);
9-(2,4-dimethoxypyrimidin-5-yl)[1,2,4]triazolo[3,4-a]isoquinolin-3(2H)-one (1-25);
9-[4-(aminomethyl)phenyl][1,2,4]triazolo[3,4-a]isoquinolin-3(2H)-one (1-26);
6-(2-aminoethoxy)[1,2,4]triazolo[3,4-a]isoquinolin-3(2H)-one (2-4);
6-(3-aminopropoxy)[1,2,4]triazolo[3,4-a]isoquinolin-3(2H)-one (2-5);
6-[(1E)-3-aminoprop-1-en-1-yl]-9-chloro[1,2,4]triazolo[3,4-a]isoquinolin-3(2H)-one (3-11);
6-(3-aminopropyl)-9-chloro[1,2,4]triazolo[3,4-a]isoquinolin-3(2H)-one (3-13);
6-bromo[1,2,4]triazolo[3,4-a]isoquinolin-3(2H)-one (3-14);
6-[(1E)-3-aminoprop-1-en-1-yl][1,2,4]triazolo[3,4-a]isoquinolin-3(2H)-one (3-15);
6-(3-aminopropyl)[1,2,4]triazolo[3,4-a]isoquinolin-3(2H)-one (3-16);
6,7,8,9-tetrahydrobenzo[f][1,2,4]triazolo[3,4-a]isoquinolin-1(2H)-one (3-17);
8,9,10,11-tetrahydrobenzo[g][1,2,4]triazolo[3,4-a]isoquinolin-3(2H)-one (3-18);
benzo[g][1,2,4]triazolo[3,4-a]isoquinolin-3(2H)-one (3-19);
6-(3-hydroxypropyl)[1,2,4]triazolo[3,4-a]isoquinolin-3(2H)-one (4-2);
6-[3-(methylamino)propyl][1,2,4]triazolo[3,4-a]isoquinolin-3(2H)-one (5-6);
6-{3-[(2,2,2-trifluoroethyl)amino]propyl}[1,2,4]triazolo[3,4-a]isoquinolin-3(5-7);
6-[3-(ethylamino)propyl][1,2,4]triazolo[3,4-a]isoquinolin-3(2H)-one (5-8);
6-(3-amino-2-fluoropropyl)-9-chloro[1,2,4]triazolo[3,4-a]isoquinolin-3(2H)-one (6-5);
6-[(1E)-3-aminoprop-1-en-1-yl)benzo[g][1,2,4]triazolo[3,4-a]isoquinolin-3(2H)-one (7-8);
6-(3-aminopropyl)-5.6-dihydrobenzo[g][1,2,4]triazolo[3,4-a]isoquinolin-3(2H)-one (7-11);
6-pyridin-3-ylbenzo[g][1,2,4]triazolo[3,4-a]isoquinolin-3(2H)-one (7-12);
6-[4-(aminomethyl)phenyl]benzo[g][1,2,4]triazolo[3,4-a]isoquinolin-3(2H)-one (7-13);
6-[4-(morpholin-4-ylmethyl)phenyl]benzo[g][1,2,4]triazolo[3,4-a]isoquinolin-3(2H)-one (7-14);
6-(1,2,3,6-tetrahydro-4-pyridinyl)-benzo[g]-1,2,4-triazolo[3,4-a]isoquinolin-3(2H)-one (7-15);
6-(6-aminopyridin-3-yl)benzo[g][1,2,4]triazolo[3,4-a]isoquinolin-3(2H)-one (7-16);
6-[3-(morpholin-4-ylmethyl)phenyl]benzo[g][1,2,4]triazolo[3,4-a]isoquinolin-3(2H)-one (7-17);
6-[3-(piperidin-1-ylmethyl)phenyl]benzo[g][1,2,4]triazolo[3,4-a]isoquinolin-3(2H)-one (7-18);
6-[3-(aminomethyl)phenyl]benzo[g][1,2,4]triazolo[3,4-a]isoquinolin-3(2H)-one (7-19);
6-(2-aminoethyl)benzo[g][1,2,4]triazolo[3,4-a]isoquinolin-3(2H)-one (7-20);
6-isoquinolin-5-ylbenzo[g][1,2,4]triazolo[3,4-a]isoquinolin-3(2H)-one (7-21);
6-quinolin-5-ylbenzo[g][1,2,4]triazolo[3,4-a]isoquinolin-3(2H)-one (7-22);
6-(3-aminophenyl)benzo[g][1,2,4]triazolo[3,4-a]isoquinolin-3(2H)-one (7-23);
6-piperidin-4-ylbenzo[g][1,2,4]triazolo[3,4-a]isoquinolin-3(2H)-one (7-24);
2,2,2-trifluoro-N-[4-(3-oxo-2,3-dihydrobenzo[g][1,2,4]triazolo[3,4-a]isoquinolin-6-yl)phenyl]acetamide (7-25);
6-(4-aminophenyl)benzo[g][1,2,4]triazolo[3,4-a]isoquinolin-3(2H)-one (7-26);
6-pyridin-4-ylbenzo[g][1,2,4]triazolo[3,4-a]isoquinolin-3(2H)-one (7-27);
6-(3-aminopropyl)-10-methylbenzo[g][1,2,4]triazolo[3,4-a]isoquinolin-3(2H)-one (7-28;
6-(3-aminopropyl)-10-fluorobenzo[g][1,2,4]triazolo[3,4-a]isoquinolin-3(2H)-one (7-29);
6-(3-aminopropyl)-9,11-difluorobenzo[g][1,2,4]triazolo[3,4-a]isoquinolin-3(2H)-one (7-30);
tert-butyl [(2Z)-3-(10-methyl-3-oxo-2,3-dihydrobenzo[g][1,2,4]triazolo[3,4-a]isoquinolin-3(2H)-one (7-31);
6-[(1Z)-3-aminoprop-1-en-1-yl]-10-methylbenzo[g][1,2,4]triazolo[3,4-a]isoquinolin-3(2H)-one (7-32);
6-[(1Z)-3-aminoprop-1-en-1-yl]-10-chlorobenzo[g][1,2,4]triazolo[3,4-a]isoquinolin-3(2H)-one (7-33);
6-[4-(aminomethyl)phenyl]-10-methylbenzo[g][1,2,4]triazolo[3,4-a]isoquinolin-3(2H)-one (7-34);
6-(3-aminopropyl)-10-chlorobenzo[g][1,2,4]triazolo[3,4-a]isoquinolin-3(2H)-one (7-35);
6-[(1Z)-3-aminoprop-1-en-1-yl]-9,10-difluorobenzo[g][1,2,4]triazolo[3,4-a]isoquinloin-3(2H)-one (7-36);
6-(3-aminopropyl)-9,10-difluorobenzo[g][1,2,4]triazolo[3,4-a]isoquinolin-3(2H)-one (7-37);
6-(3-aminopropyl)-10-(trifluoromethyl)benzo[g][1,2,4]triazolo[3,4-a]isoquinolin-3(2H)-one (7-38);
6-(3-aminopropyl)-2,6-dihydrobenzo[g][1,2,4]triazolo[4,3-c]quinazoline-3,5-dione (8-8); and
6-(3-aminopropyl)-2,6-dihydrobenzo[g][1,2,4]triazolo[4,3-c]quinazoline-3,5-dione (8-10);
or a stereoisomer thereof.

A further specific compound of the instant invention is the HCl salt:
6-(3-aminopropyl)benzo[g][1,2,4]triazolo[3,4-a]isoquinolin-3(2H)-one (7-10);
or a stereoisomer thereof.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

This invention is also intended to encompass pro-drugs of the compounds disclosed herein. A prodrug of any of the compounds can be made using well known pharmacological techniques.

When any variable (e.g. $R^1$, $R^6$, $R^{6a}$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms.

If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

The term "cycloalkyl" means a monocyclic or bicyclic saturated aliphatic hydrocarbon group having the specified number of carbon atoms. For example, "cycloalkyl" inlcudes cyclopropyl, methyl-cyclopropyl, 2,2-dimethyl-cyclobutyl, 2-ethyl-cyclopentyl, cyclohexyl, and so on.

The term "cycloalkenyl" means a monocyclic or bicyclic partially unsaturated aliphatic hydrocarbon group having the specified number of carbon atoms. For example, "cycloalkenyl" inlcudes cyclopropenyl, methyl-cyclopropenyl, 2,2-dimethyl-cyclobutenyl, 2-ethyl-cyclopentenyl, cyclohexenyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. Attachment of a heteroaryl substituent can occur via a carbon atom or via a heteroatom.

As appreciated by those of skill in the art, "halo" or "halogen" as used herein is intended to include chloro (Cl), fluoro (F), bromo (Br) and iodo (I).

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include: benzoimidazolyl, benzofuranyl, benzofurazanyl, benzopyrazolyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisochromenyl, dihydroisooxazolyl, dihydroisothiazolyl, -dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydroisoquinolinyl, tetrahydroquinolinyl and tetrahydrothienyl, and N-oxides thereof Attachment of a heterocyclyl substituent can occur via a carbon atom or via a heteroatom.

The alkyl, alkenyl, alkynyl, cycloalkyl, aryl, heteroaryl and heterocyclyl substituents may be unsubstituted or unsubstituted, unless specifically defined otherwise. For example, a $(C_1-C_6)$alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —(C═O) $CH_2CH(OH)CH_3$, —(C═O)OH, —$CH_2(OH)CH_2CH(O)$, and so on.

In certain instances, $R^7$ and $R^8$ are defined such that they can be taken together with the nitrogen to which they are attached to form a monocyclic or bicyclic heterocycle with 3-7 members in each ring and optionally containing, in addition to the nitrogen, one or two additional heteroatoms selected from N, O and S, said heterocycle optionally substituted with one or more substituents selected from $R^{6a}$. Examples of the heterocycles that can thus be formed include the following, keeping in mind that the heterocycle is optionally substituted with one or more substituents chosen from $R^{6a}$:

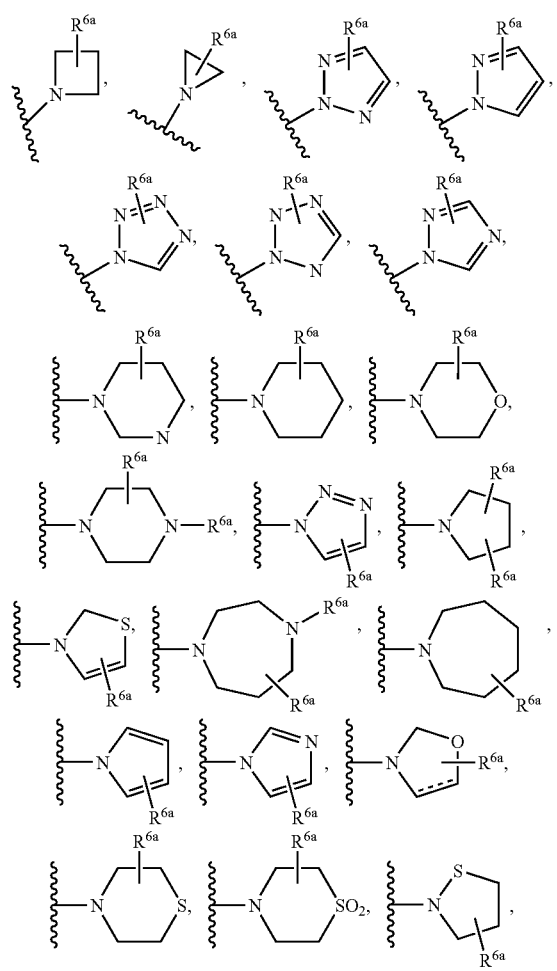

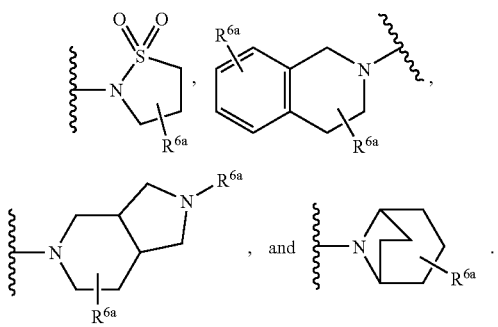

In an embodiment of Formula A, Ring Z is selected from:

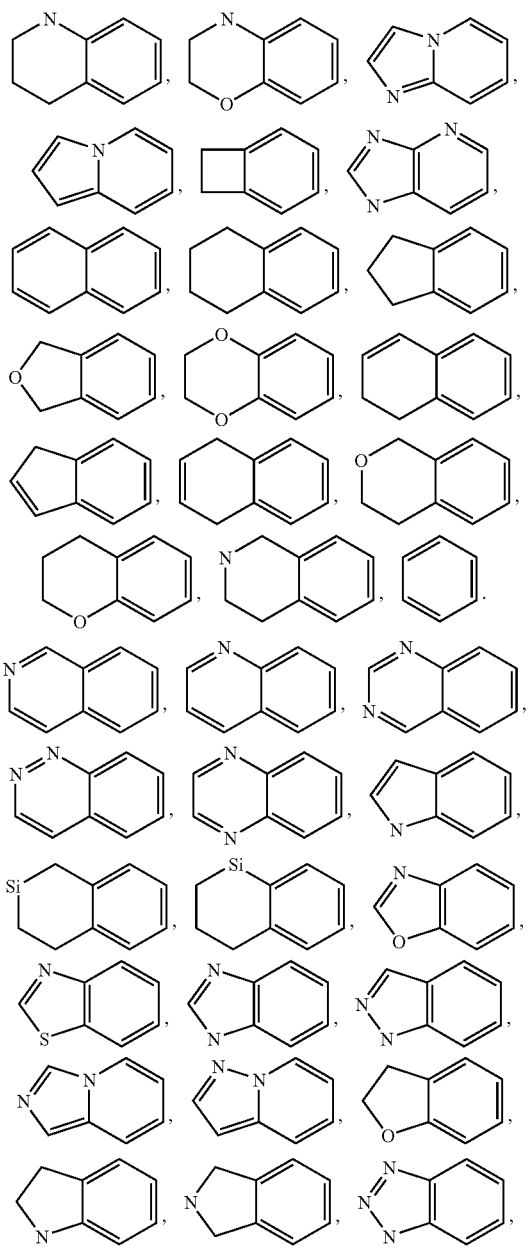

-continued

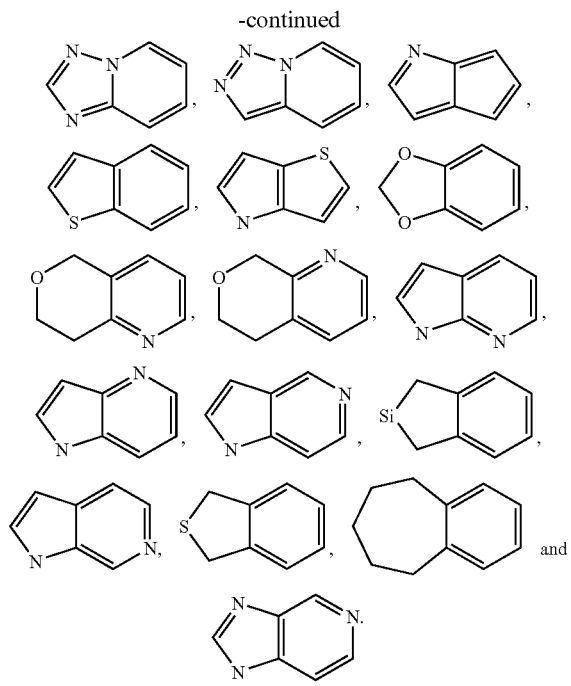

In another embodiment of Formula A, Ring Z is selected from:

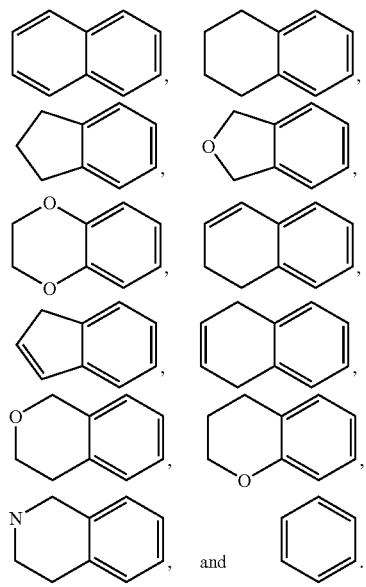

In another embodiment of Formula A, the core molecule including Ring Z is selected from:

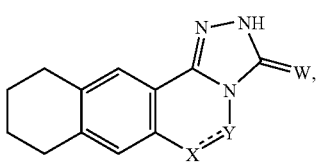

-continued

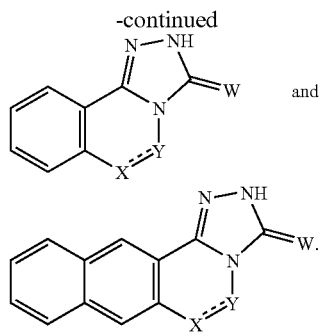

In an embodiment of Formula B, the core molecule including Ring Z is selected from:

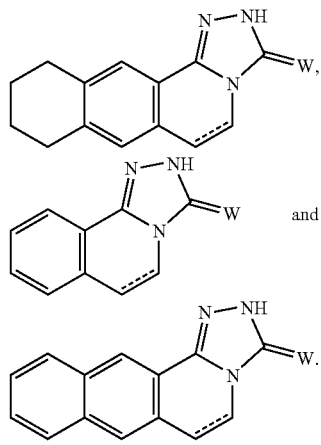

In another embodiment of Formula A or B, n is 0, 1, 2, 3 or 4.

In another embodiment of Formula A or B, n is 0, 1 or 2.

In another embodiment of Formula A or B, n is 1.

In another embodiment of Formula A or B, n is 0.

In another embodiment of Formula A or B, $R^4$ is alkyl, aryl, heterocyclyl or H, said alkyl, aryl and heterocyclyl optionally substituted with from one to three substituents selected from $R^6$.

In another embodiment of Formula A or B, W is O, $R^2$ is selected from: H, $C_1$-$C_6$alkyl, $C_1$-$C_6$alkenyl, aryl, halo, $C_3$-$C_8$cycloalkyl and heterocyclyl, said alkyl, alkenyl, aryl, cycloalkyl, and heterocyclyl is optionally substituted with one to three substituents selected from $R^6$.

In another embodiment of Formula A or B, W is O, $R^1$ is selected from: $(C_2$-$C_5)$—NR'R", said $(C_2$-$C_5)$ is optionally substituted with one to three $R^6$ and said R' and R" are independently selected from: H, (C=O)$O_b$$C_1$-$C_{10}$alkyl, (C=O)$O_b$$C_3$-$C_8$cycloalkyl, (C=O)$O_b$aryl, (C=O)$O_b$heterocyclyl, $C_1$-$C_{10}$alkyl, aryl, $C_2$-$C_{10}$alkenyl, $C_2$-$C_{10}$alkynyl, heterocyclyl, $C_3$-$C_8$cycloalkyl, $SO_m$$R^a$, and (C=O)$_a$$NR^b$2, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula A or B, W is O, $R^1$ is selected from: propyl-NR'R", said propyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$alkyl, aryl, $C_2-C_{10}$alkenyl, $C_2-C_{10}$alkynyl, heterocyclyl, $C_3-C_8$cycloalkyl, $SO_mR_a$, and $(C=O)_aNR_b2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula A or B, W is O, $R^2$ is selected from: H, $C_1-C_6$alkyl, $C_1-C_6$alkenyl, aryl, halo, $C_3-C_8$cycloalkyl and heterocyclyl, said alkyl, alkenyl, aryl, cycloalkyl, and heterocyclyl is optionally substituted with one to three substituents selected from $R^6$; and $R^1$ is selected from: $(C_2-C_5)$alkyl-NR'R", said $(C_2-C_5)$alkyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$ alkyl, aryl, $C_2-C_{10}$alkenyl, $C_2-C_{10}$alkynyl, heterocyclyl, $C_3-C_8$cycloalkyl, $SO_mR^a$, and $(C=O)_aNR^b_2$, said alkyl, cycloalkyl, aryl, heterocylyl, alkenyl, and alkynyl are optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula A or B, W is O, $R^2$ is selected from: aryl, halo, $C_3-C_8$ cycloalkyl and heterocyclyl, said aryl, cycloalkyl, and heterocyclyl is optionally substituted with one to three substituents selected from $(C_1-C_6)$alkyl, OH, $NH_2$, CHO, COOH, halo, oxo, $-O(C_1-C_6)$alkyl, and $(C_1-C_6)$alkyl-OH; and $R^1$ is selected from: $(C_2-C_5)$alkyl-$NH_2$, said $(C_2-C_5)$alkyl is optionally substituted with one or more OH and halo.

In an embodiment of Formula C, n is 0, 1, 2, 3 or 4.
In another embodiment of Formula C, n is 0, 1 or 2.
In another embodiment of Formula C, n is 1.
In another embodiment of Formula C, n is 0.
In another embodiment of Formula C, $R^2$ is selected from: H, $C_1-C_6$alkyl, $C_1-C_6$alkenyl, aryl, halo, $C_3-C_8$cycloalkyl and heterocyclyl, said alkyl, alkenyl, aryl, cycloalkyl, and heterocyclyl is optionally substituted with one to three substituents selected from $R^6$.

In another embodiment of Formula C, $R^1$ is selected from: $(C_2-C_5)$alkyl-NR'R", said $(C_2-C_5)$alkyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$alkyl, aryl, $C_2-C_{10}$alkenyl, $C_2-C_{10}$alkynyl, heterocyclyl, $C_3-C_8$cycloalkyl, $SO_mR^a$, and $(C=O)_aNR^b2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula C, $R^1$ is selected from: propyl-NR'R", said propyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$alkyl, aryl, $C_2-C_{10}$alkenyl, $C_2-C_{10}$alkynyl, heterocyclyl, $C_3-C_8$cycloalkyl, $SO_mR_a$, and $(C=O)_aNR_{b2}$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula C, $R^2$ is selected from: H, $C_1-C_6$alkyl, $C_1-C_6$alkenyl, aryl, halo, $C_3-C_8$cycloalkyl and heterocyclyl, said alkyl, alkenyl, aryl, cycloalkyl, and heterocyclyl is optionally substituted with one to three substituents selected from $R^6$; and $R^1$ is selected from: $(C_2-C_5)$alkyl-NR'R", said $(C_2-C_5)$alkyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$ alkyl, aryl, $C_2-C_{10}$alkenyl, $C_2-C_{10}$alkynyl, heterocyclyl, $C_3-C_8$cycloalkyl, $SO_mR^a$, and $(C=O)_aNR^b_2$, said alkyl, cycloalkyl, aryl, heterocylyl, alkenyl, and alkynyl are optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula C, $R^2$ is selected from: aryl, halo, $C_3-C_8$ cycloalkyl and heterocyclyl, said aryl, cycloalkyl, and heterocyclyl is optionally substituted with one to three substituents selected from $(C_1-C_6)$alkyl, OH, $NH_2$, CHO, COOH, halo, oxo, $-O(C_1-C_6)$alkyl, and $(C_1-C_6)$alkyl-OH; and $R^1$ is selected from: $(C_2-C_5)$alkyl-$NH_2$, said $(C_2-C_5)$alkyl is optionally substituted with one or more OH and halo.

In an embodiment of Formula D, $R^2$ is selected from: aryl, halo, $C_3-C_8$cycloalkyl and heterocyclyl, said aryl, cycloalkyl, and heterocyclyl is optionally substituted with one to three substituents selected from $R^6$.

In another embodiment of Formula D, $R^2$ is selected from: aryl, $C_3-C_8$ cycloalkyl and heterocyclyl, said aryl, cycloalkyl, and heterocyclyl is optionally substituted with one to three substituents selected from $R^6$.

In another embodiment of Formula D, $R^2$ is halo.

In another embodiment of Formula D, $R^1$ is selected from: $(C_2-C_5)$alkyl-NR'R", said $(C_2-C_5)$alkyl is optionally substituted with one to three $R^6$ and said R' and R" are independently selected from: H, $(C=O)O_bC_1-C_{10}$alkyl, $(C=O)O_bC_3-C_8$cycloalkyl, $(C=O)O_b$aryl, $(C=O)O_b$heterocyclyl, $C_1-C_{10}$alkyl, aryl, $C_2-C_{10}$alkenyl, $C_2-C_{10}$alkynyl, heterocyclyl, $C_3-C_8$cycloalkyl, $SO_mR^a$, and $(C=O)_aNR^b_2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula D, $R^1$ is selected from: propyl-NR'R", said propyl is optionally substituted with one to three $R^6$ and said R' and R" are independently selected from: H, $(C=O)O_bC_1$-$C_{10}$alkyl, $(C=O)O_bC_3$-$C_8$cycloalkyl, $(C=O)O_b$aryl, $(C=O)O_b$heterocyclyl, $C_1$-$C_{10}$alkyl, aryl, $C_2$-$C_{10}$alkenyl, $C_2$-$C_{10}$alkynyl, heterocyclyl, $C_3$-$C_8$cycloalkyl, $SO_mR^a$, and $(C=O)_aNR^b{}_2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula D, $R^2$ is selected from: H, $C_1$-$C_6$alkyl, $C_1$-$C_6$alkenyl, aryl, halo, $C_3$-$C_8$cycloalkyl and heterocyclyl, said alkyl, alkenyl, aryl, cycloalkyl, and heterocyclyl is optionally substituted with one to three substituents selected from $R^6$; and $R^1$ is selected from: $(C_2$-$C_5)$alkyl-NR'R", said $(C_2$-$C_5)$alkyl is optionally substituted with one to three $R^6$ and said R' and R" are independently selected from: H, $(C=O)O_bC_1$-$C_{10}$alkyl, $(C=O)O_bC_3$-$C_8$cycloalkyl, $(C=O)O_b$aryl, $(C=O)O_b$heterocyclyl, $C_1$-$C_{10}$ alkyl, aryl, $C_2$-$C_{10}$alkenyl, $C_2$-$C_{10}$alkynyl, heterocyclyl, $C_3$-$C_8$cycloalkyl, $SO_mR^a$, and $(C=O)_aNR^b{}_2$, said alkyl, cycloalkyl, aryl, heterocylyl, alkenyl, and alkynyl are optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula D, $R^2$ is selected from: aryl, halo, $C_3$-$C_8$ cycloalkyl and heterocyclyl, said aryl, cycloalkyl, and heterocyclyl is optionally substituted with one to three substituents selected from $(C_1$-$C_6)$alkyl, OH, $NH_2$, CHO, COOH, halo, oxo, —$O(C_1$-$C_6)$alkyl, and $(C_1$-$C_6)$ alkyl-OH; and $R^1$ is selected from: $(C_2$-$C_5)$alkyl-$NH_2$, said $(C_2$-$C_5)$alkyl is optionally substituted with one or more OH and halo.

In another embodiment of Formula D, n is 0, 1, or 2; $R^2$ is selected from: heterocyclyl, halogen, $(C_1$-$C^6)$alkyl, $CF_3$, $(C_2$-$C_6)$alkenyl, and aryl, said heterocyclyl, alkenyl, aryl, are optionally substituted with one to three substituents selected from, $(C_1$-$C_6)$alkyl, $NH_2$, halogen, —$O(C_1$-$C_6)$alkyl, heterocyclyl, and —$(C_1$-$C_6)$alkyl-$NH_2$; $R^1$is selected from: H, —$O(C_1$-$C_6)$alkyl, $(C_1$-$C_6)$alkyl, halogen, $(C_2$-$C_6)$alkenyl, heterocyclyl, and aryl, said alkyl, alkenyl, heterocyclyl and aryl are optionally substituted with from one to three substituents selected from, halogen, —$(C_1$-$C_6)$alkyl-$NH_2$, —$(C_1$-$C_6)$ alkyl-heterocyclyl, —$N(R^b)_2$—$CF_3$, $N(R^b)_2$, OH, —NH—$(C=O)CF_3$, and —NH—$(C=O)O(C_1$-$C_6)$alkyl; $R^b$ is independently selected from, H and $(C_1$-$C_6)$alkyl.

In another embodiment of Formula E, $R^1$ is selected from: $(C_2$-$C_5)$alkyl-NR'R", said $(C_2$-$C_5)$alkyl is optionally substituted with one to three $R^6$ and said R' and R" are independently selected from: H, $(C=O)O_bC_1$-$C_{10}$alkyl, $(C=O)O_bC_3$-$C_8$cycloalkyl, $(C=O)O_b$aryl, $(C=O)O_b$heterocyclyl, $C_1$-$C_{10}$alkyl, aryl, $C_2$-$C_{10}$alkenyl, $C_2$-$C_{10}$alkynyl, heterocyclyl, $C_3$-$C_8$cycloalkyl, $SO_mR^a$, and $(C=O)_aNR^b{}_2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula E, $R^1$ is selected from: propyl-NR'R", said propyl is optionally substituted with one to three $R^6$ and said R' and R" are independently selected from: H, $(C=O)O_bC_1$-$C_{10}$alkyl, $(C=O)O_bC_3$-$C_8$cycloalkyl, $(C=O)O_b$aryl, $(C=O)O_b$heterocyclyl, $C_1$-$C_{10}$alkyl, aryl, $C_2$-$C_{10}$alkenyl, $C_2$-$C_{10}$alkynyl, heterocyclyl, $C_3$-$C_8$cycloalkyl, $SO_mR^a$, and $(C=O)_aNR^b{}_2$, said alkyl, cycloalkyl, aryl, heterocylyl, alkenyl, and alkynyl is optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula E, $R^2$ is selected from: H, $C_1$-$C_6$alkyl, $C_1$-$C_6$alkenyl, aryl, halo, $C_3$-$C_8$cycloalkyl and heterocyclyl, said alkyl, alkenyl, aryl, cycloalkyl, and heterocyclyl is optionally substituted with one to three substituents selected from $R^6$; and $R^1$ is selected from: $(C_2$-$C_5)$alkyl-NR'R", said $(C_2$-$C_5)$alkyl is optionally substituted with one to three $R^6$ and said R' and R" are independently selected from: H, $(C=O)O_bC_1$-$C_{10}$alkyl, $(C=O)O_bC_3$-$C_8$cycloalkyl, $(C=O)O_b$aryl, $(C=O)O_b$heterocyclyl, $C_1$-$C_{10}$ alkyl, aryl, $C_2$-$C_{10}$alkenyl, $C_2$-$C_{10}$alkynyl, heterocyclyl, $C_3$-$C_8$cycloalkyl, $SO_mR^a$, and $(C=O)_aNR^b{}_2$, said alkyl, cycloalkyl, aryl, heterocylyl, alkenyl, and alkynyl are optionally substituted with one to three substituents selected from $R^{6a}$, or R' and R" can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R^{6a}$.

In another embodiment of Formula E, n is 0, 1, or 2; $R^2$ is selected from: heterocyclyl, halogen, $(C_1$-$C_6)$alkyl, $CF_3$, $(C_2$-$C_6)$alkenyl, and aryl, said heterocyclyl, alkenyl, aryl, are optionally substituted with one to three substituents selected from, $(C_1$-$C_6)$alkyl, $NH_2$, halogen, —$O(C_1$-$C_6)$alkyl, heterocyclyl, and —$(C_1$-$C_6)$alkyl-$NH_2$; $R^1$ is selected from: H, —$O(C_1$-$C_6)$alkyl, $(C_1$-$C_6)$alkyl, halogen, $(C_2$-$C_6)$alkenyl, heterocyclyl, and aryl, said alkyl, alkenyl, heterocyclyl and aryl are optionally substituted with from one to three substituents selected from, halogen, —$(C_1$-$C_6)$alkyl-$NH_2$, —$(C_1$-$C_6)$ alkyl-heterocyclyl, —$N(R^b)_2$—$CF_3$, $N(R^b)_2$, OH, —NH—$(C=O)CF_3$, and —NH—$(C=O)O(C_1$-$C_6)$alkyl; $R^b$ is independently selected from, H and $(C_1$-$C_6)$alkyl.

In another embodiment of Formula E, $R^2$ is selected from: aryl, halo, $C_3$-$C_8$ cycloalkyl and heterocyclyl, said aryl, cycloalkyl, and heterocyclyl is optionally substituted with one to three substituents selected from $(C_1$-$C_6)$alkyl, OH, $NH_2$, CHO, COOH, halo, oxo, —$O(C_1$-$C_6)$alkyl, and $(C_1$-$C_6)$ alkyl-OH; and $R^1$ is selected from: $(C_2$-$C_5)$alkyl-$NH_2$, said $(C_2$-$C_5)$alkyl is optionally substituted with one or more OH and halo.

In another embodiment of Formula E, n is 0, 1 or 2; $R^2$ is selected from: $(C_1-C_6)$alkyl, $CF_3$ and halo; and $R^1$ is selected from: $(C_2-C_5)$alkyl-$NH_2$, said $(C_2-C_5)$alkyl is optionally substituted with one or more OH and halo.

In another embodiment of Formula E, n is 0, 1 or 2; $R^2$ is selected from: $(C_1-C_6)$alkyl, $CF_3$ and halo; and $R^1$ is propylamine.

In another embodiment of Formula E, n is 0; and $R^1$ is selected from: $(C_2-C_5)$alkyl-$NH_2$, said $(C_2-C_5)$alkyl is optionally substituted with one to three OH and halo.

Included in the instant invention is the free form of compounds of Formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,$N^1$-dibenzylethylenediamine, diethylamin, 2-diethylaminoethanol, 2-dimethylaaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, brain, testicular, stomach, ovarian, pancrease, skin, small intestine, large intestine, throat, head and neck, oral, bone, liver, bladder, kidney, thyroid and blood.

Cancers that may be treated by the compounds, compositions and methods of the invention include: ovarian, breast, colorectal, lung (non-small cell), pancreas, esophageal, gastric and head and neck.

Cancers that may be treated by the compounds, compositions and methods of the invention include: breast, prostate, colon, ovarian, colorectal and lung.

Cancers that may be treated by the compounds, compositions and methods of the invention include: breast, colon, (colorectal) and lung.

Cancers that may be treated by the compounds, compositions and methods of the invention include: lymphoma and leukemia.

Ovarian cancer may be treated by the compounds, compositions and methods of the invention.

Breast cancer may be treated by the compounds, compositions and methods of the invention.

Colorectal cancer may be treated by the compounds, compositions and methods of the invention.

Lung (non-small cell) cancer may be treated by the compounds, compositions and methods of the invention.

Pancreas cancer may be treated by the compounds, compositions and methods of the invention.

Esophageal cancer may be treated by the compounds, compositions and methods of the invention.

Gastric cancer may be treated by the compounds, compositions and methods of the invention.

Head and neck cancer may be treated by the compounds, compositions and methods of the invention.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For example, a 50 mg/mL formulation of compounds of the instant invention may be prepared according to the following procedure: 1. Weigh out 5.6 g of a compound of the instant invention and 5.0 g of mannitol; 2. Tare a glass vessel (prefer 250 mL beaker) on the balance, and add about 85 mL water to the vessel; 3. Add a magnetic stirring bar to the vessel and stir at a speed sufficient to create a vortex; 4. Add 0.42 mL L-Lactic Acid to the vessel; 5. Add 5 g mannitol to the vessel and mix for 10 minutes; 6. Add a compound of the instant invention, rinsing the container with solution to recover residual compound; 7. Stir for at least 15 minutes, or until there are no visible solids in the solution; 8. Measure the pH of the solution. Add 1N NaOH solution until the pH reaches the range 3.4-6.4 (expect about 2 mL will be required); 9. Add additional water to target weight and mix for 10 additional minutes; 10. Confirm pH is within 3.0-4.0 range; and 11. Sterile-filter solution using bottle-top filter apparatus.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

Compounds of the instant invention could be administered once every three weeks or weekly two-times every three weeks or weekly for each week of a 3 week cycle. Compounds of the instant invention could be administered in a dose range of 54-2160 mg/m$^2$/day. Compounds could be administered orally or IV. IV dosing could potentially occur over 2-24 hours.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter refered to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-k1]acridine-2-(6H)propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL33 1, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methlenedioxy)-5-methyl-7-hydroxy-8-methoxybenzo [c]-phenanthridinium, 6,9-bis[(2-aminoethyl)amino]benzo [g]isoguinoline-5,10-dione, 5-(3-aminopropylamino)-7,10-dihydroxy-2-(2-hydroxyethylaminomethyl)-6H-pyrazolo[4, 5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP 1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbanoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin n antagonists (see Fernandez et al., J. Lab. Clin. Med. 105:141-145 (1985)), and antibodies to VEGF (see, Nature Biotechnology, Vol. 17, pp.963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. No. 60/310,927 (filed Aug. 8, 2001) and Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1, CHK2 and Wee-1 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, Ser. Nos. 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, ARCOXIA®, BEXTRA® and CELEBREX® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-i-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\epsilon_8$, $\alpha_1\beta_1$, $\alpha_2\beta_1$, $\alpha_5\beta_1$, $\alpha_v\beta_5$, and $\alpha_6\beta_4$ integrins. The term also refers to antagonists of any combination of $\alpha_v\beta_3$, $\alpha_v\beta_5$, $\alpha_v\beta_6$, $\alpha_1\beta_1$, $\alpha_2\beta_1$, $\alpha_5\beta_1$, $\alpha_5\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999;274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 11 9:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998;5(8):1105-13), and interferon gamma (*J. Immunol.* 2000;164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifedepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating or preventing cancer in combination with carboplatin and taxol.

A compound of the instant invention may also be useful for treating or preventing cancer in combination with 5-FU and cisplatin.

A compound of the instant invention may also be useful for treating or preventing cancer in combination with capecitabine.

A compound of the instant invention may also be useful for treating or preventing cancer in combination with oxaliplatin.

A compound of the instant invention may also be useful for treating or preventing cancer in combination with cisplatin.

A compound of the instant invention may also be useful for treating or preventing cancer in combination with gemcitabine.

A compound of the instant invention may also be useful for treating or preventing cancer in combination with radiotherapy.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE(®); DROMOSTANOLONE PROPIONATE (MASTERONE INJECTION®); Elliott's B Solution (Elliott's B Solution®); epirubicin (Ellence®); Epoetin alfa (epogen®); erlotinib (Tarceva®); estramustine (Emcyt®); etoposide phosphate (Etopophos®)); etoposide, VP-16 (Vepesid®)); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan(®); sargramostim (Leukine(®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine(®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin(®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®); and vorinostat (Zolinza®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

All patents, publications and pending patent applications identified are hereby incorporated by reference.

Abbreviations that may be used in the description of the chemistry and in the Schemes that follow are: $Ac_2O$ (acetic anhydride); AcOH (acetic acid); AEBSF (p-aminoethylbenzenesulfonyl fluoride); BSA (bovine serum albumin); BuLi (n-Butyl lithium); $CDCl_3$ (chloroform-d); CuI (copper iodide); $CuSO_4$ (copper sulfate); DBU (1,8-diazabicyclo[5.4.0]undec-7-ene); DCE (dichloroethane); DCM (dichloromethane); DEAD (diethyl azodicarboxylate); DIPEA (diisopropylethylamine); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); $Et_2O$ (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); $MP-B(CN)H_3$ (Macroporous cyanoborohydride); $NaHCO_3$ (sodium bicarbonate); $Na_2SO_4$ (sodium sulfate); $Na(OAc)_3BH$ (sodium triacetoxyborohydride); $NH_4OAc$ (ammonium acetate); NBS (N-bromosuccinamide); NMP (1-methyl-2-pyrrolidinone); NMR (nuclear magnetic resonance); PBS (phosphate buffered saline); PCR (polymerase chain reaction); Pd(dppf) ([1,1'-bis(diphenylphosphino)ferrocene]palladium); $Pd(Ph_3)_4$ (palladium(0) tetrakis-triphenylphosphine); $POCl_3$ (phosphorous oxychloride); PS-DIEA (polystyrene diisopropylethylamine); $PS-PPh_3$ (polystyrene-triphenyl phosphine); PTSA (para-toluene sulfonic acid); Pyr (pyridine); Selectfluor (1-chloromethyl-4-fluoro-1,4-diazoniabicyclo[2.2.2]octane bis(tetrafluoroborate); RP HPLC (reverse phase high-performance liquid chromatography); TBAF (tetrabutylammonium fluoride); t-BuOH (tert-butanol); THF (tetrahydrofuran); Tf (trifluoromethanesulfonyl); TFA (trifluoroacteic acid); and $TMSCH_2N_2$ (trimethylsilyldiazomethane).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula A hereinabove.

Reactions used to generate the compounds of this invention are prepared by employing reactions as shown in Reaction Schemes I-VII.

Synopsis of Reaction Schemes

As shown in Reaction Scheme I, the substituted 1-chloroisoquinolines (A-1) can undergo a microwave-assisted cyclization with ethyl carbazate to provide triazoloisoquinoline (A-2). When $R_2$=halogen, compounds A-2 can be further derivatized by coupling with heterocyclic boronic acid/esters via Suzuki coupling reaction to furnish compounds denoted by A-3.

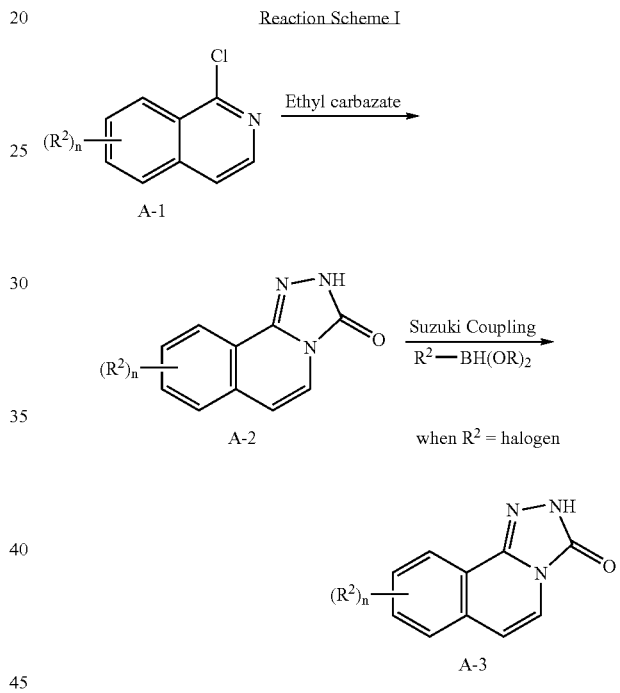

Reaction Scheme II illustrates the preparation of aminoethers (B-3) by alkylation of substituted 4-hydroxyisoqinolines (B-1) with corresponding Boc or phthalimide protected bromoamines (B-2). Ethers B-3 then undergo microwave-assisted cyclization with ethyl carbazate, and corresponding deprotection reaction to afford triazoloquinolines B-4.

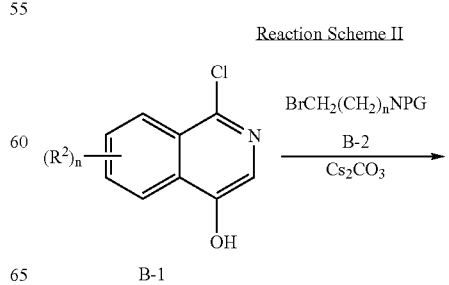

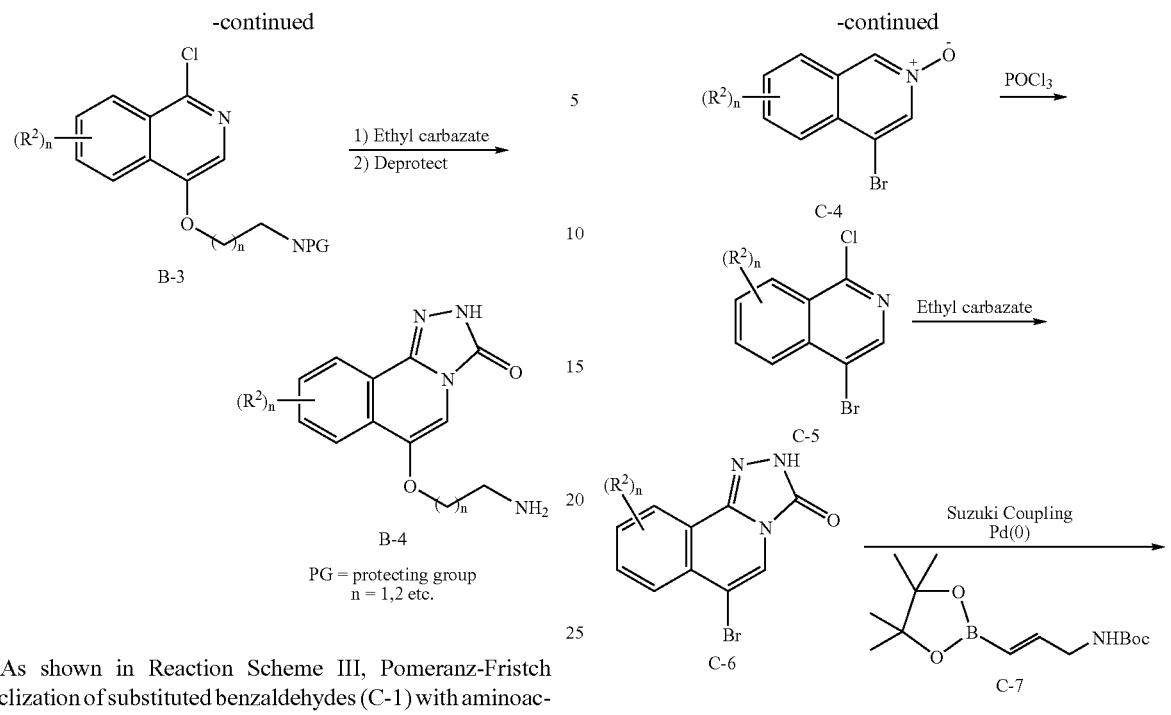

As shown in Reaction Scheme III, Pomeranz-Fristch cyclization of substituted benzaldehydes (C-1) with aminoacetaldehyde dimethyl acetal can afford substituted isoquinolines (C-2) (sometimes as isomeric mixture). Selective bromination can furnish their 4-bromo derivatives (C-3), which can be transformed to N-oxides (C-4) using mCPBA. Compound C-4 can undergo regio-selective rearrangement when treated with POCl$_3$ to provide substituted 1-chloroisoquinolines (C-5), which can undergo microwave-assisted cyclization to form the bromotriazoloisoquinolines (C-6). Suzuki coupling of compounds C-6 with boronic ester (C-7) can afford compounds denoted by C-8. Further hydrogenation/de-protection can furnish the corresponding C-9 and C-11 derivatives.

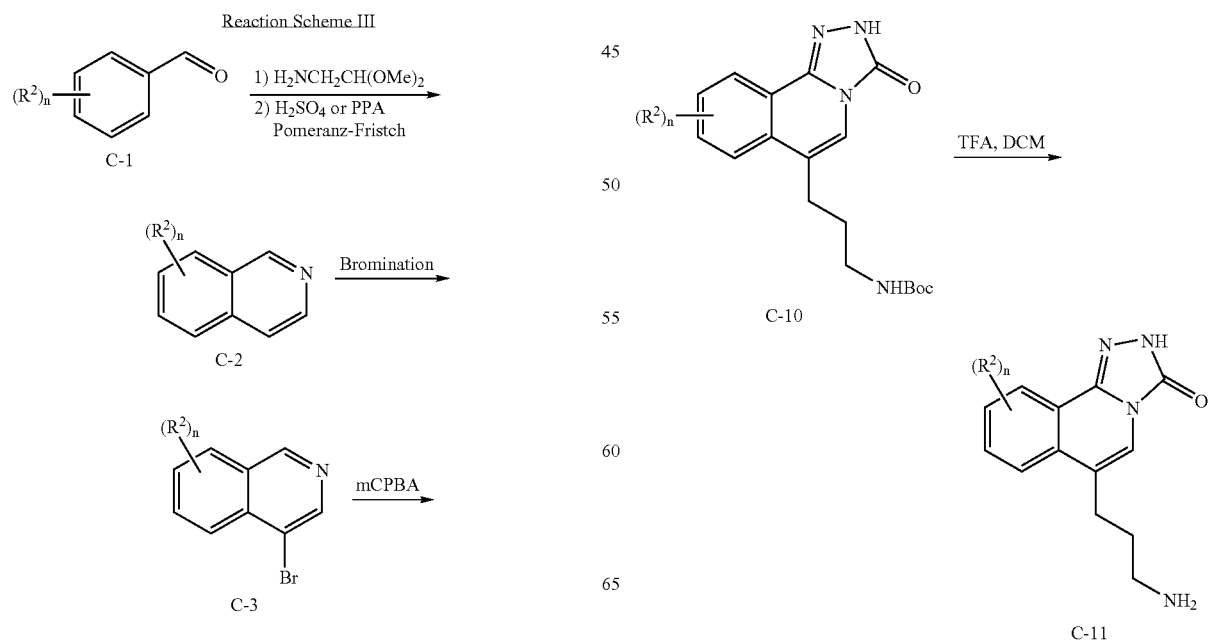

When bromide C-3 is an optionally substituted azaanthracene C-3a, an alternative route can be used (Reaction Scheme IIIa). Addition of a substituted zinc bromide to an acylated pyridine carboxaldehyde formed in situ from C-1a occurs in 1,4 fashion and leads to corresponding dihydropyridine C-2a, which can be dearomatized and deacylated by the action of sulfur in refluxing decalin. Treatment of the resulting mixture with polyphosphoric acid then yield desired cyclised bromide C-3a.

Reaction Scheme IIIa

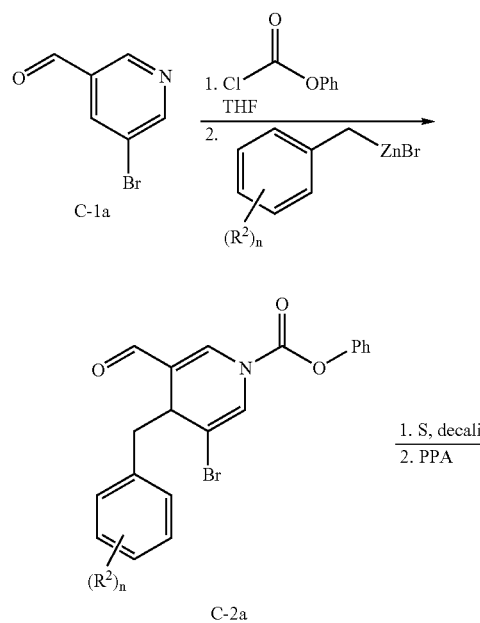

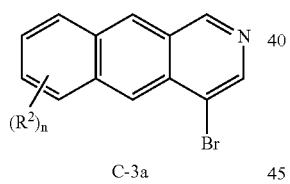

Reaction Scheme IV illustrates that cross-coupling of bromides C-6 with propargyl alcohol can furnish D-1, which can be reduced to D-2.

Reaction Scheme IV

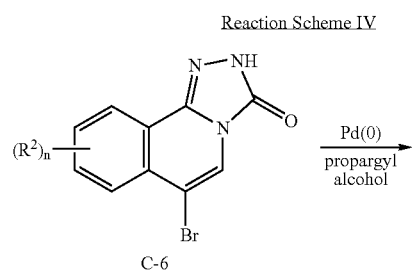

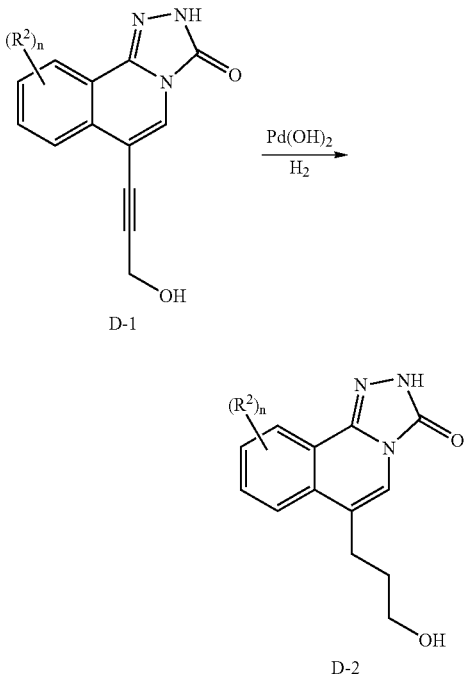

As shown in Reaction Scheme V, N-oxides C-4 can undergo Heck coupling with allyl alcohol to afford aldehydes E-1 which, under reductive amination condition, can form amines E-2. Rearrangement and cyclization steps are then carried out as described in Reaction Scheme III to afford amines E-3.

Reaction Scheme V

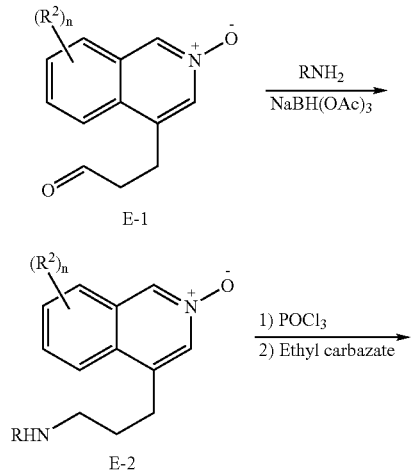

-continued

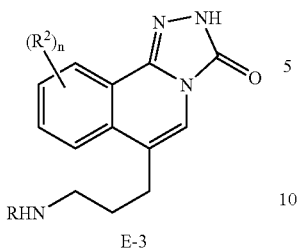
E-3

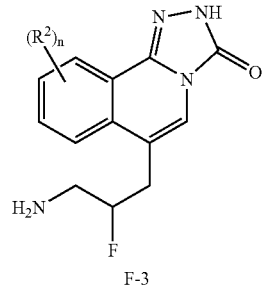
F-3

As shown in Reaction Scheme VI, aldehyde E-1 can undergo α-fluorination using DL-proline as the enamine catalyst and NFSi as the fluorine source. The resulted α-fluoroaldehyde can be trapped with allyl amine under reductive amination conditions, and further protected with Boc group to furnish compounds F-1. Rearrangement and cyclization steps can then proceed as described in Reaction Scheme III to afford compounds denoted by F-2 which, upon treatment with DMBA and catalytic amount of Pd(0), give deprotected amines F-3.

As shown in Reaction Scheme VII, substituted anthranilic acids (G-1) can be cyclized with urea to provide quinazolinones (G-2). Upon treatment with $POCl_3$, G-2 can be chlorinated to provide dichloroquinazolines (G-3). These electrophiles can be reacted with ethyl carbazate to provide compounds of formula G-4 which can be cyclized upon heating in DMF to provide triazoloquinazolinones (G-5). Selective BOC protection can occur on the triazolo nitrogen to give N-BOC-triazoloquinazolinones (G-6) which can allow for alkylation by a variety of bromides in the presence of cesium carbonate to give the N-alkylated compounds (G-7). BOC group deprotection with TFA can give the fully elaborated triazoloquinazolinones (G-8).

Reaction Scheme VI

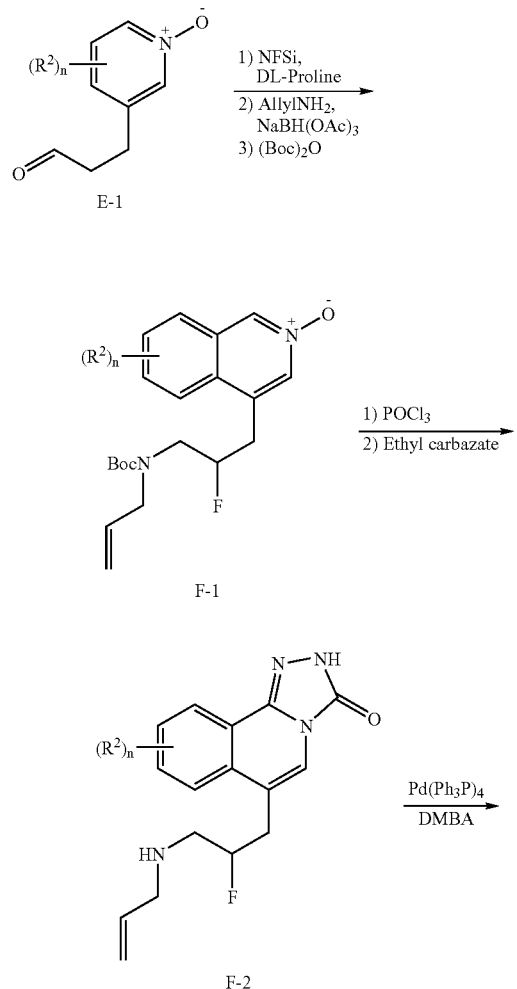

Reaction Scheme VII

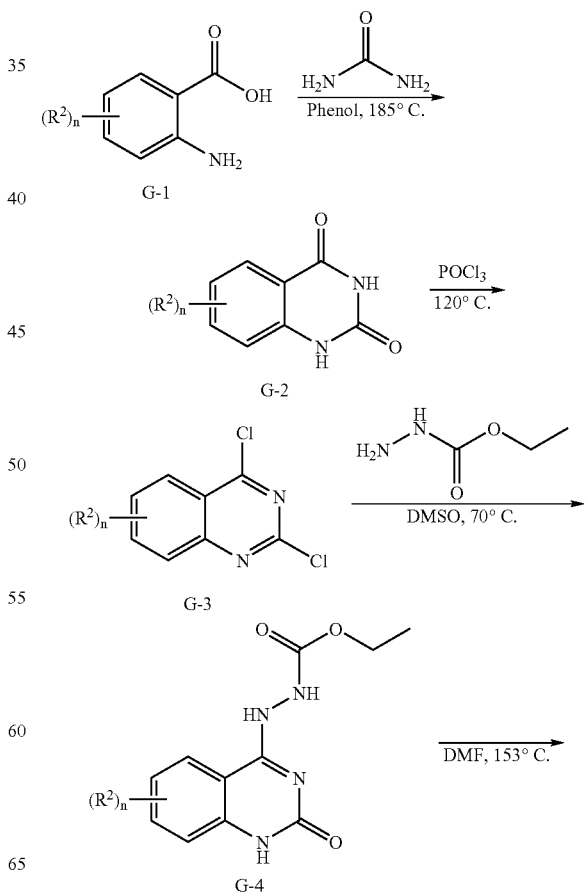

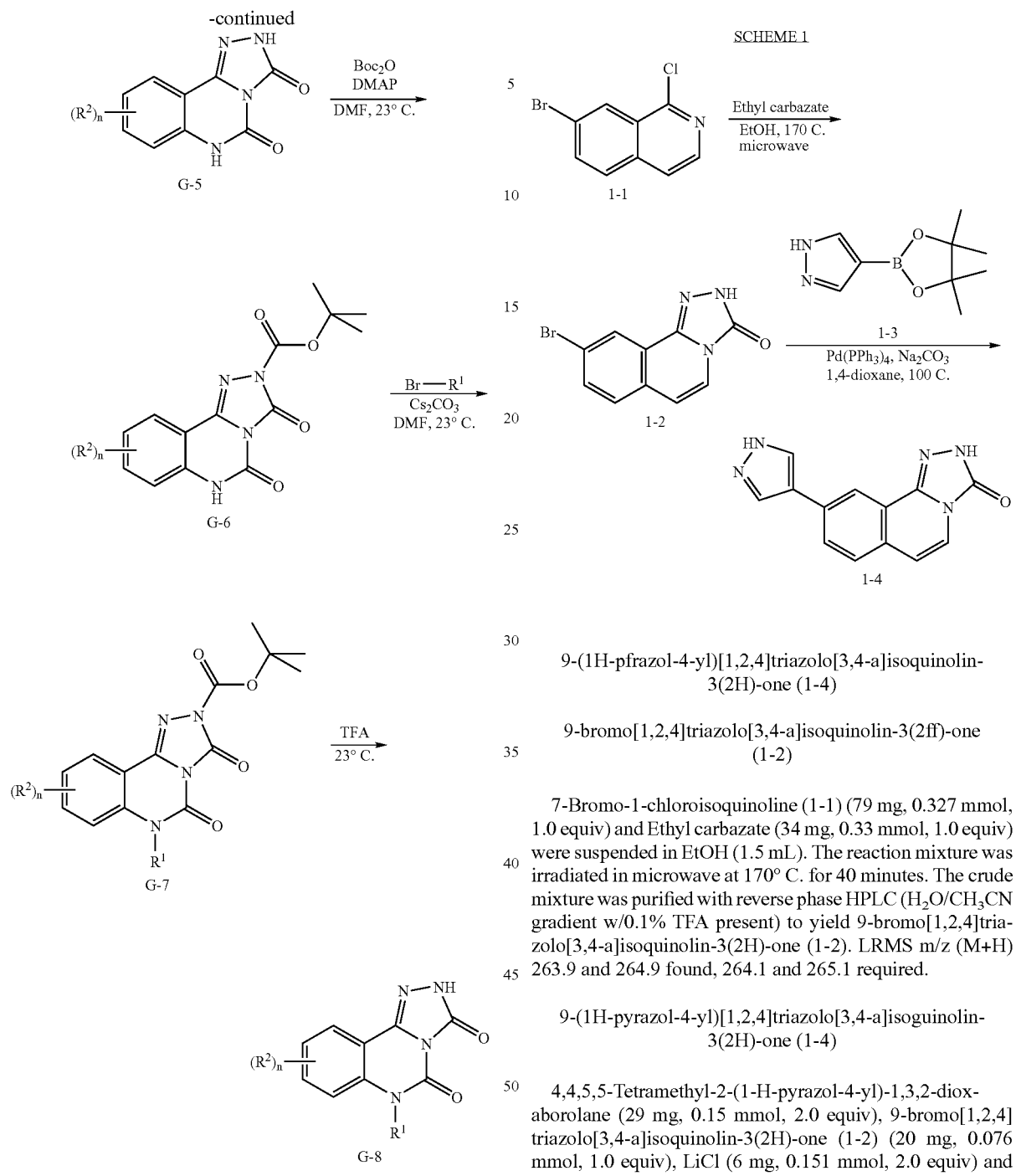

SCHEME 1

9-(1H-pfrazol-4-yl)[1,2,4]triazolo[3,4-a]isoquinolin-3(2H)-one (1-4)

9-bromo[1,2,4]triazolo[3,4-a]isoquinolin-3(2ff)-one (1-2)

7-Bromo-1-chloroisoquinoline (1-1) (79 mg, 0.327 mmol, 1.0 equiv) and Ethyl carbazate (34 mg, 0.33 mmol, 1.0 equiv) were suspended in EtOH (1.5 mL). The reaction mixture was irradiated in microwave at 170° C. for 40 minutes. The crude mixture was purified with reverse phase HPLC ($H_2O/CH_3CN$ gradient w/0.1% TFA present) to yield 9-bromo[1,2,4]triazolo[3,4-a]isoquinolin-3(2H)-one (1-2). LRMS m/z (M+H) 263.9 and 264.9 found, 264.1 and 265.1 required.

9-(1H-pyrazol-4-yl)[1,2,4]triazolo[3,4-a]isoguinolin-3(2H)-one (1-4)

4,4,5,5-Tetramethyl-2-(1-H-pyrazol-4-yl)-1,3,2-dioxaborolane (29 mg, 0.15 mmol, 2.0 equiv), 9-bromo[1,2,4]triazolo[3,4-a]isoquinolin-3(2H)-one (1-2) (20 mg, 0.076 mmol, 1.0 equiv), LiCl (6 mg, 0.151 mmol, 2.0 equiv) and tetrakis(triphenylphosphino)palladium (9 mg, 0.008 mmol, 0.1 equiv) were dissolved in anhydrous 1,4-dioxane (0.5 mL), then treated with 1 M solution of $Na_2CO_3$ in water(0.2 mL). The resulted yellow mixture was heated under $N_2$ at 100° C. overnight. The crude product was purified with reverse phase HPLC ($H_2O/CH_3CN$ gradient w/0.1% TFA present) to afford the pure product (1-4). $^1$H NMR (500 MHz, $CD_3OD$) δ 8.46 (s, 1H), 8.14 (s, 1H), 7.94 (d, 1H, J=8.0 Hz), 7.74 (d, 1H, J=8.0 Hz), 7.58 (d, 1H, J=7.5 Hz), 6.95 (d, 1H, J=7.5 Hz). LRMS m/z (M+H) 252.1 found, 252.1 required.

The compounds shown in Table 1 were synthesized according to the Reaction Scheme 1. The compounds were isolated as TFA salts.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially available or are readily prepared by one of ordinary skill in the art.

TABLE 1

| Cmp | Structure | Name | LRMS m/z (M + H) |
|---|---|---|---|
| 1-5 | 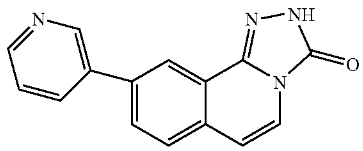 | 9-pyridin-3-yl [1,2,4]triazolo[3,4-α] isoquinolin-3(2H)-one | LRMS m/z (M + H) 263.1 found, 263.1 required. |
| 1-6 | 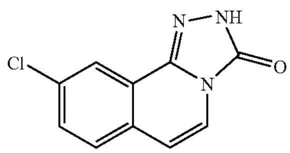 | 9-chloro [1,2,4]triazolo[3,4-α] isoquinolin-3(2H)-one | LRMS m/z (M + H) 220.1 found, 220.0 required. |
| 1-7 | 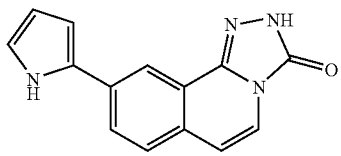 | 9-(1H-pyrrol-2-yl) [1,2,4]triazolo[3,4-a] isoquinolin-3(2H)-one | LRMS m/z (M + H) 250.9 found, 251.1 required. |
| 1-8 | 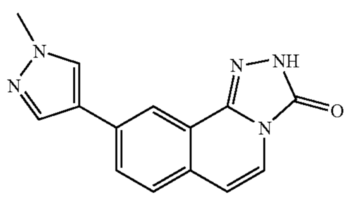 | 9-(1-methyl-1H-pyrazol-4-yl) [1,2,4]triazolo[3,4-a]isoquinolin-3(2H)-one | LRMS m/z (M + H) 266.0 found, 266.1 required. |
| 1-9 | 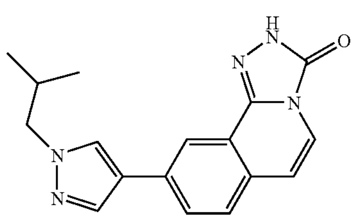 | 9-(1-isobutyl-1H-pyrazol-4-yl) [1,2,4]triazolo[3,4-a] isoquinolin-3(2H)-one | LRMS m/z (M + H) 308.0 found, 308.1 required. |
| 1-10 | 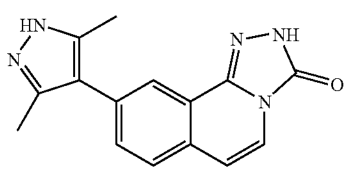 | 9-(3,5-dimethyl-1H-pyrazol-4-yl) [1,2,4]triazolo[3,4-a] isoquinolin-3(2H)-one | LRMS m/z (M + H) 280.0 found, 280.1 required |
| 1-11 | 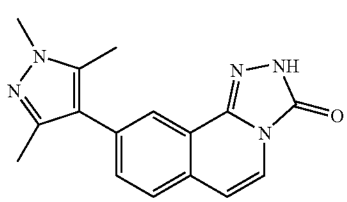 | 9-(1,3,5-trimethyl-1H-pyrazol-4-yl) [1,2,4]triazolo[3,4-a] isoquinolin-3(2H)-one | LRMS m/z (M + H) 294.0 found, 294.1 required. |
| 1-12 | 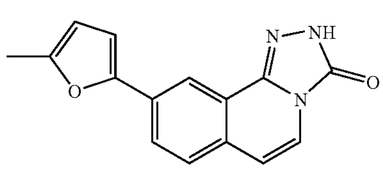 | 9-(5-methyl-2-furyl) [1,2,4]triazolo[3,4-a] isoquinolin-3(2H)-one | LRMS m/z (M + H) 265.9 found, 266.1 required. |

TABLE 1-continued

| Cmp | Structure | Name | LRMS m/z (M + H) |
| --- | --- | --- | --- |
| 1-13 | 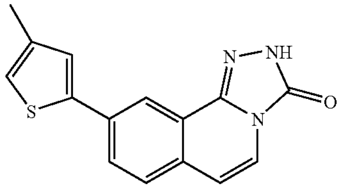 | 9-(4-methyl-2-thienyl) [1,2,4]triazolo[3,4-α] isoquinolin-3(2H)-one | LRMS m/z (M + H) 281.9 found, 282.1 required. |
| 1-14 | 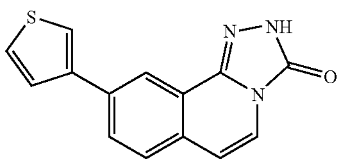 | 9-(3-thienyl) [1,2,4]triazolo[3,4-α] isoquinolin-3(2H)-one | LRMS m/z (M + H) 267.9 found, 268.1 required. |
| 1-15 | 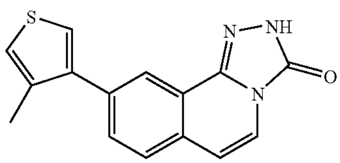 | 9-(4-methyl-3-thienyl) [1,2,4]triazolo[3,4-α] isoquinolin-3(2H)-one | LRMS m/z (M + H) 281.9 found, 282.1 required. |
| 1-16 | 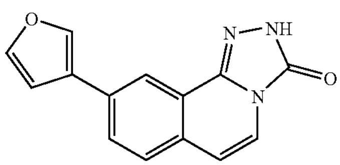 | 9-(3-furyl) [1,2,4]triazolo[3,4-α] isoquinolin-3(2H)-one | LRMS m/z (M + H) 251.9 found, 252.1 required. |
| 1-17 | 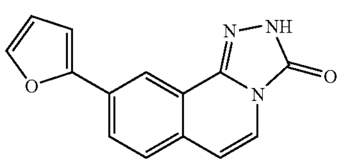 | 9-(2-furyl) [1,2,4]triazolo[3,4-α] isoquinolin-3(2H)-one | LRMS m/z (M + H) 251.9 found, 252.1 required. |
| 1-18 | 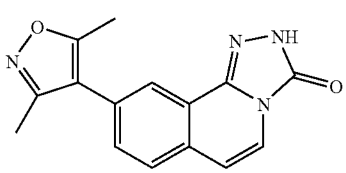 | 9-(3,5-dimethylisoxazol-4-yl) [1,2,4]triazolo[3,4-α]isoquinolin-3(2H)-one | LRMS m/z (M + H) 281.0 found, 281.1 required. |
| 1-19 | 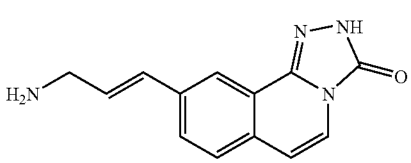 | 9-[(1E)-3-aminoprop-1-en-1-yl] [1,2,4]triazolo[3,4-α] isoquinolin-3(2H)-one | LRMS m/z (M + H) 241.0 found, 241.1 required. |
| 1-20 | 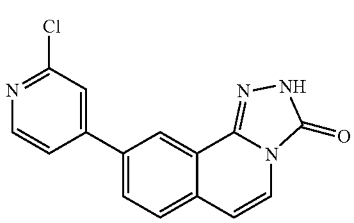 | 9-(2-chloropyridin-4-yl) [1,2,4]triazolo[3,4-α] isoquinolin-3(2H)-one | LRMS m/z (M + H) 296.9 found, 297.1 required. |

TABLE 1-continued

| Cmp | Structure | Name | LRMS m/z (M + H) |
|---|---|---|---|
| 1-21 | 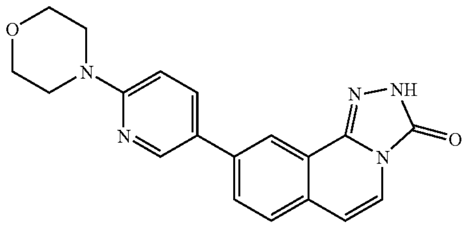 | 9-(6-morpholin-4-ylpyridin-3-yl) [1,2,4]triazolo[3,4-α] isoquinolin-3(2H)-one | LRMS m/z (M + H) 348.0 found, 348.1 required. |
| 1-22 | 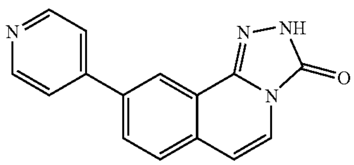 | 9-pyridin-4-yl [1,2,4]triazolo[3,4-α] isoquinolin-3(2H)-one | LRMS m/z (M + H) 263.0 found, 263.1 required. |
| 1-23 | 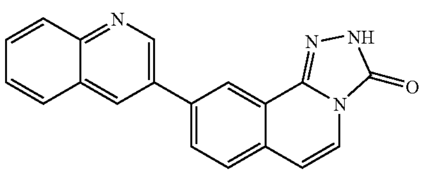 | 9-quinolin-3-yl [1,2,4]triazolo[3,4-α] isoquinolin-3(2H)-one | LRMS m/z (M + H) 313.9 found, 313.1 required. |
| 1-24 | 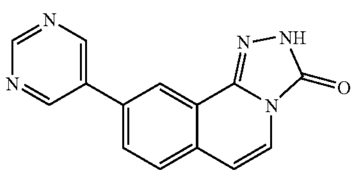 | 9-pyrimidin-5-yl [1,2,4]triazolo[3,4-α] isoquinolin-3(2H)-one | LRMS m/z (M + H) 264.0 found, 264.1 required. |
| 1-25 | 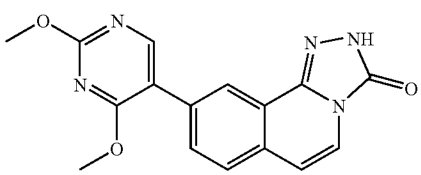 | 9-(2,4-dimethoxypyrimidin-5-yl) [1,2,4]triazolo[3,4-α] isoquinolin-3(2H)-one | LRMS m/z (M + H) 323.9 found, 324.1 required. |
| 1-26 | 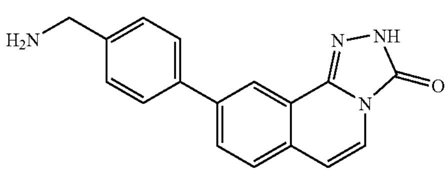 | 9-[4-(aminomethyl)phenyl] [1,2,4]triazolo[3,4-α] isoquinolin-3(2H)-one | LRMS m/z (M + H) 291.0 found, 291.1 required. |

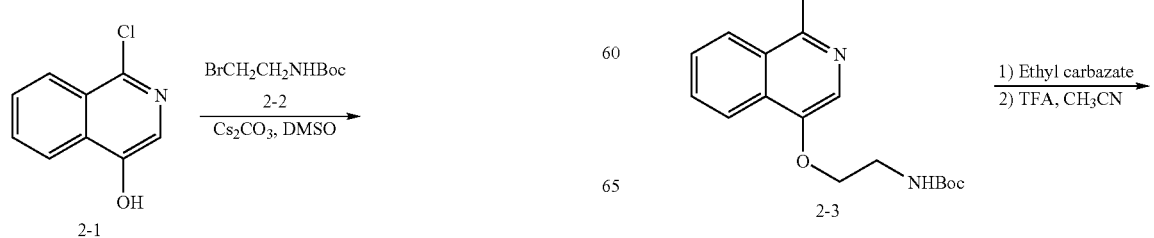

SCHEME 2

-continued

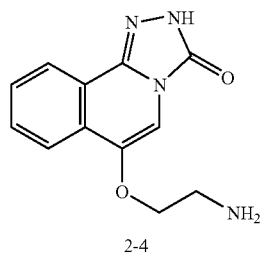

2-4

6-(2-aminoethoxy)[1,2,4]triazolo[3,4-a]isoguinolin-3 (2H)-one (2-4)

tert-butyl 2-[(1-chloroisoquinolin-4-yl)oxy]ethylcarbamate (2-3)

1-chloro-4-hydroxyisoquinoline (50 mg, 0.28 mmol, 1.0 equiv), $Cs_2CO_3$ (454 mg, 1.39 mmol, 5.0 equiv.), and tert-butyl (2-bromoethyl)carbamate (2-2) (94 mg, 0.42 mmol, 1.5 equiv.) were suspended in anhydrous DMSO (2 mL) and stirred at room temperature. When LCMS indicated the reaction was complete, the crude reaction mixture was purified with reverse phase HPLC ($H_2O/CH_3CN$ gradient w/0.1% TFA present) to yield the product (2-3). LRMS m/z (M+H) 323.1 found, 323.1 required.

6-(2-aminoethoxy)[1,2,4]triazolo[3,4-a]isoguinolin-3 (2H)-one (2-4)

tert-butyl 2-[(1-chloroisoquinolin-4-yl)oxy]ethylcarbamate (2-3) (10 mg, 0.031 mmol, 1.0 equiv.) and ethyl carbazate (16 mg, 0.155 mmol, 5.0 equiv.) were suspended in EtOH (1.5 mL) and then irradiated in microwave at 170° C. Once LCMS showed reaction was almost complete, the reaction mixture was diluted with DMSO, filtered, and purified with reverse phase HPLC ($H_2O/CH_3CN$ gradient w/0.1% TFA present) to yield the product. The pure fractions were irradiated in microwave at 150° C. for 5 minutes to remove the Boc protecting group and afford the product (2-4). $^1$H NMR (500 MHz, $CD_3OD$) δ 8.29 (d, 1H, J=8.0 Hz), 8.24 (d, 1H, J=8.0 Hz), 7.77 (t, 1H, J=7.0 Hz), 7.72 (t, 1H, J=7.0 Hz), 7.26 (s, 1H), 4.39 (t, 2H, J=4.9 Hz), 3.54 (t, 2H, J=4.9 Hz). LRMS m/z (M+H) 245.1 found, 245.1 required.

The compound shown in Table 2 was synthesized according to the Reaction Scheme 2. The compound was isolated as a TFA salt.

TABLE 2

| Cmp | Structure | Name | LRMS m/z (M + H) |
| --- | --- | --- | --- |
| 2-5 | 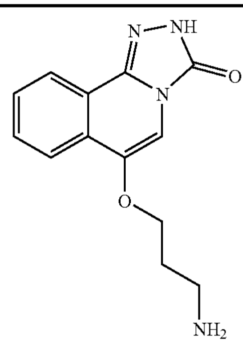 | 6-(3-aminopropoxy)[1,2,4]triazolo[3,4-α]isoquinolin-3(2H)-one | LRMS m/z (M + H) 259.1 found, 259.1 required. |

SCHEME 3

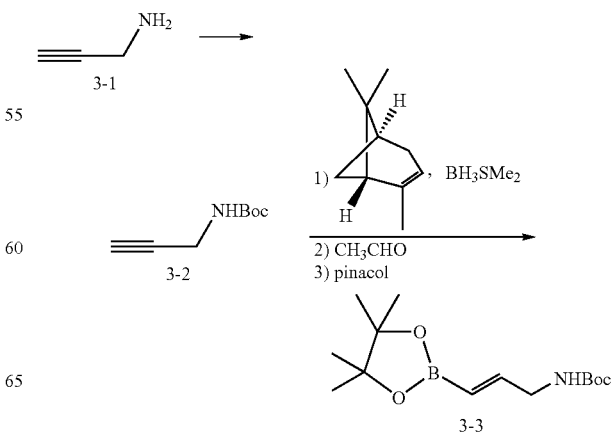

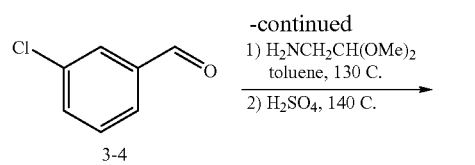

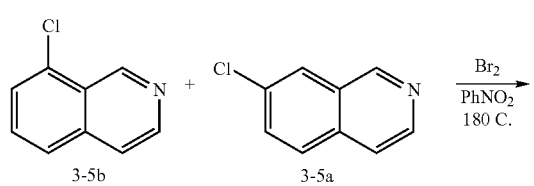

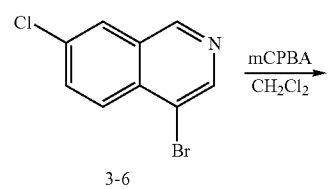

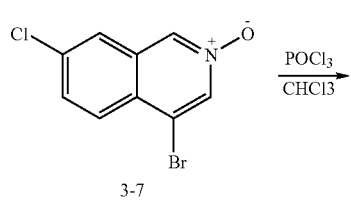

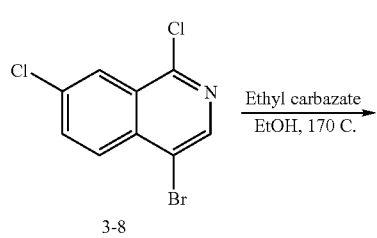

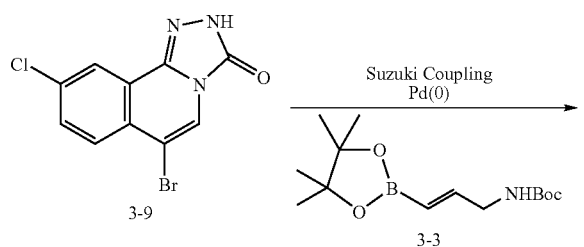

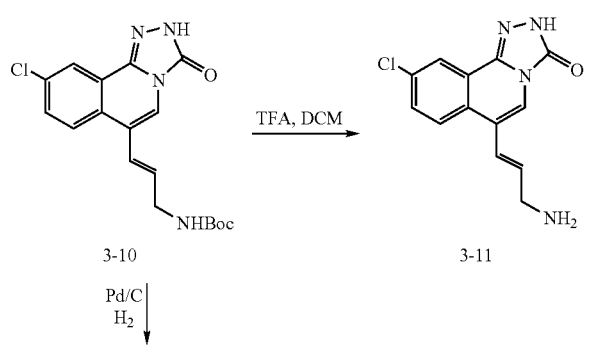

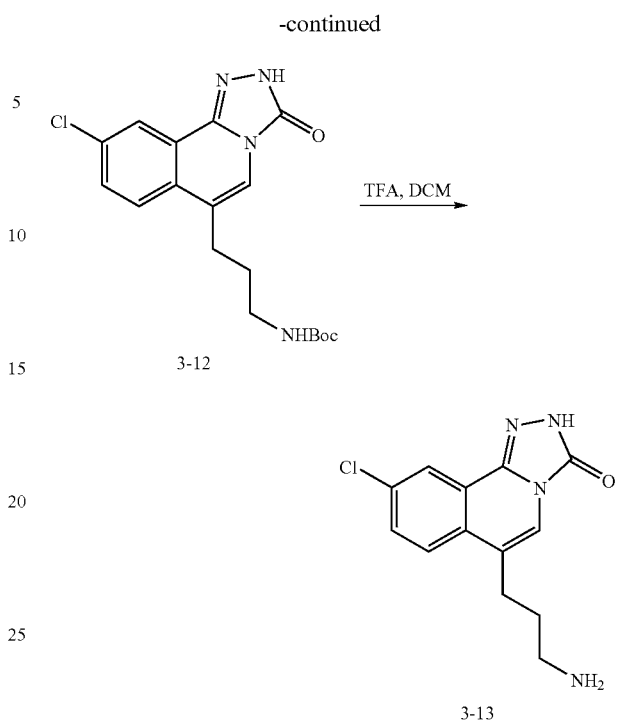

6-[(1E)-3-aminoprop-1-en-1-yl]-9-chloro[1,2,4]triazolo[3,4-a]isoquino-3(2H)-one (3-11) and 6-(3-aminopropyl)-9-chloro[1,2,4]triazolo[3,4-a]isoguinolin-3(2H)-one (3-13)

tert-butl prop-2-ynlcarbamate (3-2)

Propargyl amine (1.16 mL, 18.16 mmol, 1.0 equiv.) was dissolved in dichloromethane (20 mL), and treated with (Boc)$_2$O (3.89 g, 0.88 mmol, 0.98 equiv.) at 0° C. The reaction mixture was allowed to warm up to room temperature overnight. The solvent was evaporated, and the solid residue was recrystallized from Hexane to afford the title product 3-2.

tert-butyl (E)-2-(4,4,5,5-tetramethyl-1,3,2-dioxaborolan-2-yl)ethenylcarbamate (3-3)

Borane-methylsulfide complex (127 mg, 1.68 mmol, 1.3 equiv.) was added dropwise to a solution of (−)-a-pinene (456 mg, 3.35 mmol, 2.6 equiv.) in anhydrous THF (1 mL) at 0° C. under N$_2$. The mixture was stirred at 0° C. for 1 hour and then at room temperature for 2 hours. The mixture was then cooled to 0° C. and a solution of tert-butyl prop-2-ynylcarbamate (3-2) (200 mg, 1.29 mmol, 1.0 equiv.) in anhydrous THF (0.8 mL) was added dropwise. The mixture was stirred at room temperature for 16 hours. The reaction mixture was cooled to 0° C. and acetaldehyde (62 mg, 1.42 mmol, 1.1 equiv.) was added dropwise. After stirred at room temperature for 5 hours, the solvent and excess acetaldehyde were evaporated under vacuum. A solution of pinacol (244 mg, 2.06 mmol, 1.6 equiv.) in heptane (3 mL) was then added to this residue. The reaction mixture was stirred at room temperature for 3 hours. After washing the solution with water (2×10 mL) and drying the organic layer with MgSO$_4$, the solvent was evaporated and the crude product (3-2) was used without purification in the reaction for (3-9 to 3-10).

7-chloroisoquinoline (3-5a)

Aminoacetaldehyde dimethyl acetal (10.54 g, 100.3 mmol, 1.54 equiv.) was added to a solution of 3-chlorobenzaldehyde (9.13 g, 65.0 mmol, 1.0 equiv.) in anhydrous toluene (125 mL). The mixture was refluxed using Dean-Stark trap to remove water. The solvent was then evaporated, and the resulting crude mixture was slowly added to H$_2$SO$_4$ (40 mL) stirred at 140° C. The reaction mixture was poured onto ice 20 minutes after the addition. The mixture was extracted with DCM, the aqueous layer was separated, carefully neutralized to pH=7, and then extracted with Et$_2$O. The organic layer was dried over MgSO$_4$, filtered, and concentrated. The crude residue was purified with silica gel chromatography (EtOAc/Hexane=0->100%) to get the product as mixture of 7-isoquinoline 3-5a and 8-isoquinoline 3-5b (a/b=3/2). LRMS m/z (M+H) 164.1 found, 164.0 required.

4-bromo-7-chloroisoguinoline (3-6)

7-chloroisoquinoline (9 g, 55.0 mmol, 1.0 equiv)[mixture of 7-isoquinoline 3-5a and 8-isoquinoline 3-5b (a/b=3/2)]was dissolved in nitrobenzene (180 mL) and heated at 180° C. Bromine was added dropwise to this dark orange solution (3.11 ml, 60.5 mmol, 1.1 equiv.). The reaction mixture was stirred at 180° C. for 10 hours. LCMS showed that almost complete conversion. The reaction mixture was cooled to room temperature, 2M HCl in Et$_2$O (30 mL) was added, followed by dilution with Et$_2$O and Hexane. The precipitate was collected then taken up with EtOAc (200 mL), neutralized with saturated Na$_2$CO$_3$, and separated. The organic layer was dried over Na$_2$SO$_4$, filtered and concentrated. The crude residue was purified with silica gel chromatography (EtOAc/Hexane=0->30%) to give the title product 3-4. LRMS m/z (M+H) 242.2 found, 241.9 required.

4-bromo-7-chloroisoquinoline 2-oxide (3-7)

4-bromo-7-chloroisoquinoline (3-6)(1 g, 4.12 mmol, 1.0 equiv.) was dissolved in anhydrous CH$_2$Cl$_2$ (8.2 mL) and treated with mCPBA (1.622 g, 9.40 mmol, 2.3 equiv.). The reaction mixture was stirred at room temperature, forming 3-7 as a white precipitate. Following dilution with Et$_2$O, the solid was collected and used without further purification in the next step. LRMS m/z (M+H) 260.1 found, 259.9 required.

4-bromo-1,7-dichloroisoquinoline (3-8)

4-bromo-7-chloroisoquinoline 2-oxide (3-7) (1.2 g, 4.64 mmol, 1.0 equiv.) was dissolved in anhydrous CHCl$_3$ (20 mL) and treated dropwise with phosphorus oxychloride (0.649 mL, 6.96 mmol, 1.5 equiv.). The reaction mixture was refluxed at 66° C. LCMS after 3 hours showed only product. The reaction mixture was diluted with ethyl acetate, washed with saturated NaHCO$_3$, and the organic layer was dried over Na$_2$SO$_4$, filtered and concentrated. The residue was triturated with hexane, and filtered to afford the product 3-8. LRMS m/z (M+H) 277.9 found, 277.9 required.

6-bromo-9-chloro[1,2,4]triazolo[3,4-a]isoguinolin-3 (2H)-one (3-9)

3-9 was prepared via a similar procedure as that for preparing compound 1-2 in Scheme 1, using 4-bromo-1,7-dichloroisoquinoline (3-8) in place of compound (1-1) as starting material. LRMS for (3-9) m/z (M+H) 300.9 found, 300.9 required.

tert-butyl[(2E)-3-(9-chloro-3-oxo-2,3-dihydro[1,2,4]triazolo[3,4-a]isoquinolin-6-yl)prop-2-en-1-yl]carbamate (3-10)

6-bromo-9-chloro[1,2,4]triazolo[3,4-a]isoquinolin-3 (2H)-one (3-9) (60 mg, 0.201 mmol, 1.0 equiv.) and tert-butyl [(2E)-3-(4,4,5,5-tetramethyl-1,3,2-dioxaborolan-2-yl)prop-2-en-1-yl]carbamate (3-3) (228 mg, 0.804 mmol, 4.0 equiv.) were dissolved in anhydrous 1,4-dioxane (0.6 ml) and 2 M K$_2$CO$_3$ aqueous solution (0.2 mL). The reaction mixture was heated to 100° C. LCMS at 18 hours showed complete conversion. Purification with reverse phase HPLC (H$_2$O/CH$_3$CN gradient w/0.1% TFA) afforded the title product 3-10. LRMS m/z (M+H) 375.1 found, 375.1 required.

6-[(1E)-3-aminoprop-1-en-1-yl]-9-chloro[1,2,4]triazolo[3,4-a]isoquinolin-3(2H)-one (3-11)

tert-butyl[(2E)-3-(9-chloro-3-oxo-2,3-dihydro[1,2,4]triazolo[3,4-a]isoquinolin-6-yl)prop-2-en-1-yl]carbamate (3-10) was dissolved in CH$_3$CN (10 mL) with 0.1% TFA present. The resulted solution was irradiated in microwave at 150° C. for 5 minutes. LCMS showed only product. The crude mixture was purified with reverse phase HPLC (H$_2$O/CH$_3$CN gradient w/0.1% TFA) to afford the desired product 3-11. $^1$H NMR (500 MHz, CD$_3$OD) δ 8.29 (d, 1H, J=2.9 Hz), 7.90 (d, 1H, J=8.5 Hz), 7.78-7.64 (m, 2H), 7.14 (d, 1H, J=16.5 Hz), 6.30 (dt, 1H, J=16.5 , 7.0 Hz), 3.83 (d, 2H, J=7.0 Hz). LRMS m/z (M+H) 275.1 found, 275.1 required.

tert-butyl[3-(9-chloro-3-oxo-2,3-dihydro[1,2,4]triazolo[3,4-a]isoquinolin-6-yl)propyl]carbamate (3-12)

To a solution of tert-butyl[(2E)-3-(9-chloro-3-oxo-2,3-dihydro[1,2,4]triazolo[3,4-a]isoquinolin-6-yl)prop-2-en-1-yl] carbamate (3-10)(14 mg, 0.037 mmol, 1.0 equiv.) in EtOH (4 mL), was added Pd(OH)$_2$/C (20% Pd, 1.3 mg, 0.002 mmol, 0.05 equiv.). The reaction mixture was stirred at room temperature for 1.5 hours under atmospheric pressure of hydrogen. The catalyst was then filtered off, and the filtrate was concentrated to dryness. The resulting crude product was purified with reverse phase HPLC (H$_2$O/CH$_3$CN gradient w/0.1% TFA) to afford the titled product (3-12). LRMS m/z (M+H) 377.1 found, 377.1 required.

6-(3-aminopropyl)-9-chloro[1 2,4]triazolo[3,4-a]isoguinolin-3(2H)-one (3-13)

tert-butyl[3-(9-chloro-3-oxo-2,3-dihydro[1,2,4]triazolo [3,4-a]isoquinolin-6-yl)propyl]carbamate (3-12) was dissolved in CH3CN (10 mL) with 0.1% TFA present. The resulting solution was irradiated in microwave at 150° C. for 5 minutes. LCMS showed only product. The crude was purified with reverse phase HPLC (H$_2$O/CH$_3$CN gradient w/0.1% TFA) to afford the pure product (3-13). $^1$H NMR (500 MHz, CD$_3$OD) δ 8.29 (d, 1H, J=2.2 Hz), 7.90 (d, 1H, J=9.0 Hz), 7.75 (dd, 1H, J=9.0, 2.2 Hz), 7.54 (s, 1H), 3.09 (t, 2H, J=7.5 Hz), 2.94 (t, 2H, J=7.5 Hz), 2.06 (pentet, 2H, J=7.5 Hz). LRMS m/z (M+H) 277.1 found, 277.1 required.

The following compounds in Table 3 were prepared by simple modifications of the procedures described for Scheme 3. The compounds were isolated as TFA salts.

TABLE 3

| Cmp | Structure | Name | LRMS m/z (M + H) |
|---|---|---|---|
| 3-14 | 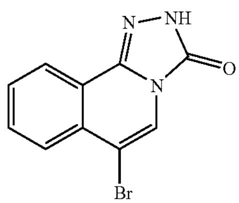 | 6-bromo[1,2,4]triazolo[3,4-α]isoquinolin-3(2H)-one | LRMS m/z (M + H) 265.0 and 267.0 found, 264.0 and 266.0 required. |
| 3-15 | 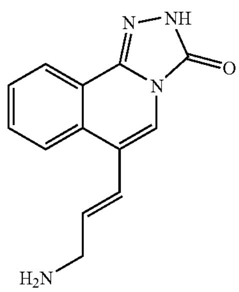 | 6-[(1E)-3-aminoprop-1-en-1-yl][1,2,4]triazolo[3,4-α]isoquinolin-3(2H)-one | LRMS m/z (M + H) 241.1 found, 241.1 required. |
| 3-16 | 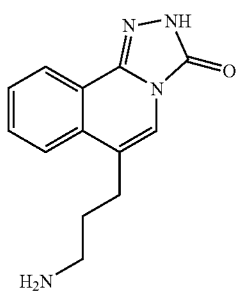 | 6-(3-aminopropyl)[1,2,4]triazolo[3,4-α]isoquinolin-3(2H)-one | LRMS m/z (M + H) 243.2 found, 243.1 required. |
| 3-17 | 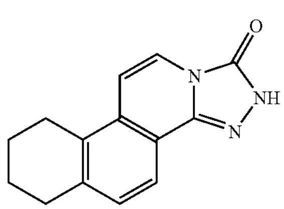 | 6,7,8,9-tetrahydrobenzo[f][1,2,4]triazolo[3,4-a]isoquinolin-1(2H)-one | LRMS m/z (M + H) 307.6? found, 240.1 required. |
| 3-18 | 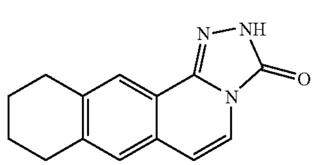 | 8,9,10,11-tetrahydrobenzo[g][1,2,4]triazolo[3,4-a]isoquinolin-3(2H)-one | LRMS m/z (M + H) 307.6? found, 240.1 required. |
| 3-19 | 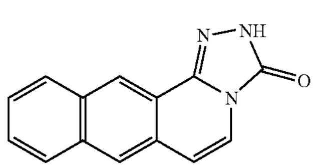 | benzo[g][1,2,4]triazolo[3,4-a]isoquinolin-3(2H)-one | LRMS m/z (M + H) 236.2 found, 236.1 required. |

SCHEME 4

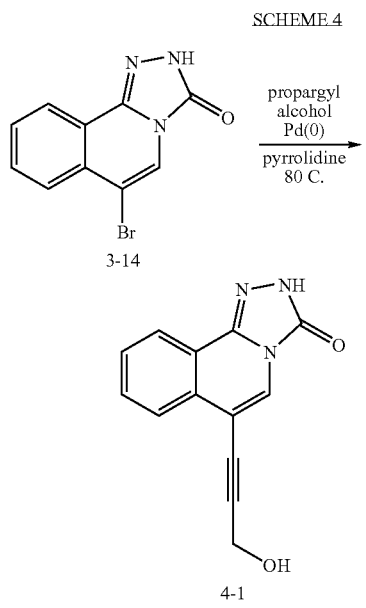

6-(3-hydroxypropyl)[1,2,4]triazolo[3,4-a]isoguinolin-3(2H)-one (4-2)

6-(3-hydroxyprop-1-yn-1-yl)[1,2,4]-triazolo[3,4-a]isoquinolin-3(2H)-one (4-1)

6-bromo-9-chloro[1,2,4]triazolo[3,4-a]isoquinolin-3(2H)-one(3-14) (400 mg, 1.515 mmol, 1.0 equiv) and propargyl alcohol (0.354 mL, 6.06 mmol, 4.0 equiv) were dissolved in pyrrolidine (5.83 mL) and treated with tetrakis(triphenylphosphine)palladium(0) (88 mg, 0.076 mmol, 0.05 equiv). The reaction mixture was heated 80° C. for 4 hours. The solvent was evaporated in vacuo. The resulted residue was purified with silica gel chromatography (EtOAc/Hexane=0->100%) to furnish the pure product (4-1). LRMS m/z (M+H) 240.1 found, 240.1 required.

6-(3-hydroxypropyl)[1,2,4]triazolo[3,4-a]isoguinolin-3(2H)-one (4-2)

6-(3-hydroxyprop-1-yn-1-yl)[1,2,4]triazolo[3,4-a]isoquinolin-3(2H)-one(4-1) (100 mg, 0.418 mmol, 1.0 equiv) and palladium hydroxide (11.74 mg, 0.017 mmol, 0.04 equiv) were suspended in MeOH (6 ml). A hydrogen balloon was attached to the flask. The reaction mixture was stirred at room temperature. LCMS at 40 minutes showed only the product. The catalyst was filtered off, and washed with MeOH. The filtrate was concentrated. The crude was purified with reverse phase HPLC (H$_2$O/CH$_3$CN gradient w/0.1% TFA present) to yield product (4-2). $^1$H NMR (500 MHz, CD$_3$OD) δ 8.27 (d, 1H, J=8.0 Hz), 7.91 (d, 1H, J=8.0 Hz), 7.73 (dt, 1H, J=8.0, 1.4 Hz), 7.62 (dt, 1H, J=8.0, 1.4 Hz), 7.47 (s, 1H), 3.69 (t, 2H, J=6.5 Hz), 2.91 (t, 2H, J=7.5 Hz), 2.03-1.76 (m, 2H). LRMS m/z (M+H) 244.2 found, 244.1 required.

SCHEME 5

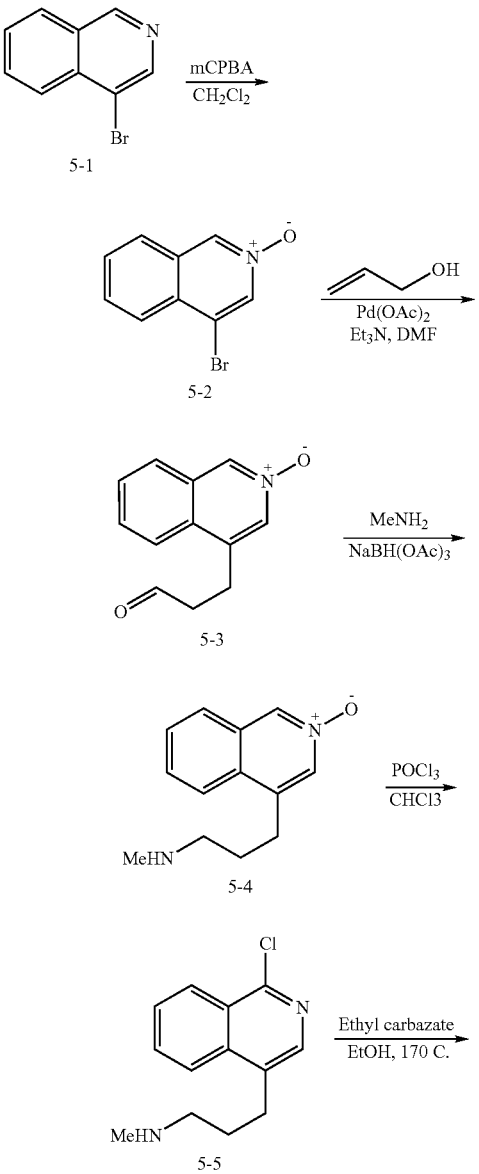

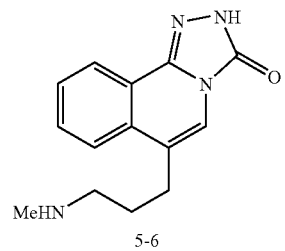

6-[3-(methylamino)propyl][1,2,4]triazolo[3,4-a]isoquinolin-3(2H)-one (5-6)

4-bromoisoquinoline 2-oxide (5-2)

Compound (5-2) was prepared via a similar procedure as that for preparing compound (3-7) in Scheme 3, using 4-bromoisoquinoline (5-1) in place of compound (3-6) as starting material. LRMS for (5-2) m/z (M+H) 224.9 and 225.9 found, 225.0 and 226.0 required.

3-(2-oxidoisoquinolin-4-yl)propanal (5-3)

4-bromoisoquinoline 2-oxide (5-2) (500 mg, 2.23 mmol, 1.0 equiv), lithium chloride (95 mg, 2.23 mmol, 1.0 equiv) and palladium(II) acetate (20.04 mg, 0.089 mmol, 0.04 equiv) were dissolved in anhydrous DMF (8.6 mL). To this orange solution, was added triethylamine (933 µl, 6.69 mmol, 3.0 equiv) and allyl alcohol (308 µl, 4.46 mmol, 2.0 equiv). The reaction mixture was heated at 100° C. for 1.5 hours. Black precipitate was formed. And LCMS showed the starting material was completely consumed. The reaction mixture was filtered, and washed with EtOAc, then concentrated. The crude was purified with silica gel chromatography (MeOH/EtOAc=0->20%) to afford the compound (5-3). LRMS m/z (M+H) 202.1 found, 202.2 required.

N-methyl-3-(2-oxidoisoguinolin-4-yl)propan-1-amine (5-4)

3-(2-oxidoisoguinolin-4-yl)propanal (5-3) (170 mg, 0.85 mmol, 1.0 equiv) was treated with a 2.0M solution of methylamine in THF(1.2 ml, 2.40 mmol, 2.8 equiv), followed by addition of sodium triacetoxyborohydride (86 mg, 0.41 mmol, 0.5 equiv). The reaction mixture was stirred at room temperature. When the LCMS showed mostly product, the reaction mixture was diluted with EtOAc, and washed with saturated $NaHCO_3$ aqueous solution. The combined organic layer was dried over $Na_2SO_4$, filtered and concentrated. The crude was purified with was purified with reverse phase HPLC ($H_2O/CH_3CN$ gradient w/0.1% TFA present) to yield product (5-4). LRMS m/z (M+H) 217.2 found, 217.1 required.

3-(1-chloroisoguinolin-4-yl)-N-methylpropan-1-amine (5-5)

Compound (5-5) was prepared via a similar procedure as that for preparing compound (3-8) in Scheme 3, using N-methyl-3-(2-oxidoisoquinolin-4-yl)propan-1-amine (5-4) in place of compound (3-7) as starting material. LRMS (5-5) m/z (M+H) 235.1 found, 235.1 required.

6-[3-(methylamino)propyl][1,2,4]triazolo[3,4-a]isoguinolin-3(2H)-one (5-6)

Compound (5-6) was prepared via a similar procedure as that for preparing compound (3-9) in Scheme 3, using 3-(1-chloroisoquinolin-4-yl)-N-methylpropan-1-amine (5-5) in place of compound (3-8) as starting material. For compound (5-6), $^1$H NMR (500 MHz, $CD_3OD$) δ 8.31 (d, 1H, J=7.5 Hz), 7.90 (d, 1H, J=8.0 Hz), 7.73 (dt, 1H, J=8.0, 1.5 Hz), 7.66 (dt, 1H, J=8.0, 1.5 Hz), 7.53 (s, 1H), 3.13 (t, 2H, J=8.0 Hz), 2.95 (t, 2H, J=8.0 Hz), 2.72 (s, 3H), 2.08 (pentet, 2H, J=8.0 Hz); LRMS m/z (M+H) 257.2 found, 257.1 required.

The compounds shown in Table 4 were synthesized according to the Reaction Schemes and Scheme 5. The compounds were isolated as TFA salts.

TABLE 4

| Cmp | Structure | Name | LRMS m/z (M + H) |
| --- | --- | --- | --- |
| 5-7 | 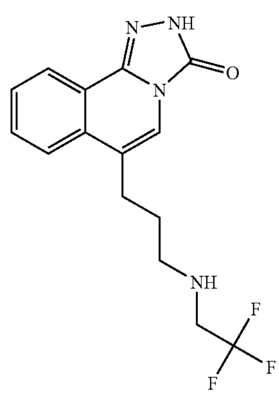 | 6-{3-[(2,2,2-trifluoroethyl)amino]propyl} [1,2,4]triazolo[3,4-α] isoquinolin-3(2H)-one | LRMS m/z (M + H) 325.0 found, 325.1 required. |
| 5-8 | 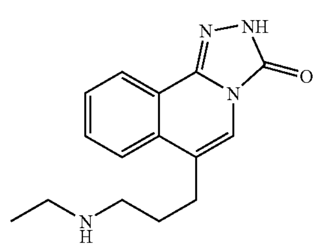 | 6-[3-(ethylamino)propyl] [1,2,4]triazolo[3,4-α] isoquinolin-3(2H)-one | LRMS m/z (M + H) 271.1 found, 271.1 required. |

SCHEME 6

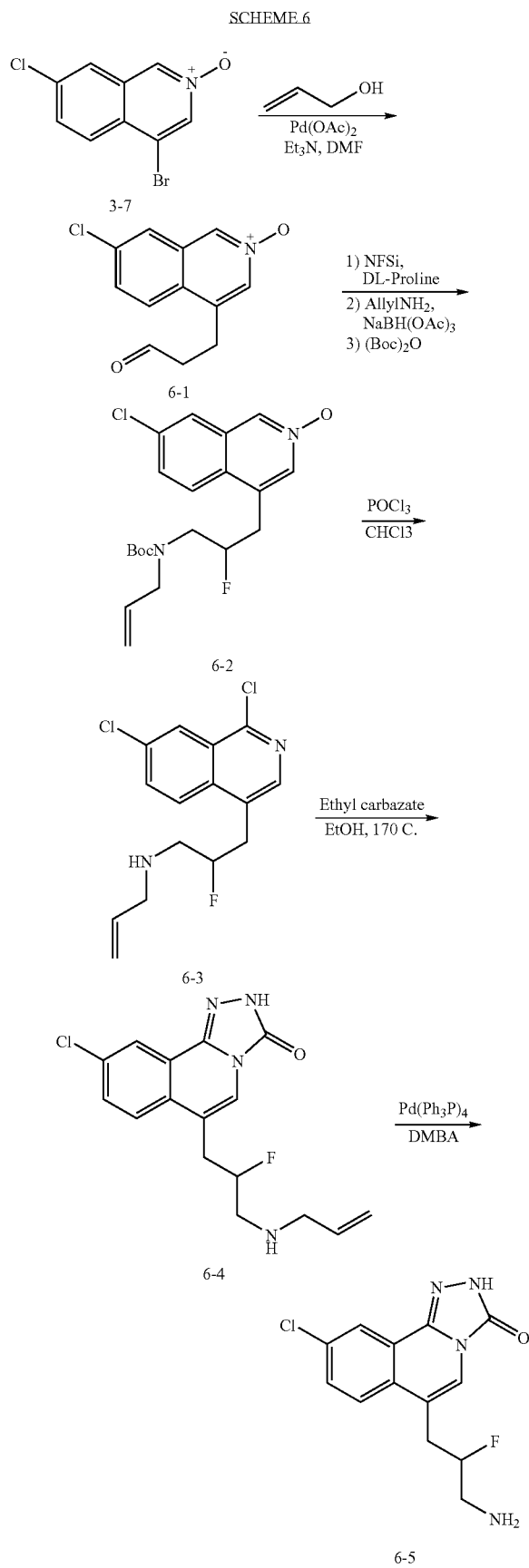

6-(3-amino-2-fluoropropyl)-9-chloro[1,2,4]triazolo[3,4-a]isoquinolin-3(2H)-one (6-5)

3-(7-chloro-2-oxidoisoquinolin-4-yl)propanal (6-1)

Compound (6-1) was prepared via a similar procedure as that for preparing compound (5-3) in Scheme 5, using 4-bromo-7-chloroisoquinoline 2-oxide (3-7) in place of compound (5-2) as starting material. LRMS for compound (6-1) m/z (M+H) 236.0 found, 236.0 required.

tert-butyl allyl[3-(7-chloro-2-oxidoisoquinolin-4-yl)-2-fluoropropyl]carbamate (6-2)

3-(7-chloro-2-oxidoisoquinolin-4-yl)propanal (6-1)(300 mg, 1.27 mmol, 1.0 equiv) and N-fluorobenzenesulfonimide (442 mg, 1.40 mmol, 1.1 equiv) were dissolved in THF (11.6 mL) and isopropyl alcohol (1.16 mL). To this mixture, was added DL-proline (29.3 mg, 0.26 mmol, 0.2 equiv). The reaction mixture was stirred at room temperature overnight. LCMS showed product. To this reaction mixture, were added allylamine (191 μl, 2.55 mmol, 2.0 equiv) and sodium triacetoxyborohydride (1.08 g, 5.09 mmol, 4.0 equiv). The reaction mixture was stirred at room temperature for 3 hours before (Boc)$_2$O (833 mg, 3.82 mmol, 3 equiv) was added. The resulted reaction mixture was stirred at room temperature overnight. The reaction mixture was then quenched with H$_2$O, and extracted with EtOAc. The combined organic layers were dried over Na$_2$SO$_4$, filtered, and concentrated. The crude was purified with silica gel chromatography (EtOAc/Hexane=0->100%) to afford the product (6-2). LRMS m/z (M+H) 395.1 found, 395.2 required.

N-[3-(1,7-dichloroisoguinolin-4-yl)-2-fluoropropyl]prop-2-en-1-amine (6-3)

Compound (6-3) was prepared via a similar procedure as that for preparing compound (3-8) in Scheme 3, using tert-butyl allyl[3-(7-chloro-2-oxidoisoquinolin-4-yl)-2-fluoropropyl]carbamate (6-2) in place of compound (3-7) as starting material. LRMS for compound (6-3) m/z (M+H) 313.0 found, 313.1 required.

6-[3-(allylamino)-2-fluoropropyl]-9-chloro[1,2,4]triazolo[3,4-a]isoquinolin-3(2H)-one (6-4)

Compound (6-4) was prepared via a similar procedure as that for preparing compound (3-9) in Scheme 3, using N-[3-(1,7-dichloroisoquinolin-4-yl)-2-fluoropropyl]prop-2-en-1-amine (6-3) in place of compound (3-8) as starting material. LRMS for compound (6-4) m/z (M+H) 335.0 found, 335.1 required.

6-(3-amino-2-fluoropropyl)-9-chloro[1,2,4]triazolo[3,4-a]isoquinolin-3(2H)-one (6-5)

6-[3-(allylamino)-2-fluoropropyl]-9-chloro[1,2,4]triazolo[3,4-a]isoquinolin-3(2H)-one (6-4)(18 mg, 0.054 mmol, 1.0 equiv) and DMBA (25.2 mg, 0.16 mmol, 3.0equiv) and tetrakis(triphenylphosphine)palladium(0) (3 mg, 2.60 μmol, 0.05 equiv) were suspended in ClCH$_2$CH$_2$Cl (1 mL). The resulted yellow suspension was heated at 50° C. LCMS at 5 hours showed mostly product. The crude was purified with reverse phase HPLC H$_2$O/CH$_3$CN gradient w/0.1% TFA present) to afford the pure product (6-5). $^1$H NMR (500 MHz, CD$_3$OD) δ 8.26 (d, 1H, J=2.3 Hz), 7.88 (d, 1H, J=8.5 Hz), 7.72 (dd, 1H, J=8.5, 2.3 Hz), 7.61 (s, 1H), 5.19-4.94 (dm, 1H, J=50.0 Hz), 3.52-3.33 (m, ~4H, overlap w/solvent peak). LRMS m/z (M+H) 295.3 found, 295.1 required.

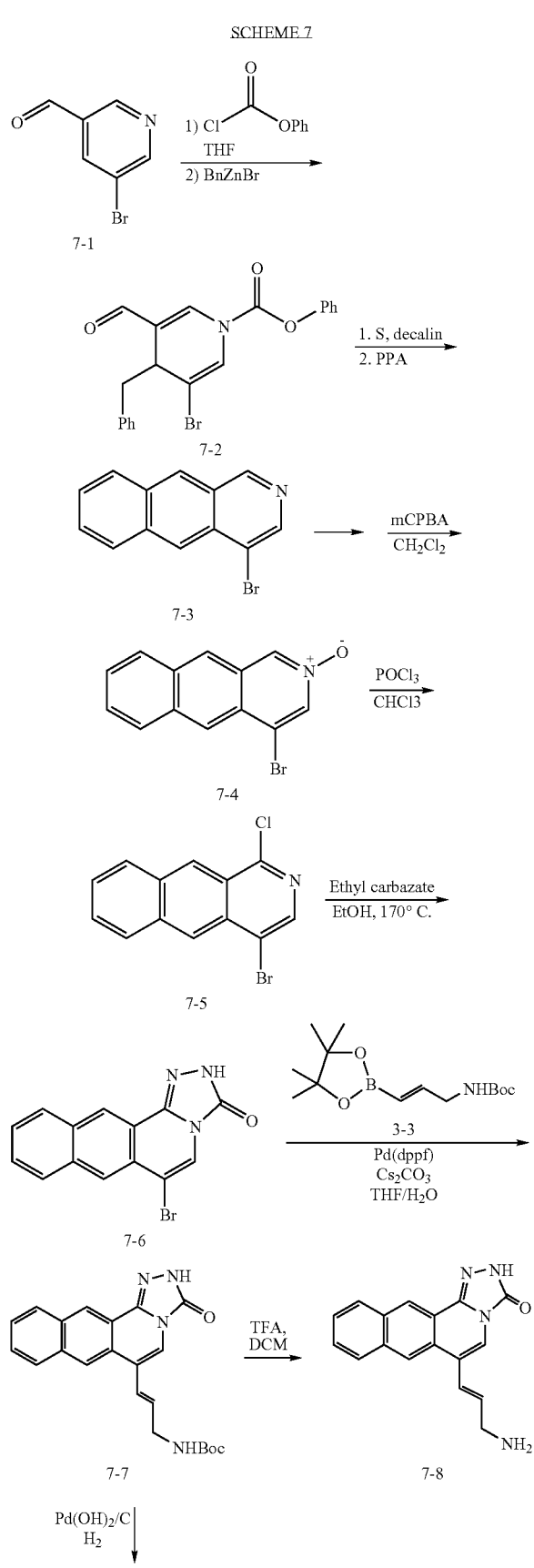

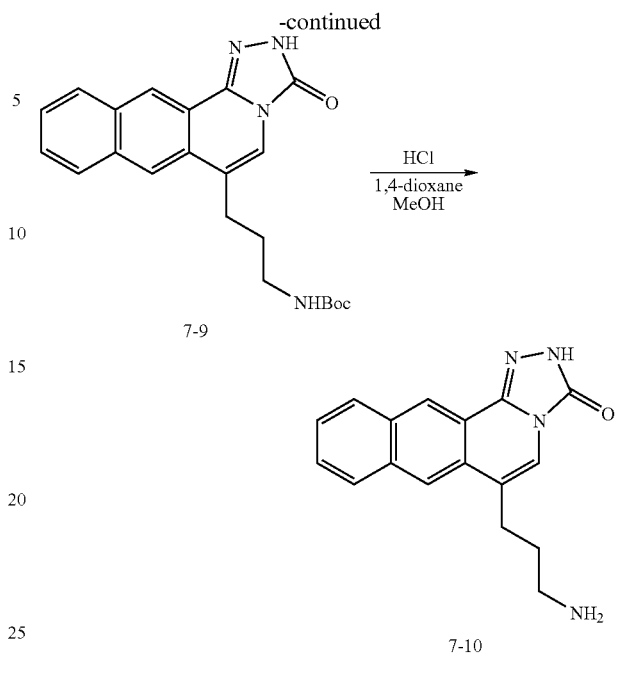

6-[(1E)-3-aminoprop-1-en-1-yl)benzo[g][1,2,4]triazolo[3,4-a]isoquinolin-3(2H)-one (7-8) and 6-(3-aminopropyl)benzo[g][1,2,4]triazolo[3,4-a]isoguinolin-3(2H)-one (7-10)

phenyl 4-benzyl-3-bromo-5-formylpyridine-1(4H)-carboxylate (7-2)

A solution of 5-bromonicotinaldehyde (7-1) (930 mg, 5 mmol, 1 eq) in anhydrous THF (10 ml) was cooled to 0° C. and treated with phenylchloroformate (783 mg, 5 mmol, 1eq). The reaction mixture was then stirred at this temperature for 1 h before the addition of benzylzinc bromide (0.5M in THF, 10 ml, 5 mmol, 1eq). The resulting solution was stirred at 0° C. for another 30 min, was then allowed to warm to room temperature and poured into saturated aqueous solution of ammonium chloride. The organic layer was separated and the aqueous layer was extracted three times with ethyl acetate, the combined organic extracts were dried and concentrated to give the title dyhydropyridine 7-2, which was used in the next step without further purification. LRMS m/z: found 398.0, 400.0, calcd. (M+H) 398.0, 400.0

4-bromobenzo[g]aisoguinoline (7-3)

A suspension of phenyl 4-benzyl-3-bromo-5-formylpyridine-1(4H)-carboxylate (7-2), obtained in the previous step, and sulfur (321 mg, 10 mmol, 2 eq), in decalin (20 ml) was refluxed for 15 hrs and then added to polyphosphoric acid (30 ml), stirred at 140° C. The reaction mixture was stirred at this temperature for 30 min and then poured into ice/water mixture. The aqueous layer was washed with ethyl acetate, basified to pH~9 and then extracted with ethyl acetate three times. The combined extracts were dried and concentrated to give crude product 7-3. LRMS m/z: found 258.0, 260.0, calcd. (M+H) 258.0, 260.0. 1H NMR (500 MHz, CDCl3) δ: 7.61-7.71 (m, 2H), 8.13-8.17 (m, 2H), 8.6 (s, 1H), 8.66 (s, 1H), 9.37 (s, 1H).

4-bromobenzo[g]isoquinoline 2-oxide (7-4)

A solution of 4-bromobenzo[g]isoquinoline (7-3) (390 mg, 1.5 mmol, 1. eq) in dichloromethane (25 ml) was treated with mCPBA (~70%, 559 mg, 2.27 mmol, 1.5 eq) and the reaction mixture was stirred at room temperature until LCMS showed complete conversion. The reaction mixture was diluted with ether, and the precipitate was collected by filtration, washed with ether, and dried to give the title N-oxide 7-4. LRMS m/z: found 274.0, 276.0, calcd. (M+H) 274.0, 276.0

4-bromo-1-chlorobenzo[g]isoquinoline (7-5)

4-Bromo-benzo[g]isoquinoline 2-oxide (7-4) (380 mg, 1.39 mmol, 1 eq) was taken up in a ¼ v/v mixture of POCl$_3$ and chloroform (20 ml) and the resulting solution was stirred at 55° C. for 2 hrs. The reaction mixture was then carefully poured into sat. aq. sodium bicarbonate, extracted with ethyl acetate, dried, and concentrated to give the crude desired chloride 7-5. LRMS m/z: found 294.0, 292.0, calcd. (M+H) 294.0, 292.0

6-bromobenzo[g][1,2,4]triazolo[3,4-a]isoquinolin-3 (2H)-one (7-6)

A suspension of 4-bromo-1-chlorobenzo[g]isoquinoline (7-5) (50 mg, 0.171 mmol, 1 eq) and ethyl carbazate (53 mg, 0.513 mmol, 3 eq) in ethanol (2 ml) was heated in a sealed tube under microwave irradiation for 60 min at 170° C. The resulting mixture was purified on RP HPLC (MeCN/water w TFA) to give the desired condensation product 7-6. LRMS m/z: found 314.0, 316.0, calcd. (M+H) 314.0, 316.0. 1H NMR (500 MHz, CDCl$_3$) δ: 7.67-7.71 (m, 2H), 7.84 (s, 1H), 8.07-8.10 (m, 2H), 8.46 (s, 1H), 8.82 (s, 1H).

tert-Butyl[(2E)-3-(3-oxo-2,3-dihydrobenzo[g][1,2,4]triazolo[3,4-a]isoquinolin-6-yl)prop-2-en-1-yl]carbamate (7-7)

To a solution of tert-butyl[(2E)-3-(4,4,5,5-tetramethyl-1,3,2-dioxaborolan-2-yl)prop-2-en-1-yl]carbamate (3-3) (32.5 mg, 0.115 mmol, 4 eq) and 6-bromobenzo[g][1,2,4]triazolo[3,4-a]isoquinolin-3(2H)-one (7-6) (9.0 mg, 0.029 mmol, 1 eq) in THF (0.5 ml) was added a solution of cesium carbonate (18.7 mg, 0.058 mmol, 2 eq) in water (0.2 ml), and the resulting mixture was deoxygenated with nitrogen and treated with Pd(dppf) (1.0 mg, 0.0014 mmol, 0.05 eq). The reaction mixture was deoxygenated again, and heated in a sealed tube under microwave irradiation for 8 min at 150° C. The resulting suspension was filtered through a pad of Celite washing with DMF, and the filtrate was purified on RP HPLC (MeCN/Water with TFA) to afford the desired coupling product 7-7. LRMS m/z: found 391.2, calcd. (M+H) 391.2.

6-[(1E)-3-aminoprop-1-en-1-yl]benzo[g][1,2,4]triazolo[3,4-a]isoquinolin-3(2H)-one (7-8)

A solution of tert-butyl[(2E)-3-(3-oxo-2,3-dihydrobenzo[g][1,2,4]triazolo[3,4-a]isoquinolin-6-yl)prop-2-en-1-yl] carbamate (7-7) (3.0 mg, 0.0077 mmol) in a ¼ mixture of dichloromethane and TFA (1.0 ml) was stirred at room temperature for 15 min and concentrated to dryness to give the deprotected material 7-8 as a TFA salt. LRMS m/z: found 291.1, calcd. (M+H) 291.1. 1H NMR (500 MHz, CD$_3$OD) δ: 3.88 (d, J=6.6 Hz, 2H), 6.35 (dt, J=6.6, 15.6 Hz, 1H), 7.31 (d, J=15.7 Hz, 1H), 7.63 (s, 1H), 7.65-7.68 (m, 2H), 8.05-8.11 (m, 2H), 8.38 (s, 1H), 8.84 (s, 1H).

tert-Butyl[3-(3-oxo-2,3-dihydrobenzo[g][1,2,4]triazolo[3,4-a]isoquinolin-6-yl)propyl]carbamate (7-9)

A solution of 6-[(1E)-3-aminoprop-1-en-1-yl]benzo[g][1,2,4]triazolo[3,4-a]isoquinolin-3(2H)-one (7-8) (890 mg, 1.1 mmol, 1 eq) in MeOH (120 ml) was treated with palladium (II) hydroxide on carbon (20%, 77 mg, 0.1 eq) and stirred at room temperature under atmospheric pressure of hydrogen. The reaction was monitored by LCMS and filtered after all starting material was consumed. The filtrate was concentrated and the resulting residue was purified by RP HPLC (MeCN/Water with TFA) to give the title product 7-9. LRMS m/z: found 393.2, calcd. (M+H) 393.2. 1H NMR (500 MHz, CD$_3$OD) δ: 1.96-2.03 (m, 2H), 2.96 (t, J=8.1 Hz, 2H), 3.25-3.29 (t, J=7.1 Hz, 2H), 7.41 (s, 1H), 7.62-7.66 (m, 2H), 8.05-8.09 (m, 2H), 8.31, (s, 1H), 8.82 (s, 1H).

6-(3-aminopropyl)benzo[g][1,2,4]triazolo[3,4-a]isoguinolin-3(2H)-one (7-10)

A solution of tert-butyl[3-(3-oxo-2,3-dihydrobenzo[g][1,2,4]triazolo[3,4-a]isoquinolin-6-yl)propyl]carbamate (7-9) (162 mg, 0.41 mmol, 1 eq) in 1,4-dioxane (20 ml) and methanol (10 ml) was treated with concentrated aqueous HCl (2.0 ml) and the reaction mixture was stirred at room temperature for 2 h and concentrated. The resulting residue was dissolved in water, washed with ethyl acetate, and the aqueous layer was concentrated to give the desired deprotected product 7-10 as HCl salt. LRMS m/z: found 293.1, calcd. (M+H) 293.1. 1H NMR (500 MHz, D$_2$O) δ: 1.62-1.71 (m, 2H), 2.13-2.20 (m, 2H), 2.90-2.97 (m, 2H), 6.02 (s, 1H), 7.11-7.33 (m, 6H).

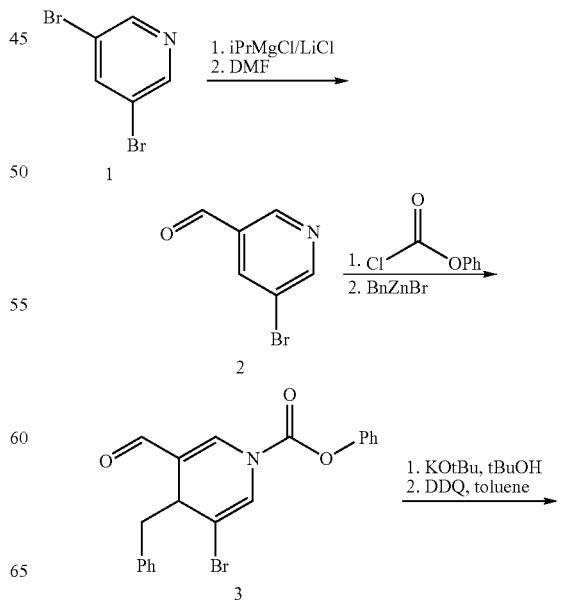

SCHEME 7 (ALTERNATE SYNTHESIS)

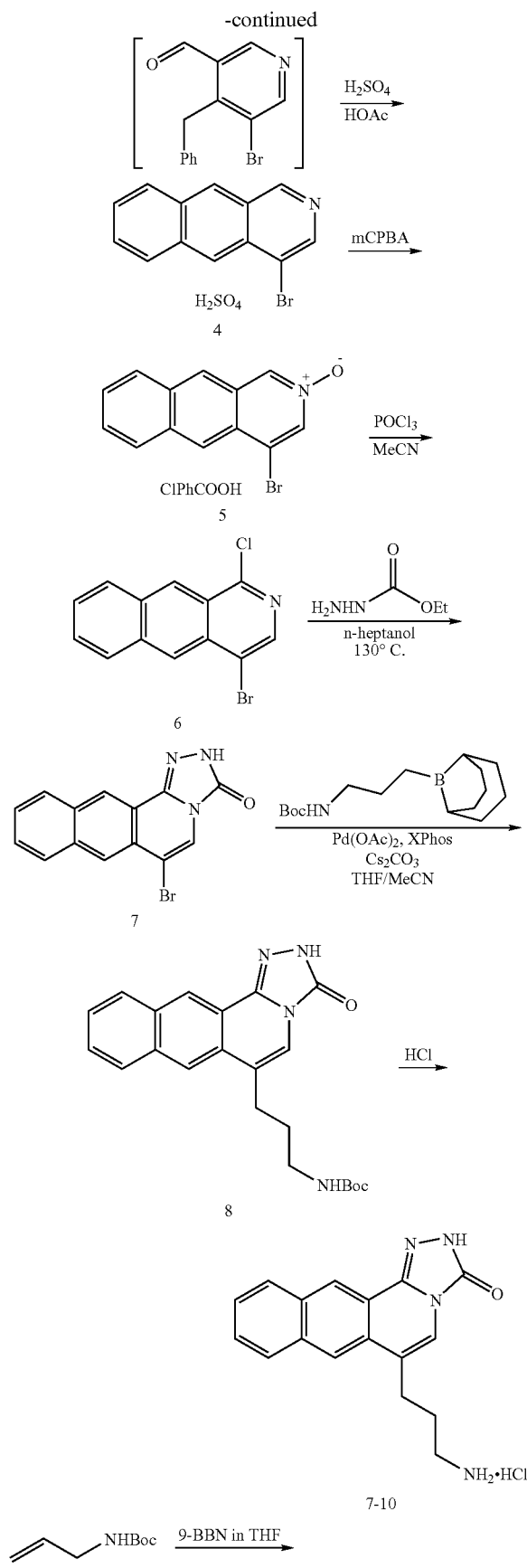

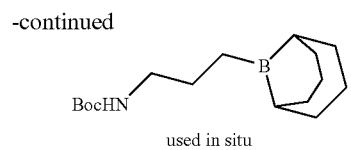

used in situ

To a solution of the grignard in THF (11.95 kg, 116.2 mol, 2 vols) at 10 degrees was added a solution of 3,5 Dibromo pyridine 1 in THF (25 kg, 105.6 mol, 3.5 vols) maintaining temperature. After 10 min age a sample was quenched with deuterated methanol to ensure starting material consumption (3,5 dibromo pyridine, 8.30 δ (s, 1H) and 8.65δ (2 H)). Additional grignard can be charged as necessary. DMF (32.55 L, 528 mol, 5 equivalents) is added maintaining the temperature at less than 20 degrees, aged for 30 mins and then finally quenched with aqueous acetic acid (14.4 L, 251.2 mol, 3 mol equivs). Heptane (150 L, 4 vols) is charged and the organic phase separated and washed with dilute aqueous lithium chloride to remove residual DMF. Final dilute aqueous sodium bicarbonate wash ensured the pH was slightly basic, as traces of acid may impact the subsequent step. Final solvent switch to heptane initiated the crystallisation (it is recommended to seed prior to spontaneous nucleation of the dense aldehyde product). The product dried under a nitrogen stream, giving 2.

To a 50 L cylindrical vessel was charged THF (13.5 L) and Aldehyde, 2 (1.35 kg, 1 eq) and stirred until all aldehyde had dissolved. With stirring, Phenyl chloroformate (960 mL, 1.05eq) was added at room temperature and aged for 2 hours. The slurry was cooled to −20° C. and Benzyl Zincbromide was added dropwise over 1 hour (14.5 L, 1.0eq) then aged at temperature for 2 hours. To quench, the reaction solution was fed into a 50 L extractor with saturated ammonium chloride solution (13.5 L, 10 volumes). The product was extracted with MTBE (13.5 L, 10 volumes). The layers were cut and the organic layer was washed with 25% brine solution (13.5 L, 10 volumes). Resulting organic layer (~40 L) was dried overnight over sodium sulfate. The organics were decanted off and fed into a 50 L, 4 neck round bottom flask equipped with nitrogen line, thermocouple, and batch concentrator. The solution was distilled at 10-15° C., 27-28 in Hg. When solution volume reached 10-12 L, the solution was flushed with 2×MTBE (6.75 L, 5 volumes) and after each addition allowed to concentrate down to 10 L. After second flush, reaction was distilled further to ~5 reaction volumes (~7 L). Hexanes (13.5 L, 10 volumes) were added portion wise to push crystallization further. The solid was isolated by filtration, using mother liquors to complete the transfer. The cake was washed with 2:1Hexanes/MTBE (2×3.5 L) and dried on the filter under nitrogen tent for 1 day. The product 3 was obtained as a yellowish crystalline solid.

Reaction was performed in a 50 L cylindrical vessel equipped with a nitrogen inlet, stirring shaft, thermocouple, and heating coils. The solution of tBuOH (10 volumes) and water (10 equiv relative to SM total mass) was prepared one day in advance. Carbamate 3 (1.747 kg/1.66 kg by assay) was charged to the vessel at room temperature. tBuOK (740 g, 1.6 equiv) was charged portionwise (temperature increased to 34° C.). A pale yellow slurry was obtained. The solution was heated to 55° C. and stirred for 2 hours (assay showed 72% conversion). Another 0.15 equiv (70 g) of tBuOK was added and the solution was aged for another 2 h 45 min and assay showed 98% conversion. Reaction was cooled to 30° C. and diluted with water (to solubilize the solids ppt formed during the reaction—presumably PhOK) and toluene (17.5 L, 5 vol).

The solution was cooled further to 5° C. and quenched slowly with 1.0 N HCl (7.3 L, 1.75 equiv), temperature was maintained at or below 9° C. The solution was stirred for 5 min and the layers were cut. Water (10 vol) and toluene (5 vol) was added (the additional toluene facilitates the $2^{nd}$ cut significantly). The layers were cut and the organic was washed another 3×17.5 L with water (assay showed no tBuOH remaining after $4^{th}$ water wash, notes: product starts to crash out of toluene solution a little, observed rag layer). The organics were washed with 20% NaCl (Kf=1280 ppm). The dihydropyridine after workup is not stable in toluene and should be used immediately in the next step.

The solution of dihydropyridine in toluene (from the previous step) was cooled to 2° C. and charged portionwise with 703 g of DDQ. The yellow solution immediately turned dark red, and then into a pink slurry (due to formation of DDQH). A mild exotherm was observed with each charge of DDQ and the temperature was maintained below 5° C. As the reaction was not complete (determined by HPLC assay), an additional 0.1 equiv (70 g) of DDQ was added followed by another 0.4 equiv (28 g) of DDQ. The slurry was poured onto a bed of solka floc, filtered, and washed with toluene until the solids were mostly colorless. The solution was assayed to show 922 g of pyridine. The solution was kept at room temperature overnight. The following day, pyridine in toluene was washed 2× with 1.0 N NaOH (8.6 L). The organics was washed 1× with water, 1×20% NaCl and concentrated to 3 volumes in toluene. This solution was stored overnight at room temperature.

A solution of pyridine in toluene at room temperature was charged with acetic acid followed by sulfuric acid (a mild exotherm was observed during addition of $H_2SO_4$, temperature increased to 35° C.). The greenish-brown solution was heated to 50° C. (overheated to 59° C. for ~20 minutes) and seeded at t=1 hour with 11.5 g of product. The clear solution immediately became a slurry and the slurry was stirred for another 2 hours. The solution was cooled to 10° C. (caution: solution cooled to 4° C. solidifies and cannot be filtered!) and filtered. The filtrate was washed with 1.1 L of acetic acid followed by 3×2 L of ethyl acetate. The yellow crystalline solids were dried under nitrogen overnight to yield benzoisoquinoline 4.

To a 22 L extractor was charged 800 mL of 10 N NaOH, 3.2 L of GMP water, 10 L of dichloromethane, and compound 4. After 4 was dissolved, the bottom organic solution was collected for the reaction. To another 50 L flask was charged 839 g of m-CPBA and 10 L of dichloromethane. After m-CPBA was dissolved (temperature decreased to 12° C.), the free base solution of 1 was added at 12-26° C. over 1 h (cold water bath needed for temperature control). Thick slurry formed during the addition and it was agitated at RT for 17 h. After HPLC showed no 1, the slurry was filtered (slow, took 2 h) and the cake was rinsed with 2 L of dichloromethane. The yellow solid product was dried under vacuum at RT, and 1.114 kg of the product 5 was obtained.

Compound 5 (1090 g, ~2.53 mol) was suspended in 18 L of acetonitrile in a 50 L flask at RT. $POCl_3$ (256 mL, 2.79 mol) was added to the flask over 3.25 h at <25° C. (water bath was used) and resulting slurry was aged at RT for another 3 h. 18 L of 0.5 M $K_2HPO_4$ were added over 1.5 h to quench the reaction. After 30 min age, the slurry was filtered and the cake was washed with 18 L of sat. $Na_2CO_3$, and then 18 L of GMP water. The yellow solid product was dried at RT under nitrogen flow over weekend and 678 g of the product 6 was obtained.

To a 50 L flask was charged compound 6 (644 g, ~2.2 mol), heptanol (19.3 L), ethyl carbazate (252 g, 2.42 mol) and p-TsOH—$H_2O$ (105 g, 0.55 mol). The mixture was heated to 124° C. over 2.5 h and was aged at 120-126° C. for 17 h. Resulting slurry was cooled to 36° C. over 4 h and was filtered. The cake was washed with 2×1.5 L of ethanol, and then was dried under nitrogen at RT. The product 7 was obtained as brown crystalline solid.

28 L of 9-BBN in THF was cooled to <15° C. in a 50 L R.B. flask before charging in the 2.0 kg of tert-butyl allylcarbamate. The solution was then allowed to warm to room temperature and aged for 2 hours. After two hours, the solution was cooled to <15° C. and 2 L of $H_2O$ was charged into the clear 9-BBN solution and sparged for 15 minutes to inert the solution and eliminate the resulting $H_2$ gas. 2.0 kg Triazole, 7, was then charged into the clear 9-BBN adduct solution and degassed again by sparging with $N_2$ for 15 minutes. One hour before addition of the triazole and $H_2O$ to the 9-BBN solution, the catalyst solution was made up. 4.3 kg of $CsCO_3$ and 10 L MeCN were charged into a 50 L R.B. flask and sparged with $N_2$ for 15 minutes. Pd(OAc)2 (42 g) and X-Phos (181 g) were then quickly charged into the slurry and the resulting slurry was aged with continued sparging at room temperature for 1 hour. The degassed 9-BBN adduct and triazole slurry was then vacuum transferred into the catalyst solution maintaining inertion. The resulting slurry was heated to 55° C., with continued sparging until the reaction temperature reached 45° C. Conversion was monitored by HPLC. After being cooled to room temperature, the solution was in-line filtered through solka flok, rinsed with 60 L THF, and transferred into a 180 L extractor. The solution is then washed with 60 L brine and 60 L 1:1 1N HCl:brine. The resulting slurry in THF was heated up to 45° C. in the 100 L extractor and then cooled to <15° C. After aging for 30 minutes at temperature, the slurry was filtered directly from the filtered directly from the 100 L extractor. The coupling product, 8, is then dissolved in 65 L NMP by heating to 40° C. in a 72 L R.B. flask. The resulting red solution is filtered through an inline filter, cooled to room temperature, and then recrystallized with 35 L $H_2O$. The slurry is then filtered and the cake is washed with 17.5 L MeCN. The yellowish white solid is dried under N. 1.879 kg of the product was obtained with >99 LCAP and <1% des-Br as a fluffy crystalline solid.

To a 50 L cyclindrical vessel with $N_2$ inlet, was charged 32 L of EtOH. The intermediate 8 (1819.3 g, 4.6 mol) was added, followed by concentrated hydrochloric acid (3.0 L, 12.1 N). The resulting slurry was heated to 66-72° C. for 3 hours. The resulting slurry was cooled to 15-20° C. and the solid isolated directly by filtration. The cake was washed with EtOH (2×4 L) and dried overnight under nitrogen flow. The crude product 7-10 was obtained as a beige solid. To a 50 L round bottom flask was added crude 7-10 (1423.0 g, 4.4 mol) and pyrogen-reduced water (29 L, 20 vol). With vigorous stirring, Ecosorb C-943 was added and the mixture aged for 3 hours. The slurry was filtered through solka flok using 7 L of water for rinse (5 vol). The solka flok bed was washed with pyrogen reduced water until the filtrate was clear and colorless. The filtrate was transferred into a 72 L round bottom flask through a 5 um inline filter. To the resulting solution, 5N HCl was added (1.8 L, 2.0 eq) and the solution seeded. The solution was seeded with 10 g of solid 7-10 HCl salt; after aging little additional precipitation seen. An aliquot (800 mL) of the mixture was taken and additional SN HCl added, giving a thick slurry which was added back into the batch. The mixture was allowed to age overnight to develop a seed bed. The remaining HCl (5.2 L) was added dropwise. The solid was isolated by filtration using the MLs to complete the transfer. The cake is washed with EtOH (4 L) and dried under nitrogen. The cake was broken up and passed through a mesh sieve to delump. The product 7-10 was obtained as an off white solid The following compounds in Table 5 were prepared as TFA salts following the procedures shown in Scheme 7.

TABLE 5

| | | | |
|---|---|---|---|
| 7-11 | 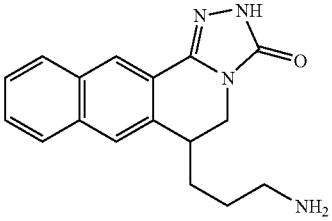 | 6-(3-aminopropyl)-5,6-dihydrobenzo[g][1,2,4]triazolo[3,4-a]isoquinolin-3(2H)-one | LRMS m/z (M + H) 295.2 found, 295.2 required. |
| 7-12 | 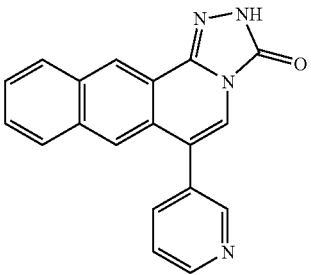 | 6-pyridin-3-ylbenzo[g][1,2,4]triazolo[3,4-a]isoquinolin-3(2H)-one | LRMS m/z (M + H) 313.1 found, 312.3 required. |
| 7-13 | 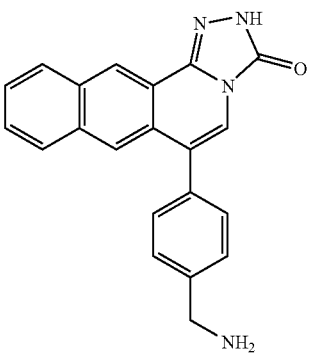 | 6-[4-(aminomethyl)phenyl]benzo[g][1,2,4]triazolo[3,4-a]isoquinolin-3(2H)-one | LRMS m/z (M + H) 341.1 found, 340.4 required. |
| 7-14 | 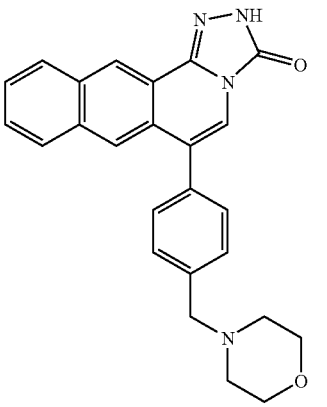 | 6-[4-(morpholin-4-ylmethyl)phenyl]benzo[g][1,2,4]triazolo[3,4-a]isoquinolin-3(2H)-one | LRMS m/z (M + H) 411.1 found, 410.2 required. |
| 7-15 | 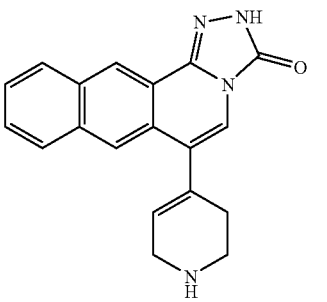 | 6-(1,2,3,6-tetrahydro-4-pyridinyl)-benzo[g]-1,2,4-triazolo[3,4-a]isoquinolin-3(2H)-one | LRMS m/z (M + H) 317.1 found, 316.3 required. |

TABLE 5-continued

| 7-16 | 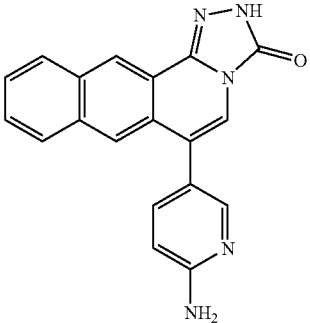 | 6-(6-aminopyridin-3-yl)benzo[g][1,2,4]triazolo[3,4-a]isoquinolin-3(2H)-one | LRMS m/z (M + H) 328.1 found, 327.3 required. |
| 7-17 | 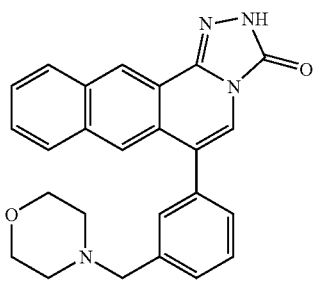 | 6-[3-(morpholin-4-ylmethyl)phenyl]benzo[g][1,2,4]triazolo[3,4-a]isoquinolin-3(2H)-one | LRMS m/z (M + H) 411.0 found, 410.5 required. |
| 7-18 | 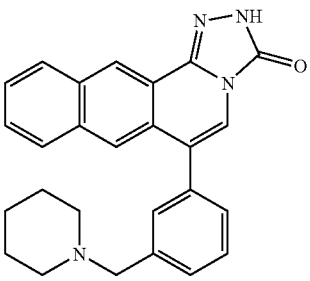 | 6-[3-(piperidin-1-ylmethyl)phenyl]benzo[g][1,2,4]triazolo[3,4-a]isoquinolin-3(2H)-one | LRMS m/z (M + H) 409.0 found, 408.5 required. |
| 7-19 | 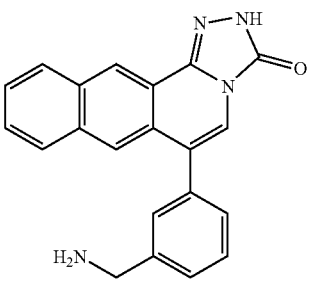 | 6-[3-(aminomethyl)phenyl]benzo[g][1,2,4]triazolo[3,4-a]isoquinolin-3(2H)-one | LRMS m/z (M + H) 341.1 found, 340.4 required. |
| 7-20 | 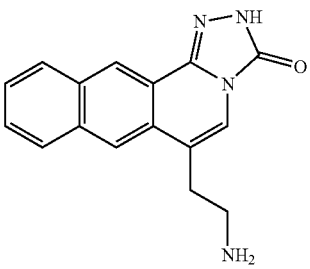 | 6-(2-aminoethyl)benzo[g][1,2,4]triazolo[3,4-a]isoquinolin-3(2H)-one | LRMS m/z (M + H) 279.0 found, 278.3 required. |

TABLE 5-continued

| | | | |
|---|---|---|---|
| 7-21 | | 6-isoquinolin-5-ylbenzo[g][1,2,4]triazolo[3,4-a]isoquinolin-3(2H)-one | LRMS m/z (M + H) 363.1 found, 362.4 required. |
| 7-22 | | 6-quinolin-5-ylbenzo[g][1,2,4]triazolo[3,4-a]isoquinolin-3(2H)-one | LRMS m/z (M + H) 363.1 found, 362.4 required. |
| 7-23 | | 6-(3-aminophenyl)benzo[g][1,2,4]triazolo[3,4-a]isoquinolin-3(2H)-one | LRMS m/z (M + H) 327.1 found, 326.4 required. |
| 7-24 | | 6-piperidin-4-ylbenzo[g][1,2,4]triazolo[3,4-a]isoquinolin-3(2H)-one | LRMS m/z (M + H) 319.2 found, 318.4 required. |
| 7-25 | | 2,2,2-trifluoro-N-[4-(3-oxo-2,3-dihydrobenzo[g][1,2,4]triazolo[3,4-a]isoquinolin-6-yl)phenyl]acetamide | LRMS m/z (M + H) 423.0 found, 422.4 required. |

TABLE 5-continued

| | | | |
|---|---|---|---|
| 7-26 | | 6-(4-aminophenyl)benzo[g][1,2,4]triazolo[3,4-a]isoquinolin-3(2H)-one | LRMS m/z (M + H) 327.1 found, 326.4 required. |
| 7-27 | | 6-pyridin-4-ylbenzo[g][1,2,4]triazolo[3,4-a]isoquinolin-3(2H)-one | LRMS m/z (M + H) 313.0 found, 312.31 required. |
| 7-28 | | 6-(3-aminopropyl)-10-methylbenzo[g][1,2,4]triazolo[3,4-a]isoquinolin-3(2H)-one | LRMS m/z (M + H) 307.2 found, 306.2 required. |
| 7-29 | | 6-(3-aminopropyl)-10-fluorobenzo[g][1,2,4]triazolo[3,4-a]isoquinolin-3(2H)-one | LRMS m/z (M + H) 311.0 found, 311.1 required. |
| 7-30 | | 6-(3-aminopropyl)-9,11-difluorobenzo[g][1,2,4]triazolo[3,4-a]isoquinolin-3(2H)-one | LRMS m/z (M + H) 328.9 found, 329.1 required. |
| 7-31 | | tert-butyl [(2Z)-3-(10-methyl-3-oxo-2,3-dihydrobenzo[g][1,2,4]triazolo[3,4-a]isoquinolin-3(2H)-one | LRMS m/z (M + H) 405.1 found, 405.2 required. |

TABLE 5-continued

| | | | |
|---|---|---|---|
| 7-32 | | 6-[(1Z)-3-aminoprop-1-en-1-yl]-10-methylbenzo[g][1,2,4]triazolo[3,4-a]isoquinolin-3(2H)-one | LRMS m/z (M + H) 306.0 found, 306.1 required. |
| 7-33 | | 6-[(1Z)-3-aminoprop-1-en-1-yl]-10-chlorobenzo[g][1,2,4]triazolo[3,4-a]isoquinolin-3(2H)-one | LRMS m/z (M + H) 326.0 found, 326.1 required. |
| 7-34 | | 6-[4-(aminomethyl)phenyl]-10-methylbenzo[g][1,2,4]triazolo[3,4-a]isoquinolin-3(2H)-one | LRMS m/z (M + H) 356.0 found, 356.2 required. |
| 7-35 | | 6-(3-aminopropyl)-10-chlorobenzo[g][1,2,4]triazolo[3,4-a]isoquinolin-3(2H)-one | LRMS m/z (M + H) 328.0 found, 328.1 required. |
| 7-36 | | 6-[(1Z)-3-aminoprop-1-en-1-yl]-9,10-difluorobenzo[g][1,2,4]triazolo[3,4-a]isoquinolin-3(2H)-one | LRMS m/z (M + H) 327.9 found, 328.1 required. |
| 7-37 | | 6-(3-aminopropyl)-9,10-difluorobenzo[g][1,2,4]triazolo[3,4-a]isoquinolin-3(2H)-one | LRMS m/z (M + H) 330.9 found, 330.1 required. |

TABLE 5-continued
| | | |
|---|---|---|
| 7-38 | 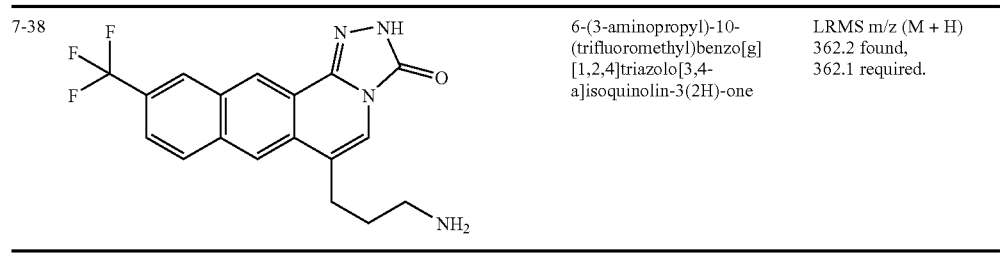 | 6-(3-aminopropyl)-10-(trifluoromethyl)benzo[g][1,2,4]triazolo[3,4-a]isoquinolin-3(2H)-one | LRMS m/z (M + H) 362.2 found, 362.1 required. |
SCHEME 8
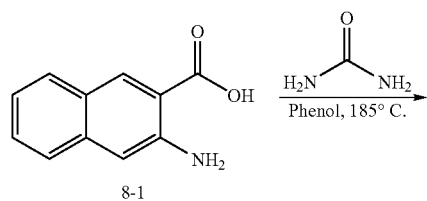
8-1
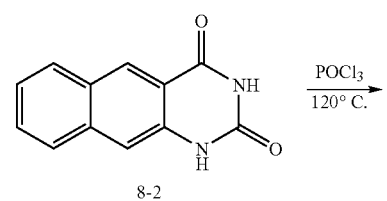
8-2
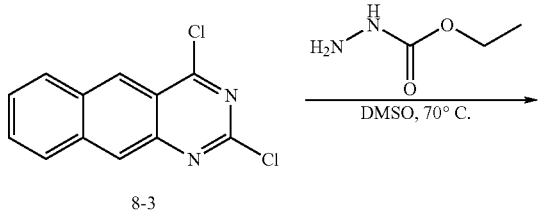
8-3
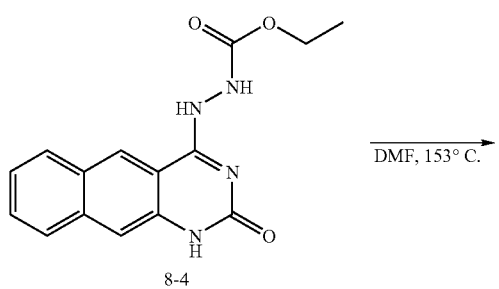
8-4
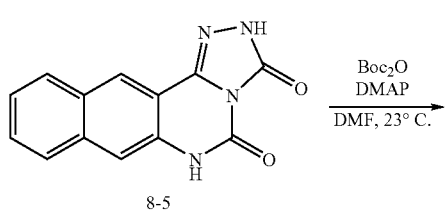
8-5
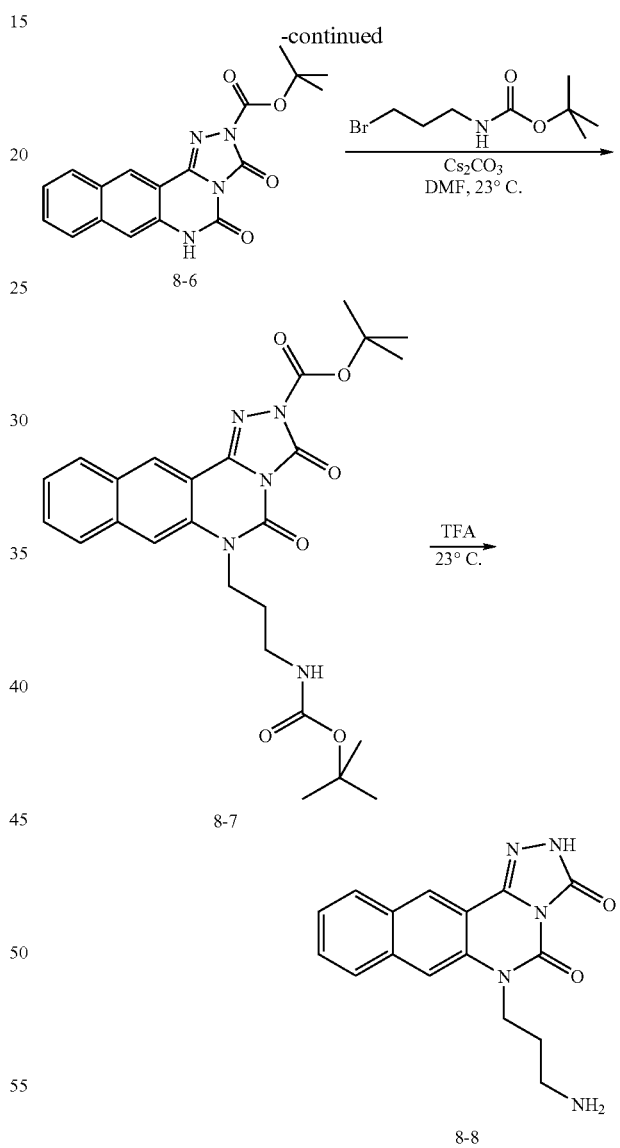
6-(3-aminopropyl)-2,6-dihydrobenzo[g][1,2,4]triazolo[4,3-c]quinazoline-3,5-dione (8-8)
Benzo[g]quinazoline-2,4(1H,3H)-dione (8-2)
A mixture of 3-amino-2-naphthoic acid (8-1, 1.2 g, 6.6 mmol, 1 equiv), urea (2.0 g, 33 mmol, 5.0 equiv) and phenol (7.0 g, 74 mmol, 11 equiv) was heated at 160° C. for 0.5 h an 185° C. for an additional 1.5 h. The reaction was cooled and triturated with methanol (50 mL). The solid precipitate was filtered, washed with methanol, and dried to yield benzo[g]quinazoline-2,4(1H,3H)-dione (1-2) as an orange solid. LRMS m/z (M+H) 213.1 found, 213.1 required.

2.4-dichlorobenzo[g]quinazoline (8-3)

A solution of benzo[g]quinazoline-2,4(1H,3H)-dione (1-2, 1.0 g, 4.9 mmol, 1 equiv) in phosphorus oxychloride (10 mL) was heated at 120° C. for 12 h. The reaction was cooled, and poured into ice water. The precipitate was collected by filtration and purified by silica gel chromatography (methylene chloride) to yield 2,4-dichlorobenzo[g]quinazoline (8-3) as a yellow solid. LRMS m/z (M+H) 249.0 found, 249.0 required.

Ethyl 2-(2-oxo-1,2-dihydrobenzo[g]quinazolin-4-yl) (8-4)

A solution of 2,4-dichlorobenzo[g]quinazoline (8-3, 110 mg, 0.43 mmol, 1 equiv) and ethyl carbazate (69 mg, 0.66 mmol, 1.5 equiv) in DMSO (7 mL) was heated at 70° C. for 2 h. The reaction was cooled and poured into ice water. The precipitate was collected by filtration, suspended in n-butanol (20 mL), and heated at 90° C. for 4 h. The resulting precipitate was collected and dried to yield ethyl 2-(2-oxo-1,2-dihydrobenzo[g]quinazolin-4-yl) (8-4) as an orange solid. LRMS m/z (M+H) 299.1 found, 299.1 required.

2,6-Dihydrobenzo[g][1,2,4]triazolo[4,3-c]quinazoline-3,5-dione (8-5)

A solution of ethyl 2-(2-oxo-1,2-dihydrobenzo[g]quinazolin-4-yl) (8-4, 42 mg, 0.14 mmol, 1 equiv) in DMF (5 mL) was heated at 153° C. for 4 h. The reaction was cooled and poured into ice water. The solid precipitate was collected by filtration and dried to yield 2,6-dihydrobenzo[g][1,2,4]triazolo[4,3-c]quinazoline-3,5-dione (8-5) as an off-white solid. $^1$H NMR (500 MHz, DMSO-d$_6$)) δ 12.30 (s, 1H), 11.36 (s, 1H), 8.53 (s, 1H), 8.05 (d, 1H, J=8.0 Hz), 7.88 (d, 1H, J=8.0 Hz), 7.55 (t, 1H, J=7.5 Hz), 7.52 (s, 1H), 7.46 (t, 1H, J=7.5 Hz). LRMS m/z (M+H) 253.0 found, 253.1 required.

tert-Butyl 3,5-dioxo-5,6-dihydrobenzo[g][1,2,4]triazolo[4,3-c]quinazoline-2(3H)-carboxylate (8-6)

To a mixture 2,6-dihydrobenzo[g][1,2,4]triazolo[4,3-c]quinazoline-3,5-dione (8-5, 20 mg, 0.08 mmol, 1 equiv) and Boc$_2$O (20 mg, 0.09 mmol, 1 equiv) in DMF (3 mL) at 23° C. the residue was washed with ether to give tert-butyl 3,5-dioxo-5,6-dihydrobenzo[g][1,2,4]triazolo[4,3-c]quinazoline-2(3H)-carboxylate (8-6) as a white solid. LRMS m/z (M+H) 353.1 found, 353.1 required.

tert-Butyl 6-{3-[(tert-butoxycarbonyl)amino]propyl}-3,5-dioxo-5,6-dihydrobenzo[g][1,2,4]triazolo[4,3-c]quinazoline-2(3H)-carboxylate (8-7)

A mixture of tert-butyl 3,5-dioxo-5,6-dihydrobenzo[g][1,2,4]triazolo[4,3-c]quinazoline-2(3H)-carboxylate (8-6, 28 mg, 0.079 mmol, 1 equiv), cesium carbonate (100 mg, 0.31 mmol, 3.8 equiv), and N-(3-bromopropyl)carbamic acid tert-butyl ester (50 mg, 0.21 mmol, 2.6 equiv) in DMF (3 mL) was stirred at 23° C. for 16 h. The reaction mixture was filtered and the filtrate was concentrated and purified by reverse phase liquid chromatography (H$_2$O/CH$_3$CN gradient w/0.1% TFA present) to yield tert-butyl 6-{3-[(tert-butoxycarbonyl)amino]propyl}-3,5-dioxo-5,6-dihydrobenzo[g][1,2,4]triazolo[4,3-c]quinazoline-2(3H)-carboxylate (8-7).

6-(3-aminopropyl)-2,6-dihydrobenzo[g][1,2,4]triazolo[4,3-c]quinazoline-3,5-dione (8-8)

To a solution of tert-butyl 6-{3-[(tert-butoxycarbonyl)amino]propyl}-3,5-dioxo-5,6-dihydrobenzo[g][1,2,4]triazolo[4,3-c]quinazoline-2(3H)-carboxylate (8-7, 5 mg, 0.01 mmol, 1 equiv) in a 1:1 mixture of water and acetonitrile was added trifluoroacetic acid (3 mL) and the resulting solution was stirred at 45° C. for 2 h. The solvent was evaporated under reduced pressure to yield the TFA salt of 6-(3-aminopropyl)-2,6-dihydrobenzo[g][1,2,4]triazolo[4,3-c]quinazoline-3,5-dione (8-8) as a white solid. $^1$H NMR (500 MHz, DMSO-d6, TFA Salt) δ 12.37 (s, 1H), 8.62 (s, 1H), 8.10 (d, 1H, J=8.5 Hz), 8.00 (d, 1H, J=8.0 Hz), 7.93 (s, 1H), 7.77 (br s, 1H), 7.63 (t, 1H, J=7.5 Hz), 7.52 (t, 1H, 7.5 Hz), 4.26 (t, 2H, J=7.0 Hz), 3.02 (m, 2H), 2.05 (m, 2H). LRMS m/z (M+H) 310.1 found, 310.1 required.

The following compounds in Table 6 were prepared as TFA salts following similar procedures in Scheme 8.

TABLE 6

| Cmp | Structure | Name | LRMS m/z (M + H) |
|---|---|---|---|
| 8-9 | 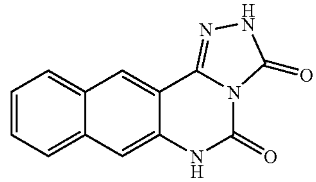 | 2,6-dihydro benzo[g][1,2,4]triazolo[4,3-c]quinazoline-3,5-dione | LRMS m/z (M + H) 253.0 found, 253.1 required. |

TABLE 6-continued

| Cmp | Structure | Name | LRMS m/z (M + H) |
|---|---|---|---|
| 8-10 | 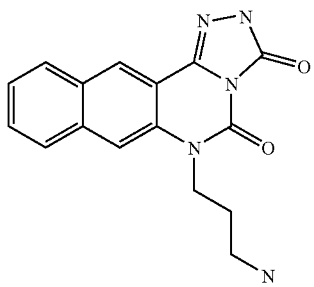 | 6-(3-aminopropyl)-2,6-dihydrobenzo[g][1,2,4]triazolo[4,3-c]quinazoline-3,5-dione | LRMS m/z (M + H) 310.1 found, 310.1 required. |

Examples 1-8

Examples are provided below to further illustrate different features and advantages of the present invention. The examples also illustrate useful methodology for practicing the invention. These examples do not limit the claimed invention.

Example 1

Identification of CHK1sv1 Using Real-time PCR

To facilitate the determination of compound inhibitory properties, it is desirable to identify variants of the "normal" splicing of exon regions encoding CHK1. In particular, naturally occurring splicing variations resulting in the loss of the C-terminal regulatory domain of CHK1 were sought. Deletion of the C-terminus confers greater kinase activity to CHK1 (Chen et al., 2000, Cell 100:681-692; Katsuragi and Sagata, 2004, Mol. Biol. Cell. 15:1680-1689). Exons 2-8 encode the catalytic kinase domain and exon 9 encodes the linker region. The SQ and C-terminal regulatory domains lie within exons 10-13 (Sanchez et al., 1997, 277:1497-1501; Katsuragi and Sagata, 2004, Mol. Biol. Cell. 15:1680-1689). Real-time PCR experiments and RT-PCR have been used to identify and confirm the presence of novel splice variants of human CHK1 mRNA. A naturally occurring splice variant which encodes a C-terminal truncation of the CHK1 inhibitory domain was identified, cloned, expressed and purified for use in a CHK1 kinase assay of utility for the determination of compound inhibitory properties.

RT-PCR

The structure of CHK1 mRNA in the region corresponding to exons 8 to 11 was determined for RNA extracted from human testis using an RT-PCR based assay. Total RNA isolated from human testis was obtained from BD Biosciences Clontech (Palo Alto, Calif.). RT-PCR primers were selected that were complementary to sequences in exon 8 and exon 11 of the reference exon coding sequences in CHK1 (NM_001274). Based upon the nucleotide sequence of CHK1 mRNA, the CHK1 exon 8 and exon 11 primer set (hereafter CHK1$_{8-11}$ primer set) was expected to amplify a 478 base pair amplicon representing the "reference" CHK1 mRNA region. The CHK1$_{8-11}$ primer set was expected to amplify a 300 base pair amplicon in a transcript that possessed alternative splicing of exon 9 to exon 11. The CHK1 exon 8 forward primer has the sequence: 5' ATCAGCAAGAATTACCATTCCAGACATC 3' (SEQ ID NO 1); and the CHK1 exon 11 reverse primer has the sequence: 5' CATACAACTTTTCTTCCATTGATAGCCC 3' (SEQ ID NO 2).

Total RNA from human testis was subjected to a one-step reverse transcription-PCR amplification protocol using the Qiagen, Inc. (Valencia, Calif.), One-Step RT-PCR kit, using the following cycling conditions:

1) 50° C. for 30 minutes;
2) 95° C. for 15 minutes;
3) 35 cycles of:
94° C. for 30 seconds;
63.5° C. for 40 seconds;
72° C. for 50 seconds; then
72° C. for 10 minutes.

RT-PCR amplification products (amplicons) were size fractionated on a 2% agarose gel. Selected fragments representing 250 to 350 base pair amplicons were manually extracted from the gel and purified with a Qiagen Gel Extraction Kit. The purified amplicon fragments were reamplified with the CHK1$_{8-11}$ primer set, and these amplicons were size fractionated on an agarose gel. Fragments representing 250 to 350 base pair amplicons were manually extracted from the gel and purified with a Qiagen Gel Extraction Kit. The purified amplicon fragments were reamplified with the CHK1$_{8-11}$ primer set once more. Following size fractionation on an agarose gel and manual extraction of the 250 to 350 base pair amplicons, the purified amplicon fragments (Qiagen Gel Extraction Kit) were cloned into an Invitrogen pCR2.1 vector using the reagents and instructions provided with the TOPO TA cloning kit (Invitrogen, Carlsbad, Calif.). Clones were then plated in pools of 440 colonies per plate, onto 15 plates, for a total of 6600 clones. DNA was extracted from the pooled 440 colonies from each plate and used as template for real-time PCR.

Real-time PCR/TAQman

To determine the presence of an alternatively spliced isoform to the CHK1 reference protein (NP_001265), a real-time PCR assay was used.

TAQman primers and probes used to detect the CHK1sv1 isoform were designed and synthesized as pre-set mixtures (Applied Biosystems, Foster City, Calif.). The sequences of the TAQman primers and probes used to detect the CHK1 reference form (SEQ ID NOs 3, 4, and 5) and CHK1sv1 isoform (SEQ ID NOs 6, 7, and 8) are shown in Table 1. Splice junction specific probes were labeled with the 6-FAM fluorophore at the 5' end (FAM) and a non-fluorescent quencher at the 3' end (NFQ). Real-time PCR was performed on human testis cDNA using the TaqMan Universal PCR Master Mix (Applied Biosystems, Foster City, Calif.). The TAQman reaction contained:

| 96-well format | 384-well format | |
|---|---|---|
| 12.5 µl | 5 µl | TAQman Universal MasterMix |
| 1.25 µl | 0.5 µl | Primer-probe mix |
| 6.25 µl | 2.5 µl | H₂O |
| 5 µl | 2 µl | DNA |

TABLE 1

Primers and probes used to detect CHK1 isoforms.

| Name | SEQ ID NO | Sequence | Specificity |
|---|---|---|---|
| CHK1 reference forward primer | SEQ ID NO 3 | GTTACTTGGCACCCCAGGA | CHK1 reference |
| CHK1 reference reverse primer | SEQ ID NO 4 | CATCCAATTTGGTAAAGAATCGTGTCA | CHK1 reference |
| CHK1 reference probe | SEQ ID NO 5 | FAM-TCCTCACAGAACCCC-NFQ | CHK1 reference |
| CHK1sv1 forward primer | SEQ ID NO 6 | GCACATTCAATCCAATTTGGACTTCT | CHK1sv1 |
| CHK1sv1 reverse primer | SEQ ID NO 7 | CATCCAATTTGGTAAAGAATCGTGTCAT | CHK1sv1 |
| CHK1sv1 probe | SEQ ID NO 8 | FAM-CAGTGCTTCTAGAACCC-NFQ | CHK1sv1 |

The TAQman reactions were performed on an ABI Prism 7900HT Sequence Detection System (Applied Biosystems, Foster City, Calif.). The thermocycling conditions were 50° C. for 2 minutes, 95° C. for 10 minutes, and 40 cycles of 95° C. for 15 seconds and 60° C. for 1 minute. Data analysis of the fluorescence emission was performed by the Sequence Detector Software (SDS) (Applied Biosystems, Foster City, Calif.).

Results of the TAQman assay indicated that pooled DNA from 13 out of 15 plates appeared to possess clones that represented an alternative exon 9 to exon 11 splice junction. DNA from one of these positive pools, representing 440 colonies, was used to transform bacterial host cells. Clones were plated in pools of 55 colonies per plate onto 12 plates total. The colonies on each of the 12 plates were again pooled and used for a TAQman assay. Pooled DNA from 1 out of 12 plates appeared to possess a clone that represented an alternative exon 9 to exon 11 splice junction. The 55 colonies on this positive plate were individually screened using a TAQman assay, and one clone was identified as possessing an alternative exon 9 to exon 11 splice junction. This positive clone was then sequenced from each end using the CHK1 exon 8 forward primer (SEQ ID NO 1) and a different exon 11 reverse primer with the sequence

5' TGCATCCAATTTGGTAAAGAATCG 3'. (SEQ ID NO 9)

Sequence analysis of the clone revealed that it matched the expected sequence for alternative splicing of exon 9 of the CHK1 heteronuclear RNA to exon 11; that is the coding sequence of exon 10 is completely absent.

Example 2

Cloning of CHK1sv1

Real-time PCR, RT-PCR, and sequencing data indicate that in addition to the normal CHK1 reference mRNA sequence, NM_001274, encoding CHK1 protein, NP_001265, a novel splice variant form of CHK1 mRNA also exist in testis tissue and MOLT-4, and Daudi cell lines.

Clones having a nucleotide sequence comprising the CHK1sv1 splice variant identified in Example 1 were isolated using recombination-mediated plasmid construction in yeast. A set of two primer pairs was used to amplify and clone the entire mRNA coding sequences of CHK1sv1. In the case of CHK1sv1, real-time quantitative PCR analysis indicated that transcripts of this splice variant form were present at very low levels. In order to clone CHK1sv1, clones containing coding sequences of the reference CHK1 (NM_001274) were altered by an additional recombination step in yeast with 80 base pair linkers that were designed to create the desired exon 9 to exon 11 splice junction.

A 5' "forward" primer and a 3' "reverse" primer were designed for isolation of full length clones corresponding to CHK1sv1. The 5' "forward" CHK1sv1 primer was designed to have the nucleotide sequence of 5' TTACTGGCTTATC-GAAATTAATACGACTCACTATAG GGAGGAGTCATG-GCAGTGCCCTTTGT 3' (SEQ ID NO 10) and to have sequences complementary to exon 2 of the CHK1 mRNA (NM_001274). The 3' "reverse" CHK1sv1 primer was designed to have the nucleotide sequence of 5' TAGAAG-GCACAGTCGAGGCTGA TCAGCGGGTTTAAACTCAT-GCATCCAATTTGGTAAAGAATCG 3' (SEQ ID NO 11) and to have sequences complementary to exon 11 of the CHK1 mRNA (NM_001274). The 40 nucleotides at the 5' ends of the primer sequences indicated in italics are "tails" that were incorporated into the PCR amplicons and facilitated subsequent plasmid recombination events in yeast. These CHK1sv1 "forward" and "reverse" primers were expected to amplify coding sequences of the reference CHK1 mRNA (NM_001274), which was then used in a subsequent recombinational cloning step to create CHK1sv1-specific sequence.

RT-PCR

The CHK1sv1 cDNA sequence was cloned using a combination of reverse transcription (RT) and polymerase chain reaction (PCR). More specifically, about 25 ng of MOLT-4 cell line mRNA (BD Biosciences Clontech, Palo Alto, Calif.) was reverse transcribed using Superscript II (Gibco/Invitrogen, Carlsbad, Calif.) and oligo d(T) primer (RESGEN/Invitrogen, Huntsville, Ala.) according to the Superscript II manufacturer's instructions. For PCR, 1 µl of the completed RT reaction was added to 40 µl of water, 5 µl of 10× buffer, 1 µl of dNTPs and 1 µl of enzyme from a Clontech (Palo Alto, Calif.) Advantage 2 PCR kit. PCR was done in a Gene Amp PCR System 9700 (Applied Biosystems, Foster City, Calif.) using the CHK1sv1 "forward" and "reverse" primers for CHK1sv1 (SEQ ID NOs 10,11). After an initial 94° C. denaturation of 1 minute, 35 cycles of amplification were performed using a 30 second denaturation at 94° C. followed by a 40 second annealing at 63.5° C. and a 50 second synthesis at 72° C. The 35 cycles of PCR were followed by a 10 minute extension at 72° C. The 50 µl reaction was then chilled to 4° C. 10 µl of the resulting reaction product was run on a 1% agarose (Invitrogen, Ultra pure) gel stained with 0.3 µg/ml ethidium bromide (Fisher Biotech, Fair Lawn, N.J.). Nucleic acid bands in the gel were visualized and photographed on a UV light box to determine if the PCR had yielded products of the expected size, in the case of the CHK1 mRNA, a product of about 1243 base pairs. The remainder of the 50 µl PCR reactions from MOLT-4 cells was purified using the QIAquik Gel extraction Kit (Qiagen, Valencia, Calif.) following the QIAquik PCR Purification Protocol provided with the kit. About 50 µl of product obtained from the purification protocol was concentrated to about 6 µl by drying in a Speed Vac Plus (SC110A, from Savant, Holbrook, N.Y.) attached to a Universal Vacuum System 400 (also from Savant) for about 30 minutes on medium heat.

Cloning and Assembly of CHK1sv1 Full-length Clones and Yeast Transformation

Assembly of the full length CHK1sv1 clone by homologous recombination cloning in yeast was performed using a cycloheximide-based counterselection scheme similar to that described previously by Raymond et al. (2002, *Genome Res.* 12:190-197).

Assembly of the full-length CHK1sv1 full length clone by homologous recombination between the 1243 base pair CHK1 amplicon, produced using the CHK1sv1 forward and reverse "tailed" primers described earlier, and the expression vector was performed by simultaneous transformation of these pieces into yeast cells. A subsequent recombination step with 80 base pair oligonucleotide linkers created the CHK1sv1 exon 9 to exon 11 splice junction. All yeast transformation steps described in subsequent paragraphs were performed by electroporation (Raymond et al., 2002 *Genome Res.* 12:190-197).

1 µg of the 1243 base pair CHK1 purified amplicon was cloned directly into 100 ng of SrfI-digested pCMR11 by cotransformation of 100 µl of yeast strain CMY1-5 (Matα, URA3Δ, CYH2$^R$). Ura$^+$, cycloheximide resistant colonies were selected on Ura-deficient media plates containing 1 µg/ml cycloheximide (Sigma, St. Louis, Mo.). Standard yeast media were used (Sherman, 1991, *Methods Enzymol.* 194:3-21). Total DNA from yeast cell culture containing the CHK1 clone was used to transform *E. coli* to chloramphenicol (Sigma, St. Louis, Mo.) resistance to prepare a large quantity of the recombinant plasmid as described in Hoffman and Winston (1987 Gene 57:267-72). The colonies were picked from the plates into 2 ml of 2× LB media. These liquid cultures were incubated overnight at 37° C. Plasmid DNA was extracted from these cultures using the Qiagen (Valencia, Cailf.) Qiaquik Spin Miniprep kit.

TABLE 2

Composition of pCMR11 plasmid

| Nucleotide coordinates | Functional description of sequence |
|---|---|
| 1-6013 | Copy-control ™ *E. coli* origin of replication from pCC1FOS (Epicentre Technologies, Madison, WI). |
| 6014-7884 | Yeast URA3 gene, ARS4 autonomously replicating sequence and CEN6 centromere from pRS316 (Sikorski and Hieter, 1989). |
| 7885-8825 | Mammalian CMV promoter from InVitrogen (Carlsbad, CA) vector pcDNA3.1/myc-HIS A. |
| 8826-10,774 | Yeast CYH2 gene amplified from strain BY4709 (Brachmann et al. 1998) |
| 10,775-10,782 | Engineered SrfI restriction site. |
| 10,783-13,556 | Mammalian poly-adenylation sites, selectable markers, SV40 origin, etc. from pcDNA3.1/myc-HIS A. |
| 13,557-13,596 | DNA sequence from InVitrogen vector pENTR11. |
| 13,597-14,561 | pCMR11 - specific; chloramphenicol resistance gene from pCC1FOS. |

To construct the CHK1sv1 clone, 1 µg of 80 base pair linkers shown in Table 3 (SEQ ID NOs 12, 13) that spans the region of the alternative splicing of exon 9 to exon 11, and 100 ng of BamHI-digested CHK1/pCMR11 clone were used to cotransform 100 µl of a cycloheximide sensitive yeast strain. The overlapping DNA between the linkers and CHK1/pCMR 11 clone dictates that most yeast transformants will possess the correctly assembled construct. Ura$^+$, cycloheximide resistant colonies were selected for subsequent preparation and transformation of *E. coli*. Plasmid DNA extracted from *E. coli* was analyzed by restriction digest to confirm the presence of the alternative splicing of exon 9 to exon 11 in the CHK1sv1 clone. Eight CHK1sv1 clones were sequenced to confirm identity, and the clones possessing the appropriate sequences are used for protein expression in multiple systems.

TABLE 3

Linkers used to create exon 9 to exon 11 splice junction for CHK1sv1 clone

| SEQ ID NO | Linker Sequence |
|---|---|
| SEQ ID NO 12 | AATCCAATTTGGACTTCTCTCCAGTAAACAGTGCTTCTAGAACC CCTGGCAGCGGTTGGTCAAAAGAATGACACGATTCT |
| SEQ ID NO 13 | AGAATCGTGTCATTCTTTTGACCAACCGCTGCCAGGGGTTCTAG AAGCACTGTTTACTGGAGAGAAGTCCAAATTGGATT |

Summary of CHK1sv1 Polynucleotide

The polynucleotide coding sequence of CHK1sv1 mRNA (Seq ID NO 14) contains an open reading frame that encodes a CHK1sv1 protein (SEQ ID NO 15) similar to the reference CHK1 protein (NP_001265), but lacking amino acids encoded by a 178 base pair region corresponding to exons 10 of the full length coding sequence of reference CHK1 mRNA (NM_001274). The deletion of the 178 base pair region results in a shift of the protein translation reading frame in comparison to the reference CHK1 protein reading frame, creating a carboxy terminal peptide region that is unique to CHK1sv1 (italicized in Seq ID NO 15). The frameshift also creates a premature termination codon 29 nucleotides downstream of the exon 9/exon 11 splice junction. Therefore, the CHK1sv1 protein is missing an internal 59 amino acid region corresponding to the amino acid region encoded by exon 10 and is also lacking the amino acids encoded by the nucleotides downstream of the premature stop codon as compared to the reference CHK1 (NP_001265). Exon 10 encodes the SQ/TQ domains of CHK1, and exons 11-13 encode the autoinhibitory region (Sanchez et al., 1997, *Science* 277:1497-1501; Katsuragi and Sagata, 2004, *Mol. Biol Cell*. 15:1680-1689). While deletion of the autoinhibitory region confers constitutive activity to the CHK1 kinase domain, when the SQ/TQ domains are also removed, CHK1 enzymatic activity decreases (Ng et al., 2004, *J. Biol. Chem*. 279:8808-8819).

the amplicon. The primer represented by SEQ ID NO 17 contains sequence encoding six histidine residues C-terminal to the CHK1sv1 coding sequence as well as an EagI restriction site that become incorporated into the CHK1sv1amplicon. The CHK1sv1 amplicon was run on a 1% agarose gel. A selected amplicon fragment of the expected size, in the case of CHK1sv1, a product of about 994 base pairs, was manually extracted from the gel and purified with a Qiagen Gel Extraction Kit. The purified amplicon fragment was digested with EcoRI and EagI. The EcoRI/EagI-digested amplicon was ligated into the baculovirus transfer vector pVL1393 (Pharmingen, San Diego, Calif.)

TABLE 4

Nucleotide coding sequence and coded polypeptide for CHK1sv1

Seq ID NO 14  ATGGCAGTGCCCTTTGTGGAAGACTGGGACTTGGTGCAAACCCTGGG
AGAAGGTGCCTATGGAGAAGTTCAACTTGCTGTGAATAGAGTAACTG
AAGAAGCAGTCGCAGTGAAGATTGTAGATATGAAGCGTGCCGTAGAC
TGTCCAGAAAATATTAAGAAAGAGATCTGTATCAATAAAATGCTAAA
TCATGAAAATGTAGTAAAATTCTATGGTCACAGGAGAGAAGGCAATA
TCCAATATTTATTTCTGGAGTACTGTAGTGGAGGAGAGCTTTTTGACA
GAATAGAGCCAGACATAGGCATGCCTGAACCAGATGCTCAGAGATTC
TTCCATCAACTCATGGCAGGGGTGGTTTATCTGCATGGTATTGGAATA
ACTCACAGGGATATTAAACCAGAAAATCTTCTGTTGGATGAAAGGGA
TAACCTCAAAATCTCAGACTTTGGCTTGGCAACAGTATTTCGGTATAA
TAATCGTGAGCGTTTGTTGAACAAGATGTGTGGTACTTTACCATATGT
TGCTCCAGAACTTCTGAAGAGAAGAGAATTTCATGCAGAACCAGTTG
ATGTTTGGTCCTGTGGAATAGTACTTACTGCAATGCTCGCTGGAGAAT
TGCCATGGGACCAACCCAGTGACAGCTGTCAGGAGTATTCTGACTGG
AAAGAAAAAAAAACATACCTCAACCCTTGGAAAAAAATCGATTCTGC
TCCTCTAGCTCTGCTGCATAAAATCTTAGTTGAGAATCCATCAGCAAG
AATTACCATTCCAGACATCAAAAAAGATAGATGGTACAACAAACCCC
TCAAGAAAGGGGCAAAAAGGCCCCGAGTCACTTCAGGTGGTGTGTCA
GAGTCTCCCAGTGGATTTTCTAAGCACATTCAATCCAATTTGGACTTCT
CTCCAGTAAACAGTGCTTCTAGAACCCCTGGCAGCGGTTGGTCAAAAG
AATGA

Seq ID NO 15  MAVPFVEDWDLVQTLGEGAYGEVQLAVNRVTEEAVAVKIVDMKRAVD
CPENIKKEICINKMLNHENVVKFYGHRREGNIQYLFLEYCSGGELFDRIEP
DIGMPEPDAQRFFHQLMAGVVYLHGIGITHRDIKPENLLLDERDNLKISDF
GLATVFRYNNRERLLNKMCGTLPYVAPELLKRREFHAEPVDVWSCGIVL
TAMLAGELPWDQPSDSCQEYSDWKEKKTYLNPWKKIDSAPLALLHKILV
ENPSARITIPDIKKDRWYNKPLKKGAKRPRVTSGGVSESPSGFSKHIQSNL
DFSPVNSAS *RTPGSGWSKE*

Example 3

Expression of CHK1 sv1 Protein

The baculovirus gene expression vector system permits protein expression insect cells, which are inexpensive and easy to maintain. The proteins produced are of similar quality to that in mammalian cells (Miller, 1988, *Biotechnology* 10:457-465; Miller, 1989, *Bioessays* 11:91-95). Methods of protein expression using the baculovirus expression vectors in insect cells are known in the art and techniques are discussed in O'Reilly et al., *Baculovirus Expression Vectors—A Laboratory Manual*, W. H. Freeman and Co., New York, 1992 and *Baculovirus Expression Vector System Instruction Manual*, 6th edition, Pharmingen, San Diego, 1999.

Cloning CHK1sv1 for Insect Cell Expression

To create a CHK1sv1/baculovirus transfer vector construct, the CHK1sv1/pCMR11 clone (see Example 2) was used as template for PCR to amplify the coding sequence of CHK1sv1 (SEQ ID NO 14) using the primers listed in Table 5 (SEQ ID NOs 16, 17). The primer represented by SEQ ID NO 16 contains an optimal translation initiation sequence immediately upstream of the ATG start codon and an upstream EcoRI restriction site that become incorporated into which had been digested with EcoRI and EagI and dephosphorylated with alkaline phosphatase. The CHK1sv1/pVL1393 construct was then transformed into *E. coli* strain DH5α. Plasmid DNA extracted from selected from ampicillin resistant colonies was sequenced to confirm identity, and the clones possessing the appropriate sequences were used for protein expression in insect cells.

TABLE 5

Primers used to clone CHK1sv1 into *baculovirus* transfer vector pVL1393

| SEQ ID NO | Primer Sequence |
|---|---|
| SEQ ID NO 16 | CCCGGAATTCACCATGGCAGTGCCCTTTGTGGAAGACTGG |
| SEQ ID NO 17 | TGTGTCCGGCCGTCAGTGATGGTGATGGTGATGTTCTTTTGACC AACCGCTGCC |

Insect Cell Expression of CHK1sv1

The CHK1sv1/pVL1393 construct was co-transfected with linearized AcNPV BaculoGold DNA (Pharmingen, San Diego, Calif.) into SF9 insect cells (Invitrogen, Carlsbad, Calif.). Individual recombinant viruses were selected by end point dilution. Virus clones were amplified to obtain high titer stocks. These virus stocks were used for protein expression tests in small scale SF9 cultures to verify production of the CHK1sv1 recombinant protein. Transfected SF9 cell lysates were analyzed by polyacrylamide gel electrophoresis for CHK1sv1 protein expression. The CHK1sv1 protein was visualized by Commassie staining or by Western blotting using an anti-CHK1 antibody (G4 antibody; Santa Cruz Biotechnology, Inc). Based on expression, an individual virus was selected for larger scale CHK1sv1 expression. For recombinant protein expression on the liter scale, SF9 suspension cultures were grown at 27° C. in Ex-cell 401 serum-free media (JRH Scientific, Lenexa, Kans.) and were infected with a recombinant virus stock using a multiplicity of infection of 0.3 virus per cell. The infected SF9 culture was harvested 72 hour following virus transfection, and pelleted by centrifugation. Pellets were stored at −70° C.

Purification of CHK1 sv1 Recombinant Protein

Insect cell pellets were lysed with B-PER protein extraction reagent (Pierce, Rockford, Ill.) containing 1 µM microcystin (Sigma, St. Louis, Mo.), 10 µM cypermethrin (EMD Biosciences, San Diego, Calif.), and EDTA-free Protease Inhibitor Cocktail (Roche Diagnostics, Mannheim, Germany) (1 tablet/50 ml lysis buffer). All manipulations during protein purification were performed at 4° C. Cells were resuspended in the lysis buffer were stirred for 45 minutes. DNAseI (Roche) was then added to a final concentration of 200 U/ml and the cell suspension was stirred for an additional 30 minutes. The lysed cell suspension was centrifuged for 30 minutes at 30,000 g. The lysis supernatant was decanted and centrifuged for 30 minutes at 30,000 g. For each 10 ml of cleared supernatant, 1 ml bed volume of Talon metal affinity resin (Clontech, Palo Alto, Calif.) was added, and the suspension was stirred for 45 minutes. The affinity resin/lysate suspension was centrifuged at 5000 g for 3 minutes and then the supernatant. was discarded. The affinity resin was washed 4× with Buffer A (50 µM Tris, pH 8.0; 250 mM NaCl) using 5× volumes of the resin. The washed resin was resuspended as a 2× slurry in Buffer A and packed into a chromatography column. The resin-packed column was washed with 6× bed volumes of Buffer A. CHK1sv1-His-tagged protein is eluted from the column using a step-wise gradient of imidazole in Buffer A. Imidazole concentrations in the 2× bed volumen fractions were 5, 10, 20, 30, 40, 50, and 60 mM. Elution fractions were concentrated using the Amicon Ultra 15 Centrifugal Filter Device, 30,000 Nominal Molecular Weight Limit (Millipore, Billerica, Mass.). The concentrated enzyme fractions were diluted 50% in glycerol and stored at −20° C. Fractions were analyzed for the presence of CHK1sv1-His-tagged protein using polyacrylamide gel electrophoresis followed by Coommassie staining and Western blotting using an anti-CHK1 antibody (G4 antibody; Santa Cruz Biotechnology, Inc). The CHK1sv1 kinase activity of the column fractions was determined using the kinase assay described in the following section.

Example 4

CHK1sv1 Kinase Assay

CHK1 sv1 activity was assayed in vitro using a synthetic peptide substrate. The phosphopeptide product was quantitated using a Homogenous Time-Resolved Fluorescence (HTRF) assay system (Park et al., 1999, *Anal. Biochem.* 269: 94-104). The reaction mixture contained 40 mM HEPES, pH 7.3; 100 mM NaCl; 10 mM MgCl$_2$; 2 mM dithiothreitol; 0.1% BSA; 0.1 mM ATP; 0.5 µM peptide substrate; and 0.1 nM CHK1sv1 enzyme in a final volume of 40 µl. The peptide substrate has the amino acid sequence amino terminus-GGRARTSSFAEPG-carboxy terminus (SynPep, Dublin Calif.) (SEQ ID NO 18) and is biotinylated at the N-terminus. The kinase reaction was incubated for 30 minutes at 22° C., and then terminated with 60 µl Stop/Detection Buffer (40 mM HEPES, pH 7.3; 10 mM EDTA; 0.125% Triton X-100; 1.25% BSA; 250 nM PhycoLink Streptavidin-Allophycocyanin (APC) Conjugate (Prozyme, San Leandro, Calif.); and 0.75 nM GSK3α anti-phosphoserine antibody (Cell Signaling Technologies, Beverly, Mass.; Cat# 9338) labeled with europium-chelate (Perkin Elmer, Boston, Mass.). The reaction was allowed to equilibrate for 2 hours at 22° C., and relative fluorescent units were read on a Discovery plate reader (Packard Biosciences). Inhibitor compounds are assayed in the reaction described above, to determine compound IC50s. 1 µL of compound dissolved in DMSO was added to each 40 µL reaction in a half-log dilution series covering a range of 1 nM to 100 µM. Relative phospho substrate formation, read as HTRF fluorescence units, is measured over the range of compound concentrations and a titration curve generated using a four parameter sigmoidal fit.

Specific compounds of the instant invention were tested in the assay described above and were found to have IC$_{50}$ of $\leq 50$ µM against substrate.

Example 5

Inhibition of CHK1 Autophosphornlation in Cells

Inhibitor compounds are assayed for their ability to inhibit CHK1 in cells by monitoring CHK1 autophosphorylation in response to DNA damage. H1299 cells (ATCC, Manassas, Va.) are grown in culture medium: RPMI 1640 supplemented with 10% fetal bovine serum; 10 mM HEPES; 2 mM L-glutamine; 1× non-essential amino acids; and penicillin-streptomycin. Cells from T-75 flasks are pooled, counted, seeded into 6 well dishes at 200,000 cells per well in 2 ml media, and incubated. Serial dilution series of compounds in DMSO or DMSO control are added to each well from a 1000× working stock in DMSO and incubated for 2 hr at 37° C. Following the 2-hr incubation period, 100 nM camptothecin (EMD Biosciences, San Diego, Calif.) is added from a 200× working stock in PBS to all drug-treated cells (except one of the high dose wells) and one DMSO control well. After a 4 hour incubation with camptothecin, each well is washed once with ice-cold PBS and 300 µL of lysis buffer (50 mM Tris (pH 8.0), 150 mM NaCl, 50 mM NaF, 1% NP-40, 0.5% Deoxycholic acid, 0.1% SDS, 0.5 µM Na$_3$VO$_4$ and 1× Protease Inhibitor Cocktail Complete—without EDTA (Roche Diagnostics, Mannheim, Germany)) is added to each well. Plates are shaken at 4° C. for 10-15 min and lysates are then transferred to 1.5 ml microcentrifuge tubes and frozen at −80° C. Lysates are thawed on ice and cleared by centrifugation at 15,000×g for 20 min and the supernatants are transferred to clean tubes.

Samples (20 µL) are prepared for gel electrophoresis by addition of 5 µL of 5× sample loading buffer and heat-denaturation for 5 min at 100° C. Samples are electorphoresed in Tris/Glycine SDS-polyacrylamide gels (10%) and proteins are transferred onto PVDF. Blots are then blocked for 1 hr in 3% BSA in TBS and probed using an antibody against phos-pho-Ser-296 CHK1 (Cell Signaling Technologies—Cat #2346). Bound antibody is visualized using a horseradish peroxidase conjugated secondary antibody (goat anti-rabbit Jackson Labs—Cat# 111-035-046) and enhanced chemiluminescence (ECL-plus, Amersham, Piscataway, N.J.). After stripping of the first antibody set by incubation in 62.5 mM Tris HCl pH 6.7, 2% SDS and 2-mercaptoethanol to 100 µM for 30 min at 55° C., blots are re-probed for total CHK1, using a CHK1 monoclonal antibody (Santa Cruz Biotechnology Inc., Cat# SC-8408). The CHK1 monoclonal is detected using a a sheep anti-mouse IgG coupled to horseradish peroxidase (Amersham Biosciences, Piscataway, N.J., Cat#NA931) and enhanced chemiluminescence (ECL-plus, Amersham). ECL exposed films are scanned and the intensity of specific bands is quantitated with ImageQuant software. Titrations are evaluated for level of phospho-CHK1 (Ser296) signal normalized to total CHK1 and IC50 values are calculated.

Example 6

Functional Activity of Inhibitors in Checkpoint Escape Assay DNA Damage Arrest

To measure functional activity of CHK1 inhibitors in cells, compounds are assayed for their ability to abrogate DNA damage induced cell cycle arrest. The assay determines cell phospho-nucleolin levels as a measure of the quantity of cells entering M-phase after cell cycle arrest brought on by the DNA damaging agent camptothecin.

H1299 cells (ATCC, Manassas Va.) are seeded at a density of 5000 cells/well in RPMI640 media supplemented with 10% fetal bovine serum. After incubation for 24 hours at 37° C. at 5% $CO_2$, camptothecin is added to a final concentration of 200 nM and incubated for 16 hours. An equal volume of a test compound serial dilution series in growth media plus 200 nM camptothecin and 332 nM nocodozole (final concentration: 50 ng/ml) is added and incubation at 37° C. is continued for 8 hours. Media is removed from the wells and 50 µL lysis buffer (20 mM HEPES, pH7.5, 150 mM NaCl, 50 mM NaF, 1% Triton X-100, 10% Glycerol, 1× Proteinase Inhibitor Cocktail (Roche Diagnostics, Mannheim Germany), 1 µl/ml DNase I (Roche Diagnostics), 300 µM Sodium Orthovanadate, 1 µM Microcystin (Sigma, St. Louis, Mo.) added. The plate with lysis buffer is shaken for 30 min at 4° C. and frozen (−70° C.) for 20 min. Levels of phosphonucleolin in the cell lysates is measured using the IGEN Origen technology (BioVeris Corp., Gaithersburg, Md.).

Detection of Phosphonucleolin in Cell Lysates

4E2 anti-nucleolin antibody (Research Diagnostics Inc., Flanders, N.J.) was biotinylated using Origen Biotin-LC-NHS-Ester (BioVeris Corp.) using the protocol described by the manufacturer. Goat anti-mouse antibody (Jackson Immuno Research, West Grove, Pa.) was ruthenylated employing a ruthenylation kit (BioVeris Corp.; cat# 110034) according to the protocol described by the manufacturer. To each well of a 96-well plate is added 25 µL of antibody buffer (phospho buffered saline pH7.2, 1% bovine serum albumin, 0.5% Tween-20) containing 2 µg/ml biotynylated 4E2 anti-nucleolin antibody and 0.4 mg/ml streptavidin coated paramagnetic Dynabeads (BioVeris Corp.) along with 25 µL of cell lysate (above). The antibodies and lysate are incubated with shaking for 1 hr at room temperature. Next, 50 ng of anti-phosphonucleolin TG3 antibody (Applied NeuroSolutions Inc., Vernon Hills, Ill.) in a volume of 50 µL of antibody buffer (above) are added to each well of the lysate mix and incubation is continued for 30 min at room temperature. Lastly, 25 µL of a 240 ng/ml solution of the ruthenylated goat anti-mouse antibody in antibody buffer is added to each well and incubation continued for 3 hours at room temperature. The lysate antibody mixtures are read in a BioVeris M-series M8 analyser and EC50s for compound dependent increases in phosphor-nucleolin are determined.

Example 7

Other Biological Assays

CHK1 Expression and Purification: Recombinant human CHK1 can be expressed as a fusion protein with glutathione S-transferase at the amino-terminus (GST-CHK1) using standard baculovirus vectors and a (Bac-to-Bac®) insect cell expression system purchased from GIBCO™ Invitrogen. Recombinant protein expressed in insect cells can be purified using glutathione sepharose (Amersham Biotech) using standard procedures described by the manufacturer.

CHK1 Fluorescense Polarization Assays: CHK1 kinase inhibitors can be identified using fluorescence polarization to monitor kinase activity. This assay utilizes 10 nM GST-CHK1 and contains 5 mM 2-(N-Morpholino)ethanesulfonic acid (MES, pH 6.5), 5 mM magnesium chloride ($MgCl_2$), 0.05% Tween®-20, 1 µM adenosine 5' triphosphate (ATP), 2 mM 1,4-Dithio-DL-threitol (DTT), 1 µM peptide substrate (Biotin-ILSRRPSYRKILND-free acid) (SEQ ID NO: 19), 10 nM peptide substrate tracer (Fluorescine-GSRRP-pS-YRKI-free acid) (pS=phosphorylated-Serine) (SEQ ID NO: 20), 60 ng anti-phospho-CREB(S133) mouse monoclonal IgG purified on Protein G sepharose from crude mouse ascites purchased from Cell Signalling Technologies (Beverly, Mass.), 4% dimethyl sulfoxide (DMSO) and 30 µM inhibitor compound. Reactions are incubated at room temperature for 140 minutes and terminated by addition of 25 mM EDTA (pH 8.0). Stopped reactions are incubated for 120 minutes at room temperature and fluorescence polarization values determined using a Molecular Devices/LJL Biosystems Analyst™ AD (Sunnyvale, Calif.) with standard fluorescine settings.

CHK1 SPA Filtration Assay: Assays (25 µl) contain 10 nM GST-CHK1, 10 mM MES, 2 mM DTT, 10 mM $MgCl_2$, 0.025% Tween®-20, 1 uM peptide substrate (Biotin-ILSRRPSYRKILND-free acid) (SEQ ID NO: 19), 1 µM ATP, 0.1 µCi $^{33}$P-γ-ATP (New England Nuclear, NEN) and are reacted for 90 minutes at room temperature. Reactions are terminated by adding 55 µl of phosphate buffered saline containing 50 mM EDTA, 6.9 mM ATP, 0.5 mg Scintillation proximity assay (SPA) beads (Amersham Biosciences). Peptide substrate is allowed to bind beads for 10 minutes at room temperature followed by filtration on a Packard GF/B Unifilter plate and washed with phosphate buffered saline. Dried plates may are sealed with Topseal™ (NEN) and $^{33}$P incorporated to peptide substrate using a Packard Topcount® scintillation counter with standard settings for $^{33}$P.

CHK1 FlashPlate® Kinase Assay: Assays (25 µl) contain 8.7 GST-CHK1, 10 mM MES, 0.1 mM ethylene glycol-bis (β-aminoethylether)-N,N,N',N'-tetracetic acid (EGTA, pH 8.0), 2 mM DTT, 0.05% Tween 20, 3 µM peptide substrate (Biotin-ILSRRPSYRKILND-free acid) (SEQ ID NO: 19), 1 µM ATP, 0.4 µCi 33P-γ-ATP (NEN) and 4% DMSO. Reactions are incubated for 30 minutes at room temperature, terminated with 50 µl of 50 mM EDTA. 90 µl of reaction is transferred to streptavidin-coated FlashPlates® (NEN) and incubated for 1 hour at room temperature. Plates are washed with phosphate buffered saline containing 0.01% Tween-20 and 10 mM sodium pyrophosphate. Plates are dried, sealed with Topseal™ (NEN) and an amount of $^{33}$P incorporated into the peptide substrate measured using a Packard Topcount® NXT™ scintillation counter with standard settings.

CHK1 DELFIA® Kinase Assay: Assays (25 µl) utilize 6.4 mM GST-CHK1 containing 25 mM Tris, pH 8.5, 20% glycerol, 50 mM sodium chloride (NaCl), 0.1 Surfact-Amps® 20, 1 µM peptide substrate (Biotin-GLYRSPSMPEN-amide) (SEQ ID NO: 21), 2 mM DTT, 4% DMSO, 12.5 µM ATP, 5 mM $MgCl_2$ and are reacted for 30 minutes at room temperature. Reactions are terminated with 100 µl Stop buffer containing 1% BSA, 10 mM Tris, pH 8.0, 150 mM NaCl and 100 mM EDTA. Stopped reactions (100 µl) are transferred to 96 well neutravidin plates (Pierce) to capture the biotin-peptide substrate during a 30 minute room temperature incubation. Wells are washed and reacted with 100 µl PerkinElmer Wallac Assay Buffer containing 21.5 ng/ml anti-phospho-Ser216-Cdc25c rabbit polyclonal antibody from Cell Signalling Technology (Beverly, Mass.) and 292 ng/ml europium labeled anti-rabbit-IgG for 1 hour at room temperature. Wells are washed and europium released from the bound antibody by addition of Enhancement Solution (100 µl) (PerkinElmer Wallac) and detected using a Wallac Victor2™ using standard manufacturer settings.

Compounds of the present invention may be tested in the CHK1 FlashPlate® Kinase Assay described above.

WST Assay: HT29,HCT116 (5000 cells/well) or other cells are seeded (75 µl) to 96 well clear bottom plates at densities which provide linear growth curves for 72 hours. Cells are cultured under sterile conditions in appropriate media and for HT29 and HCT116 this media is McCoy's 5A containing 10% Fetal Bovine Serum (FBS). Following the initial seeding of cells, cells are incubated at 37° C., 5% $CO_2$ from 17 to 24 hours at which time the appropriate DNA damaging agents (camptothicins, 5-fluorouracil and etoposide) are added at increasing concentrations to a point which is capable of causing at least 80% cell killing within 48 hours. Final volume of all DNA damaging agent and compound additions are 25 µl. Assays contain <1% DMSO final. At the same time as DNA damaging agent addition, CHK1 inhibitor compound is added at fixed concentrations to each DNA damaging agent titration to observe enhancement of cell killing. Cell viability/cell killing under the conditions described above are determined by addition of WST reagent (Roche) according to the manufacturer at 47 hours following DNA damage and CHK1 inhibitor compound addition and following a 3.5 hour or 2.5 hour incubation at 37° C., 5% $CO_2$ wherein $OD_{450}$ is measured.

Compounds of the present invention may be tested in the assays described above.

Example 8

Other Biological Assays

Other assays that may be utilized to determine biological activity of the instant compounds include assays found in the following publications: WO 04/080973, WO 02/070494, and WO 03/101444.

What is claimed is:

1. A compound of the Formula E:

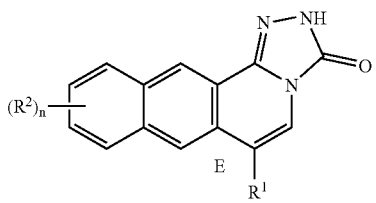

wherein:
n is 0, 1, or 2;
$R^2$ is independently selected from: heterocyclyl, halogen, $(C_1-C_6)$alkyl, $CF_3$, $(C_2-C_6)$alkenyl, and aryl, said heterocyclyl, alkenyl, aryl, are optionally substituted with one to three substituents selected from, $(C_1-C_6)$alkyl, $NH_2$, halogen, —O$(C_1-C_6)$alkyl, heterocyclyl, and -$(C_1-C_6)$alkyl-$NH_2$;
$R^1$ is selected from: H, —O$(C_1-C_6)$alkyl, $(C_1-C_6)$alkyl, halogen, $(C_2-C_6)$alkenyl, heterocyclyl, and aryl, said alkyl, alkenyl, heterocyclyl and aryl are optionally substituted with from one to three substituents selected from, halogen, -$(C_1-C_6)$alkyl-$NH_2$, -$(C_1-C_6)$alkyl-heterocyclyl, —N$(R^b)_2$—$CF_3$, N$(R^b)_2$, OH, —NH—(C=O)$CF_3$, and —NH—(C=O)O$(C_1-C_6)$alkyl;
$R^b$ is independently selected from, H and $(C_1-C_6)$alkyl;
or a pharmaceutically acceptable salt or a stereoisomer thereof.

2. A compound which is selected from:
6-[(1E)-3-aminoprop-1-en-1-yl) benzo[g][1,2,4]triazolo[3,4-a]isoquinolin-3(2H)-one;
6-(3-aminopropyl) benzo[g][1,2,4]triazolo[3,4-a]isoquinolin-3(2H)-one;
6-(3-aminopropyl)-5.6-dihydrobenzo[g][1,2,4]triazolo[3,4-a]isoquinolin-3(2H)-one;
6-pyridin-3-ylbenzo[g][1,2,4]triazolo[3,4-a]isoquinolin-3(2H)-one;
6-[4-(aminomethyl)phenyl]benzo[g][1,2,4]triazolo[3,4-a]isoquinolin-3(2H)-one;
6-[4-(morpholin-4-ylmethyl)phenyl]benzo[g][1,2,4]triazolo[3,4-a]isoquinolin-3(2H)-one;
6-(1,2,3,6-tetrahydro-4-pyridinyl)-benzo[g]-1,2,4-triazolo[3,4-a]isoquinolin-3(2H)-one;
6-(6-aminopyridin-3-yl)benzo[g][1,2,4]triazolo[3,4-a]isoquinolin-3(2H)-one;
6-[3-(morpholin-4-ylmethyl)phenyl]benzo[g][1,2,4]triazolo[3,4-a]isoquinolin-3(2H)-one;
6-[3-(piperidin-1-ylmethyl)phenyl]benzo[g][1,2,4]triazolo[3,4-a]isoquinolin-3(2H)-one;
6-[3-(aminomethyl)phenyl]benzo[g][1,2,4]triazolo[3,4-a]isoquinolin-3(2H)-one;
6-(2-aminoethyl)benzo[g][1,2,4]triazolo[3,4-a]isoquinolin-3(2H)-one;
6-isoquinolin-5-ylbenzo[g][1,2,4]triazolo[3,4-a]isoquinolin-3(2H)-one;
6-quinolin-5-ylbenzo[g][1,2,4]triazolo[3,4-a]isoquinolin-3(2H)-one;
6-(3-aminophenyl)benzo[g][1,2,4]triazolo[3,4-a]isoquinolin-3(2H)-one;
6-piperidin-4-ylbenzo[g][1,2,4]triazolo[3,4-a]isoquinolin-3(2H)-one;
2,2,2-trifluoro-N-[4-(3-oxo-2,3-dihydrobenzo[g][1,2,4]triazolo[3,4-a]isoquinolin-6-yl)phenyl]acetamide;
6-(4-aminophenyl)benzo[g][1,2,4]triazolo[3,4-a]isoquinolin-3(2H)-one;
6-pyridin-4-ylbenzo[g][1,2,4]triazolo[3,4-a]isoquinolin-3(2H)-one;
6-(3-aminopropyl)-10-methylbenzo[g][1,2,4]triazolo[3,4-a]isoquinolin-3(2H)-one;
6-(3-aminopropyl)-10-fluorobenzo[g][1,2,4]triazolo[3,4-a]isoquinolin-3(2H)-one;
6-(3-aminopropyl)-9,11-difluorobenzo[g][1,2,4]triazolo[3,4-a]isoquinolin-3(2H)-one;
tert-butyl[(2Z)-3-(10-methyl-3-oxo-2,3-dihydrobenzo[g][1,2,4]triazolo[3,4-a]isoquinolin-3(2H)-one;
6-[(1Z)-3-aminoprop-1-en-1-yl]-10-methylbenzo[g][1,2,4]triazolo[3,4-a]isoquinolin-3(2H)-one;
6-[(1Z)-3-aminoprop-1-en-1-yl]-10-chlorobenzo[g][1,2,4]triazolo[3,4-a]isoquinolin-3(2H)-one;
6-[4-(aminomethyl)phenyl]-10-methylbenzo[g][1,2,4]triazolo[3,4-a]isoquinolin-3(2H)-one;
6-(3-aminopropyl)-10-chlorobenzo[g][1,2,4]triazolo[3,4-a]isoquinolin-3 (2H)-one;
6-[(1Z)-3-aminoprop-1-en-1-yl]-9,10-difluorobenzo[g][1,2,4]triazolo[3,4-a]isoquinolin-3(2H)-one;
6-(3-aminopropyl)-9, 10-difluorobenzo [g][1,2,4]triazolo[3,4-a]isoquinolin-3(2H)-one;
6-(3-aminopropyl)-10-(trifluoromethyl)benzo[g][1,2,4]triazolo[3,4-a]isoquinolin-3(2H)-one;
or a pharmaceutically acceptable salt or a stereoisomer thereof.

3. A compound which is:
6-(3-aminopropyl)benzo[g][1,2,4]triazolo[3,4-a]isoquinolin-3(2H)-one;
or a pharmaceutically acceptable salt thereof.

4. An HCl salt of a compound which is:
6-(3-aminopropyl)benzo[g][1,2,4]triazolo[3,4-a]isoquinolin-3(2H)-one.

5. A pharmaceutical composition comprising a pharmaceutical carrier, and a therapeutically effective amount of a compound of claim 3.

* * * * *

SEQUENCE LISTING

```
<160> 21

<210> 1
<211> 28
<212> DNA
<213> Artificial Sequence
<220>
<223> Completely Synthetic DNA Sequence

<400> 1
atcagcaaga attaccattc cagacatc                                      28

<210> 2
<211> 28
<212> DNA
<213> Artificial Sequence
<220>
<223> Completely Synthetic DNA Sequence

<400> 2
catacaactt ttcttccatt gatagccc                                      28

<210> 3
<211> 19
<212> DNA
<213> Artificial Sequence
<220>
<223> Completely Synthetic DNA Sequence

<400> 3
gttacttggc accccagga                                                19

<210> 4
<211> 27
```

```
<212> DNA
<213> Artificial Sequence
<220>
<223> Completely Synthetic DNA Sequence

<400> 4
catccaattt ggtaaagaat cgtgtca                                27

<210> 5
<211> 15
<212> DNA
<213> Artificial Sequence
<220>
<223> Completely Synthetic DNA Sequence

<400> 5
tcctcacaga acccc                                             15

<210> 6
<211> 26
<212> DNA
<213> Artificial Sequence
<220>
<223> Completely Synthetic DNA Sequence

<400> 6
gcacattcaa tccaatttgg acttct                                 26

<210> 7
<211> 28
<212> DNA
<213> Artificial Sequence
<220>
<223> Completely Synthetic DNA Sequence

<400> 7
catccaattt ggtaaagaat cgtgtcat                               28

<210> 8
<211> 17
<212> DNA
<213> Artificial Sequence
<220>
<223> Completely Synthetic DNA Sequence

<400> 8
cagtgcttct agaaccc                                           17

<210> 9
<211> 24
<212> DNA
<213> Artificial Sequence
<220>
<223> Completely Synthetic DNA Sequence

<400> 9
tgcatccaat ttggtaaaga atcg                                   24

<210> 10
<211> 62
<212> DNA
<213> Artificial Sequence
<220>
<223> Completely Synthetic DNA Sequence

<400> 10
```

```
ttactggctt atcgaaatta atacgactca ctatagggag gagtcatggc agtgcccttt    60
gt                                                                  62

<210> 11
<211> 64
<212> DNA
<213> Artificial Sequence
<220>
<223> Completely Synthetic DNA Sequence

<400> 11
tagaaggcac agtcgaggct gatcagcggg tttaaactca tgcatccaat ttggtaaaga   60
atcg                                                                64

<210> 12
<211> 80
<212> DNA
<213> Artificial Sequence
<220>
<223> Completely Synthetic DNA Sequence

<400> 12
aatccaattt ggacttctct ccagtaaaca gtgcttctag aaccctggc agcggttggt     60 caaaagaatg acacgattct                                               80

<210> 13
<211> 80
<212> DNA
<213> Artificial Sequence
<220>
<223> Completely Synthetic DNA Sequence

<400> 13
agaatcgtgt cattcttttg accaaccgct gccaggggtt ctagaagcac tgtttactgg   60
agagaagtcc aaattggatt                                               80

<210> 14
<211> 954
<212> DNA
<213> Artificial Sequence
<220>
<223> Completely Synthetic DNA Sequence

<400> 14
atggcagtgc cctttgtgga agactgggac ttggtgcaaa ccctgggaga aggtgcctat    60
ggagaagttc aacttgctgt gaatagagta actgaagaag cagtcgcagt gaagattgta   120
gatatgaagc gtgccgtaga ctgtccagaa aatattaaga agagatctg tatcaataaa   180 atgctaaatc atgaaaatgt agtaaaattc tatggtcaca ggagagaagg caatatccaa   240
tatttatttc tggagtactg tagtggagga gagcttttg acagaataga gccagacata   300
ggcatgcctg aaccagatgc tcagagattc ttccatcaac tcatggcagg ggtggtttat   360
ctgcatggta ttgaataac tcacagggat attaaaccag aaaatcttct gttggatgaa   420
agggataacc tcaaaatctc agactttggc ttggcaacag tatttcggta taataatcgt   480
gagcgtttgt tgaacaagat gtgtggtact ttaccatatg ttgctccaga acttctgaag   540
agaagagaat tcatgcagga accagttgat gtttggtcct gtggaatagt acttactgca   600
atgctcgctg gagaattgcc atgggaccaa cccagtgaca gctgtcagga gtattctgac   660
tggaaagaaa aaaaaacata cctcaaccct tggaaaaaaa tcgattctgc tcctctagct   720
```

-continued

```
ctgctgcata aaatcttagt tgagaatcca tcagcaagaa ttaccattcc agacatcaaa      780
aaagatagat ggtacaacaa accoctcaag aaaggggcaa aaaggccccg agtcacttca      840
ggtggtgtgt cagagtctcc cagtggattt tctaagcaca ttcaatccaa tttggacttc      900
tctccagtaa acagtgcttc tagaaccoct ggcagcggtt ggtcaaaaga atga            954
```

<210> 15
<211> 317
<212> PRT
<213> Artificial Sequence
<220>
<223> Completely Synthetic Amino Acid Sequence

<400> 15

```
Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Arg Thr Pro Gly Ser Gly Trp Ser Lys Glu
305                 310                 315
```

-continued

<210> 16
<211> 40
<212> DNA
<213> Artificial Sequence
<220>
<223> Completely Synthetic DNA Sequence

<400> 16
cccggaattc accatggcag tgcccttttgt ggaagactgg    40

<210> 17
<211> 54
<212> DNA
<213> Artificial Sequence
<220>
<223> Completely Synthetic DNA Sequence

<400> 17
tgtgtccggc cgtcagtgat ggtgatggtg atgttctttt gaccaaccgc tgcc    54

<210> 18
<211> 13
<212> PRT
<213> Artificial Sequence
<220>
<223> Completely Synthetic Amino Acid Sequence

<400> 18

Gly Gly Arg Ala Arg Thr Ser Ser Phe Ala Glu Pro Gly
1               5                   10

<210> 19
<211> 14
<212> PRT
<213> Artificial Sequence
<220>
<223> Completely Synthetic Amino Acid Sequence

<400> 19

Ile Leu Ser Arg Arg Pro Ser Tyr Arg Lys Ile Leu Asn Asp
1               5                   10

<210> 20
<211> 10
<212> PRT
<213> Artificial Sequence
<220>
<223> Completely Synthetic Amino Acid Sequence

<400> 20

Gly Ser Arg Arg Pro Ser Tyr Arg Lys Ile
1               5                   10

<210> 21
<211> 11
<212> PRT
<213> Artificial Sequence
<220>
<223> Completely Synthetic Amino Acid Sequence

<400> 21

Gly Leu Tyr Arg Ser Pro Ser Met Pro Glu Asn
1               5                   10